United States Patent
Mohler et al.

(10) Patent No.: US 10,738,278 B2
(45) Date of Patent: Aug. 11, 2020

(54) ENGINEERED CELLS FOR ADOPTIVE CELL THERAPY

(71) Applicant: Juno Therapeutics, Inc., Seattle, WA (US)

(72) Inventors: Kendall M. Mohler, Seattle, WA (US); Hyam I. Levitsky, Seattle, WA (US)

(73) Assignee: Juno Therapeutics, Inc., Seattle, WA (US)

(*) Notice: Subject to any disclaimer, the term of this patent is extended or adjusted under 35 U.S.C. 154(b) by 275 days.

(21) Appl. No.: 15/326,441

(22) PCT Filed: Jul. 15, 2015

(86) PCT No.: PCT/US2015/040660
§ 371 (c)(1),
(2) Date: Jan. 13, 2017

(87) PCT Pub. No.: WO2016/011210
PCT Pub. Date: Jan. 21, 2016

(65) Prior Publication Data
US 2017/0204372 A1    Jul. 20, 2017

Related U.S. Application Data

(60) Provisional application No. 62/025,006, filed on Jul. 15, 2014.

(51) Int. Cl.
| | |
|---|---|
| *C12N 5/10* | (2006.01) |
| *C12N 5/0783* | (2010.01) |
| *C12N 15/12* | (2006.01) |
| *C12N 15/11* | (2006.01) |
| *A61K 39/00* | (2006.01) |
| *A61K 38/17* | (2006.01) |
| *C07K 16/30* | (2006.01) |
| *C07K 14/725* | (2006.01) |
| *C07K 14/705* | (2006.01) |
| *C07K 16/40* | (2006.01) |

(52) U.S. Cl.
CPC .......... *C12N 5/0638* (2013.01); *A61K 39/00* (2013.01); *A61K 39/0011* (2013.01); *C07K 14/7051* (2013.01); *C07K 14/70521* (2013.01); *C07K 16/30* (2013.01); *C07K 16/40* (2013.01); *C12N 5/0636* (2013.01); *C12Y 204/99* (2013.01); *C12Y 207/07049* (2013.01); *A61K 2039/5156* (2013.01); *A61K 2039/5158* (2013.01); *C07K 2317/622* (2013.01); *C07K 2317/76* (2013.01); *C07K 2319/02* (2013.01); *C07K 2319/03* (2013.01); *C07K 2319/33* (2013.01); *C07K 2319/74* (2013.01); *C12N 2510/00* (2013.01)

(58) Field of Classification Search
None
See application file for complete search history.

(56) References Cited

U.S. PATENT DOCUMENTS

| | | |
|---|---|---|
| 4,235,871 A | 11/1980 | Papahadjopoulos et al. |
| 4,452,773 A | 6/1984 | Molday |
| 4,501,728 A | 2/1985 | Geho et al. |
| 4,690,915 A | 9/1987 | Rosenberg |
| 4,795,698 A | 1/1989 | Owen et al. |
| 4,837,028 A | 6/1989 | Allen |
| 4,897,355 A | 1/1990 | Eppstein et al. |
| 4,946,787 A | 8/1990 | Eppstein et al. |
| 5,019,369 A | 5/1991 | Presant et al. |
| 5,049,386 A | 9/1991 | Eppstein et al. |
| 5,087,616 A | 2/1992 | Myers et al. |
| 5,200,084 A | 4/1993 | Liberti et al. |
| 5,219,740 A | 6/1993 | Miller et al. |
| 5,356,802 A | 10/1994 | Chandrasegaran |
| 5,436,150 A | 7/1995 | Chandrasegaran |
| 5,487,994 A | 1/1996 | Chandrasegaran |
| 6,040,177 A | 3/2000 | Riddell et al. |
| 6,140,081 A | 10/2000 | Barbas |
| 6,207,453 B1 | 3/2001 | Maass et al. |

(Continued)

FOREIGN PATENT DOCUMENTS

| | | |
|---|---|---|
| EP | 452342 | 10/1991 |
| EP | 2537416 | 11/2014 |

(Continued)

OTHER PUBLICATIONS

US 8,252,592 B2, 08/2012, Sadelain et al. (withdrawn)
Crossland, CD56-Specific T Cells: Using Genetically Engineered T Cells to Redirect Specificity to a T Cell Expressed Antigen, UT GSBS Dissertation, 2014, pp. 1-232.*
Mamonkin et al ,A T-cell-directed chimeric antigen receptor for the selective treatment of T-cell malignancies, Blood, 2015, pp. 983-992.*

(Continued)

*Primary Examiner* — Maria Marvich
(74) *Attorney, Agent, or Firm* — Morrison Foerster LLP

(57) ABSTRACT

Provided are engineered cells for adoptive therapy, including NK cells and T cells. Also provided are compositions for engineering and producing the cells, compositions containing the cells, and methods for their administration to subjects. In some aspects, features of the cells and methods provide specificity and/or efficacy. In some embodiments, the cells contain genetically engineered antigen receptors that specifically bind to antigens, such as chimeric antigen receptors (CARs) and costimulatory receptors. In some embodiments, the cells include receptors targeting multiple antigens. In some embodiments, the cells include repression of one or more gene product, for example, by disruption of a gene encoding the gene product. In some embodiments, a gene encoding an antigen recognized by the engineered antigen receptor is disrupted, reducing the likelihood of targeting of the engineered cells.

21 Claims, No Drawings
Specification includes a Sequence Listing.

(56) References Cited

U.S. PATENT DOCUMENTS

| | | |
|---|---|---|
| 6,410,319 B1 | 6/2002 | Raubitschek et al. |
| 6,451,995 B1 | 9/2002 | Cheung et al. |
| 6,453,242 B1 | 9/2002 | Eisenberg et al. |
| 6,503,717 B2 | 1/2003 | Case et al. |
| 6,534,261 B1 | 3/2003 | Cox et al. |
| 6,599,692 B1 | 7/2003 | Case et al. |
| 6,689,558 B2 | 2/2004 | Case |
| 6,794,136 B1 | 9/2004 | Eisenberg et al. |
| 7,030,215 B2 | 4/2006 | Liu et al. |
| 7,067,317 B2 | 6/2006 | Rebar et al. |
| 7,070,934 B2 | 7/2006 | Cox et al. |
| 7,070,995 B2 | 7/2006 | Jensen |
| 7,253,273 B2 | 8/2007 | Collingwood |
| 7,262,054 B2 | 8/2007 | Jamieson et al. |
| 7,265,209 B2 | 9/2007 | Jensen |
| 7,354,762 B2 | 4/2008 | Jensen |
| 7,361,635 B2 | 4/2008 | Miller et al. |
| 7,446,179 B2 | 11/2008 | Jensen |
| 7,446,190 B2 | 11/2008 | Sadelain et al. |
| 7,446,191 B2 | 11/2008 | Jensen et al. |
| 7,718,777 B2 | 5/2010 | Hoogenboom et al. |
| 7,892,559 B2 | 2/2011 | Straten et al. |
| 8,008,450 B2 | 8/2011 | Williams et al. |
| 8,153,765 B2 | 4/2012 | Park et al. |
| 8,324,353 B2 | 12/2012 | Jensen |
| 8,389,282 B2 | 3/2013 | Sadelain et al. |
| 8,399,645 B2 | 3/2013 | Campana et al. |
| 8,497,118 B2 | 7/2013 | Jensen |
| 8,603,477 B2 | 12/2013 | Afar et al. |
| 2002/0131960 A1 | 9/2002 | Sadelain et al. |
| 2002/0150914 A1 | 10/2002 | Andersen et al. |
| 2003/0170238 A1 | 9/2003 | Gruenberg et al. |
| 2003/0223994 A1 | 12/2003 | Hoogenboom et al. |
| 2005/0064474 A1 | 3/2005 | Urnov et al. |
| 2005/0267061 A1 | 12/2005 | Martin |
| 2006/0179501 A1* | 8/2006 | Chan ............... A01K 67/0275 800/18 |
| 2006/0188987 A1 | 8/2006 | Guschin et al. |
| 2007/0218528 A1 | 9/2007 | Miller |
| 2009/0004214 A1 | 1/2009 | Wang et al. |
| 2009/0226474 A1 | 9/2009 | Weidanz et al. |
| 2011/0003380 A1 | 1/2011 | Miltenyi et al. |
| 2011/0059502 A1 | 3/2011 | Chalasani |
| 2011/0301073 A1 | 12/2011 | Gregory et al. |
| 2012/0035529 A1 | 2/2012 | Coukos |
| 2012/0189622 A1 | 7/2012 | Tesar et al. |
| 2012/0321667 A1* | 12/2012 | Sentman .............. C12N 5/0636 424/278.1 |
| 2013/0149337 A1 | 6/2013 | Cooper et al. |
| 2013/0287748 A1 | 10/2013 | June et al. |
| 2013/0315884 A1 | 11/2013 | Galetto et al. |
| 2014/0065708 A1 | 3/2014 | Weidanz |
| 2014/0068797 A1 | 3/2014 | Doudna |
| 2014/0099309 A1* | 4/2014 | Powell, Jr. .......... A61K 35/17 424/135.1 |
| 2014/0120622 A1 | 5/2014 | Gregory et al. |
| 2014/0242701 A1 | 8/2014 | Shiku et al. |
| 2014/0271635 A1 | 9/2014 | Brogdon |
| 2014/0294841 A1 | 10/2014 | Scheinberg et al. |
| 2015/0051266 A1 | 2/2015 | Kochenderfer |
| 2015/0328292 A1* | 11/2015 | Spencer ............ A61K 38/4873 424/93.21 |
| 2017/0035866 A1 | 2/2017 | Poirot |
| 2017/0274014 A1* | 9/2017 | Brogdon .............. A61K 39/12 |
| 2018/0161368 A1* | 6/2018 | Odegard .............. A61K 35/17 |
| 2018/0318349 A1 | 11/2018 | Thompson |
| 2019/0136230 A1 | 5/2019 | Sather et al. |
| 2019/0201442 A1 | 7/2019 | Mohler |

FOREIGN PATENT DOCUMENTS

| | | |
|---|---|---|
| JP | 2013-116891 | 6/2013 |
| JP | 2015-513920 | 5/2015 |
| WO | WO-1991/016024 | 10/1991 |
| WO | WO-1991/017424 | 11/1991 |
| WO | WO-1992/008796 | 5/1992 |
| WO | WO-1994/028143 | 12/1994 |
| WO | WO-1998/053058 | 11/1998 |
| WO | WO-1998/053059 | 11/1998 |
| WO | WO-1998/053060 | 11/1998 |
| WO | WO-2000/014257 | 3/2000 |
| WO | WO-2000/025813 | 5/2000 |
| WO | WO-2002/016536 | 2/2002 |
| WO | WO 2002/066516 | 8/2002 |
| WO | WO-2003/016496 | 2/2003 |
| WO | WO-2006/099875 | 9/2006 |
| WO | WO-2009/072003 | 6/2009 |
| WO | WO-2009/080829 | 7/2009 |
| WO | WO-2010/033140 | 3/2010 |
| WO | WO-2010/075417 | 7/2010 |
| WO | WO-2011/009173 | 1/2011 |
| WO | WO-2012/092612 | 7/2012 |
| WO | WO-2012/129514 | 9/2012 |
| WO | WO-2012/135854 | 3/2013 |
| WO | WO 2013/051718 | 4/2013 |
| WO | WO-2013/071154 | 5/2013 |
| WO | WO-2013/123061 | 8/2013 |
| WO | WO-2013/126726 | 8/2013 |
| WO | WO-2013/135553 | 9/2013 |
| WO | WO 2013/154760 | 10/2013 |
| WO | WO-2013/166321 | 11/2013 |
| WO | WO-2013/176915 | 11/2013 |
| WO | WO 2014/011988 | 1/2014 |
| WO | WO-2014/031687 | 2/2014 |
| WO | WO-2014/055668 | 4/2014 |
| WO | WO 2014/100385 | 6/2014 |
| WO | WO 2014/138704 | 9/2014 |
| WO | WO 2014/059173 | 10/2014 |
| WO | WO 2014/191128 | 12/2014 |
| WO | WO 2014/210064 | 12/2014 |
| WO | WO 2015/075468 | 5/2015 |
| WO | WO-2015/121454 | 8/2015 |
| WO | WO 2015/161276 | 10/2015 |
| WO | WO-2016/196388 | 12/2016 |
| WO | WO-2017/011804 | 1/2017 |
| WO | WO 2017/193107 | 11/2017 |
| WO | WO 2018/071873 | 10/2018 |

OTHER PUBLICATIONS

Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2:e93.

Anderson, "Human gene therapy," Science (1992) 256(5058):808-813.

Baum et al., "Retrovirus vectors: toward the plentivirus?," Molecular Therapy: The Journal of the American Society of Gene Therapy (2006) 13:1050-1063.

Beerli et al., "Engineering polydactyl zinc-finger transcription factors," Nat Biotechnol. (2002) 20(2):135-141.

Benson et al., "CS1-directed monoclonal antibody therapy for multiple myeloma," J Clin Oncol. (2012) 30(16):2013-2015.

Boris-Lawrie et al., "Recent advances in retrovirus vector technology," Cur. Opin. Genet. Develop. (1993) 3:102-109.

Brash et al., "Strontium phosphate transfection of human cells in primary culture: stable expression of the simian virus 40 large-T-antigen gene in primary human bronchial epithelial cells," Mol. Cell Biol. (1987) 7:2031-2034.

Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.

Carlens et al., "Ex vivo T lymphocyte expansion for retroviral transduction: influence of serum-free media on variations in cell expansion rates and lymphocyte subset distribution," Exp Hematol (2000) 28(10):1137-46.

Cavalieri et al., "Human T lymphocytes transduced by lentiviral vectors in the absence of TCR activation maintain an intact immune competence," Blood (2003) 102(2):497-505.

(56) References Cited

OTHER PUBLICATIONS

Chen et al., "Differential lysis of tumors by polyclonal T cell lines and T cell clones specific for hTERT," Cancer Biol Ther. (2007) 6(12):1991-1996.
Chicaybam et al., "An efficient low cost method for gene transfer to T lymphocytes," PLoS ONE (2013) 8(3):e60298.
Cho et al., "Human mammalian cell sorting using a highly integrated micro-fabricated fluorescence-activated cell sorter (microFACS)," Lab Chip (2010) 10:1567-1573.
Choo et al., "Advances in zinc finger engineering," Curr Opin Struct Biol. (2000) 10(4):411-416.
Chothia et al., "The outline structure of the T-cell alpha beta receptor," EMBO J. (1988) 7(12):3745-3755.
Chu et al., "CS1-specific chimeric antigen receptor (CAR)-engineered natural killer cells enhance in vitro and in vivo antitumor activity against human multiple myeloma," Leukemia. (2014) 28(4):917-927.
Clackson et al., "Making antibody fragments using phage display libraries," Nature (1991) 352:624-628.
Clarke and Davies in: Methods in Molecular Medicine, vol. 58: Metastasis Research Protocols, vol. 2: Cell Behavior In Vitro and In Vivo, Edited by: S. A. Brooks and U. Schumacher© Humana Press Inc., Totowa, NJ (2001) pp. 17-25.
Cohen et al., "Recognition of fresh human tumor by human peripheral blood lymphocytes transduced with a bicistronic retroviral vector encoding a murine anti-p53 TCR," J Immunol. (2005) 175:5799-5808.
Cohen et al., "Recombinant antibodies with MHC-restricted, peptide-specific, T-cell receptor-like specificity: new tools to study antigen presentation and TCR-peptide-MHC interactions," J Mol Recognit. (2003) 16(5):324-332.
Cooper et al., "T-cell clones can be rendered specific for CD19: toward the selective augmentation of the graft-versus-B-lineage leukemia effect," Blood. (2003) 101:1637-1644.
Critchlow et al., "DNA end-joining: from yeast to man," Trends Biochem Sci. (1998) 23(10):394-398.
Davila et al., "CD19 CAR-targeted T cells induce long-term remission and B Cell Aplasia in an immunocompetent mouse model of B cell acute lymphoblastic leukemia," PLoS ONE (2013) 8(4):E61338.
Dillon, "Regulating gene expression in gene therapy," Trends Biotechnol. (1993) 11(5):167-173.
Fedorov et al., "Pd-1- and CTLA-4-based inhibitory chimeric antigen receptors (iCARs) divert off-target immunotherapy responses," Sci Transl Med. (2013) 5(215):215ra172.
Fracha et al., "Advances in the field of lentivector-based transduction of T and B lymphocytes for gene therapy," Molecular Therapy: The Journal of the American Society of Gene Therapy (2010) 18:1748-1757.
Gaj et al., "ZFN, TALEN, and CRISPR/Cas-based methods for genome engineering," Trends Biotechnol. (2013) 31(7):397-405.
Garfall et al., "Immunotherapy with chimeric antigen receptors for multiple myeloma," Discov Med. (2014) 17(91):37-46.
Godin et al., "Microfluidics and photonics for Bio-System-on-a-Chip: a review of advancements in technology towards a microfluidic flow cytometry chip," J Biophoton. (2008) 1(5):355-376.
Hackett et al., "A transposon and transposase system for human application," Molecular Therapy: The Journal of the American Society of Gene Therapy (2010) 18:674-683.
Haddada et al., "Gene therapy using adenovirus vectors," Curr Top Microbiol Immunol. (1995) 199 (Pt 3):297-306.
Hathcock et al., "Cutting edge: antigen-dependent regulation of telomerase activity in murine T cells," J Immunol. (1998) 160(12):5702-5706.
Hermans et al., "The VITAL assay: a versatile fluorometric technique for assessing CTL- and NKT-mediated cytotoxicity against multiple targets in vitro and in vivo," J. Immunological Methods (2004) 285(1):25-40.
Huang et al., "DNA transposons for modification of human primary T lymphocytes," Methods Mol Biol (2009) 506:115-126.
Isalan et al., "A rapid, generally applicable method to engineer zinc fingers illustrated by targeting the HIV-1 promoter," Nat Biotechnol. (2001) 19(7):656-660.
Janeway et al., Immunobiology: The Immune System in Health and Disease, 3rd Ed., Current Biology Publications (1997), p. 4:33.
Johnston, et al., "Biolistic transformation: microbes to mice," Nature (1990) 346:776-777.
Jores et al., "Resolution of hypervariable regions in T-cell receptor beta chains by a modified Wu-Kabat index of amino acid diversity," Proc Natl Acad Sci U S A. (1990) 87(23):9138-9142.
Kim et al., "A library of TAL effector nucleases spanning the human genome," Nat Biotechnol. (2013) 31(3):251-258.
Kim et al., "Chimeric restriction endonuclease," Proc Natl Acad Sci U S A. (1994) 91(3):883-887.
Kim et al., "Insertion and deletion mutants of FokI restriction endonuclease," J Biol Chem. (1994) 269(50):31978-31982.
Klebanoff et al., "Sorting through subsets: which T-cell populations mediate highly effective adoptive immunotherapy?," J Immunother. (2012) 35(9):651-660.
Kochenderfer et al., "Construction and preclinical evaluation of an anti-CD19 chimeric antigen receptor," J. Immunotherapy (2009) 32(7):689-702.
Koste et al., "T-cell receptor transfer into human T cells with ecotropic retroviral vectors," Gene Therapy (2014) 21:533-538.
Kremer et al., "Adenovirus and adeno-associated virus mediated gene transfer," Br Med Bull. (1995) 51(1):31-44.
Lefranc et al., "IMGT unique numbering for immunoglobulin and T cell receptor variable domains and Ig superfamily V-like domains," Dev Comp Immunol (2003) 27(1):55-77.
Leisegang et al., "MHC-restricted fratricide of human lymphocytes expressing survivin-specific transgenic T cell receptors," J Clin Invest. (2010) 120(11):3869-3877.
Li et al., "Directed evolution of human T-cell receptors with picomolar affinities by phage display," Nat Biotechnol. (2005) 23:349-354.
Li et al., "Functional domains in Fok I restriction endonuclease," Proc Natl Acad Sci U S A. (1992) 89(10):4275-4279.
Li et al.,"Alteration of the cleavage distance of Fok I restriction endonuclease by insertion mutagenesis," Proc Natl Acad Sci U S A. (1993) 90(7):2764-2768.
Liu et al., "Constitutive and regulated expression of telomerase reverse transcriptase (hTERT) in human lymphocytes," Proc Natl Acad Sci U S A. (1999) 96(9):5147-5152.
Lloyd et al., "Beyond the antigen receptor: editing the genome of T-cells; for cancer adoptive cellular therapies," Front Immunol. (2013) 4(221):1-7.
Lupton S. D. et al., "Dominant positive and negative selection using a hygromycin phosphotransferase-thymidine kinase fusion gene," Mol. and Cell Biol. (1991) 11(6):3374-3378.
Manuri et al., "piggyBac transposon/transposase system to generate CD19-specific T cells for the treatment of B-lineage malignancies," Hum Gene Ther (2010) 21(4):427-437.
Mardiros et al., "T cells expressing CD123-specific chimeric antigen receptors exhibit specific cytolytic effector functions and antitumor effects against human acute myeloid leukemia," Blood. (2013) 122(18):3138-3148.
Mihara et al., "Activated T-cell-mediated immunotherapy with a chimeric receptor against CD38 in B-cell non-Hodgkin lymphoma," J Immunother. (2009) 32(7):737-743.
Mihara et al., "T-cell immunotherapy with a chimeric receptor against CD38 is effective in eliminating myeloma cells," Leukemia. (2012) 26(2):365-367.
Miller et al., "Improved retroviral vectors for gene transfer and expression," BioTechniques (1989) 7:980-990.
Miller et al., "Retrovirus packaging cells," Human Gene Therapy (1990) 1:5-14.
Miller, "Human gene therapy comes of age," Nature. (1992) 357(6378):455-460.
Mitani et al., "Delivering therapeutic genes—matching approach and application," Trends Biotechnol. (1993) 11(5):162-166.

(56) References Cited

OTHER PUBLICATIONS

Miyazaki et al., "Development of a novel redirected T-cell-based adoptive immunotherapy targeting human telomerase reverse transcriptase for adult T-cell leukemia," Blood (2013) 121(24): 4894-4901.

Mullen et al., "Transfer of the bacterial gene for cytosine deaminase to mammalian cells confers lethal sensitivity to 5-fluorocytosine: a negative selection system," Proc. Natl. Acad. Sci. USA (1992) 89(1):33-37.

Nabel et al., "Direct gene transfer for immunotherapy and immunization," Trends Biotechnol. (1993) 11(5):211-215.

Pabo et al., "Design and selection of novel Cys2His2 zinc finger proteins," Annu Rev Biochem. (2001) 70:313-340.

Park et al., "Treating cancer with genetically engineered T cells," Trends Biotechnol. (2011) 29(11):550-557.

Parkhurst et al., "Characterization of genetically modified T-cell receptors that recognize the CEA:691-699 peptide in the context of HLA-A2.1 on human colorectal cancer cells," Clin Cancer Res. (2009) 15:169-180.

Portolano et al., "Lack of promiscuity in autoantigen-specific H and L chain combinations as revealed by human H and L chain "roulette"," J. Immunol. (1993) 150:880-887.

Riddell et al., "Phase I study of cellular adoptive immunotherapy using genetically modified CD8+ HIV-specific T cells for HIV seropositive patients undergoing allogeneic bone marrow transplant," Human Gene Therapy (1992) 3:319-338.

Rosenberg, "Cell transfer immunotherapy for metastatic solid cancer—what clinicians need to know," Nat rev Clin Oncol. (2011) 8(10):577-585.

Rosenberg, et al., "Use of tumor-infiltrating lymphocytes and interleukin-2 in the immunotherapy of patients with metastatic melanoma. A preliminary report," N Engl J Med. (1988) 319:1676-1680.

Rufer et al., "Transfer of the human telomerase reverse transcriptase (TERT) gene into T lymphocytes results in extension of replicative potential," Blood (2001) 98(3):597-603.

Sadelain et al., "The basic principles of chimeric antigen receptor design," Cancer Discov. (2013) 3(4):388-398.

Sander et al., "CRISPR-Cas systems for editing, regulating and targeting genomes," Nat Biotechnol. (2014) 32(4):347-355.

Scarpa et al., "Characterization of recombinant helper retroviruses from Moloney-based vectors in ecotropic and amphotropic packaging cell lines," Virology (1991) 180:849-852.

Segal et al., "Custom DNA-binding proteins come of age: polydactyl zinc-finger proteins," Curr Opin Biotechnol. (2001) 12(6):632-637.

Sharma et al., "Efficient sleeping beauty DNA transposition from DNA minicircles," Molec Ther Nucl Acids (2013) 2:e74.

Szoka et al., "Comparative properties and methods of preparation of lipid vesicles (liposomes)," Ann. Rev. Biophys. Bioeng. (1980) 9:467-508.

Tai et al., "Antibody-based therapies in multiple myeloma," Bone Marrow Res.(2011) 2011:924058.

Terakura et al., "Generation of CD19-chimeric antigen receptor modified CD8+ T cells derived from virus-specific central memory T cells," Blood (2012) 1:72-82.

Themeli et al., "Generation of tumor-targeted human T lymphocytes from induced pluripotent stem cells for cancer therapy," Nat Biotechnol. (2013) 31(10):928-933.

Theoret et al., "Relationship of p53 overexpression on cancers and recognition by anti-p53 T cell receptor-transduced T cells," Hum Gene Ther. (2008) 19(11):1219-1232.

Torikai et al., "A foundation for universal T-cell based immunotherapy: T cells engineered to express a CD19-specific chimeric-antigen-receptor and eliminate expression of endogenous TCR," Blood. (2012) 119(24):5697-5705.

Tsukahara et al., "CD19 target-engineered T-cells accumulate at tumor lesions in human B-cell lymphoma xenograft mouse models," Biochem Biophys Res Commun (2013) 438(1):84-9.

Turksma et al., "Exploring dendritic cell based vaccines targeting survivin for the treatment of head and neck cancer patients," J Transl Med. (2013) 11:152.

Turtle et al., "Engineered T cells for anti-cancer therapy," Curr. Opin. Immunol. (2012) 24(5):633-39.

Ugel et al., "Autoimmune B-cell lymphopenia after successful adoptive therapy with telomerase-specific T lymphocytes," Blood. (2010) 115(7):1374-1384.

Van Brunt, "Molecular Farming: Transgenic Animals as Bioreactors," Nat Biotechnol. (1988) 6(10):1149-1154.

Van Tendeloo et al., "High-level transgene expression in primary human T lymphocytes and adult bone marrow CD34+ cells via electroporation-mediated gene delivery," Gene Therapy (2000) 7(16):1431-1437.

Varela-Rohena et al., "Control of HIV-1 immune escape by CD8 T cells expressing enhanced T-cell receptor," Nat Med. (2008) 14:1390-1395.

Verhoeyen et al., "Lentiviral vector gene transfer into human T cells," Methods Mol Biol. (2009) 506:97-114.

Vigne et al., "Third-generation adenovectors for gene therapy," Restor Neurol Neurosci. (1995) 8(1):35-36.

Wadhwa et al., "Receptor mediated glycotargeting," J. Drug Targeting (1995) 3(2):111-127.

Wang et al., " Overcoming intrinsic inhibitory pathways to augment the antineoplastic activity of adoptively transferred T cells: Re-tuning your CAR before hitting a rocky road," Oncoimmunology. (2013) 2(11):e26492.

Wang et al., "Genetic screens in human cells using the CRISPR-Cas9 system," Science. (2014) 343(6166):80-84.

Wang et al., "Phenotypic and functional attributes of lentivirus-modified CD19-specific human CD8+ central memory T cells manufactured at clinical scale," J Immunother. (2012) 35(9):689-701.

Welstead et al., "Characterization of Cas9-Mediated Genome Editing in Human T Cells," Abstract of poster, presented at American Society of Gene and Cell Therapy 18th Annual Meeting, New Orleans, LA (2015) 23(Supplement 1):S138.

Weng et al., "Regulated expression of telomerase activity in human T lymphocyte development and activation," J Exp Med. (1996)183(6):2471-2479.

Wigler et al., "Transfer of purified herpes virus thymidine kinase gene to cultured mouse cells," Cell (1997) 11:223-232.

Wu et al., "Adoptive T-cell therapy using autologous tumor-infiltrating lymphocytes for metastatic melanoma: current status and future outlook," Cancer (2012) 18(2):160-175.

Yu et al., "Progress towards gene therapy for HIV infection," Gene Ther. (1994) 1(1):13-26.

Carpenter et al., "B-cell maturation antigen is a promising target for adoptive T-cell therapy of Multiple Myeloma," Clin Cancer Res (2013) 19(8):2048-2060.

Hudecek et al., "Receptor affinity and extracellular domain modifications affect tumor recognition by ROR1-specific chimeric antigen receptor T cells," Clin Cancer Res Jun. 15, 2013;19(12):3153-1364.

Lin et al., "Flow cytometric immunophenotypic analysis of 306 cases of Multiple Myeloma," Am J Clin Pathol (2004) 121:482-488.

Sandoval-Montes et al., "CD38 is expressed selectively during the activation of a subset of mature T cells with reduced proliferation but improved potential to produce cytokines," J. Leukoc. Biol. (2005) 77: 513-521.

Zhang et al., "Opportunities and challenges for anti-CD73 cancer therapy," Immunotherapy (2012) 4(9), 861-865.

Kimberley et al., "'April Hath Put a Spring of Youth in Everything':Relevance of April for Survival," J. Cell. Physiol. (2009) 218: 1-8.

Kindt et al., "Antigens and Antibodies," Kuby Immunology 6th Edition, W.H. Freeman and Co. (2007) Chapter 4, p. 91.

Ohta et al., "A2A Adenosine Receptor May Allow Expansion of T Cells Lacking Effector Functions in Extracellular Adenosine-Rich Microenvironments," J. Immunol. 183:5487-5493.

Pelekanou et al., "BAFF, APRIL, TWEAK, BCMA, TACI and Fn14 proteins are related to human glioma tumor grade:

(56) References Cited

OTHER PUBLICATIONS immunohistochemistry and public microarray data meta-analysis," PLoS One. Dec. 20, 2013;8(12):e83250.

Polson et al., "Expression pattern of the human FcRH/IRTA receptors in normal tissue and in B-chronic lymphocytic leukemia," Int Immunol. Sep. 2006;18(9):1363-73.

Salzer et al., "TACItly changing tunes: farewell to a yin and yang of BAFF receptor and TACI in humoral immunity? New genetic defects in common variable immunodeficiency," Curr Opin Allergy Clin Immunol. Dec. 2005;5(6):496-503.

Sanjana et al., "Improved vectors and genome-wide libraries for CRISPR screening," Nat Methods. Aug. 2014;11(8):783-784.

Wang et al., "TACI-ligand interactions are required for T cell activation and collagen-induced arthritis in mice," Nat Immunol. Jul. 2001;2(7):632-7.

Calatto et al., "Adoptive Immunotherapy of Multiple Myeloma (MM) with Allogenic CAR T-cells Targeting CS1: Enhancement of CAR Activity Through CS1 Gene Inactivation in Effector Cells," Haematologica (2015) Jun. 100(s1):288 Abstract P724.

Mihara et al., "Synergistic and Persistent Effect of T-cell Immunotherapy with Anti-CD19 or Anti-CD38 Chimeric Receptor in Conjunction with Rituximab on B-cell non-Hodgkin Lymphoma," British Journal of Haematology (2010) 151:37-46.

\* cited by examiner

ENGINEERED CELLS FOR ADOPTIVE CELL THERAPY

CROSS-REFERENCE TO RELATED APPLICATIONS

This application is a U.S. National Stage of International Application No. PCT/US2015/040660 filed Jul. 15, 2015, which claims priority from U.S. provisional application No. 62/025,006, filed Jul. 15, 2014, the contents of these applications are incorporated by reference in their entirety.

INCORPORATION BY REFERENCE OF SEQUENCE LISTING

The present application is being filed along with a Sequence Listing in electronic format. The Sequence Listing is provided as a file entitled 735042000500seqlist.txt, created Jan. 12, 2017, which is 43 kilobytes in size. The information in the electronic format of the Sequence Listing is incorporated by reference in its entirety.

FIELD

The present disclosure relates in some aspects to engineered cells for adoptive therapy, including NK cells and T cells. In some aspects, the disclosure further relates to methods and compositions for engineering and producing the cells, compositions containing the cells, and methods for their administration to subjects. In some aspects, features of the cells and methods provide specificity and/or efficacy. In some embodiments, the cells contain genetically engineered antigen receptors that specifically bind to antigens, such as chimeric antigen receptors (CARs) and costimulatory receptors. In some embodiments, the cells include receptors targeting multiple antigens. In some embodiments, the cells include repression of one or more gene product, for example, by disruption of a gene encoding the gene product. In some embodiments, a gene encoding an antigen recognized by the engineered antigen receptor is disrupted, reducing the likelihood of targeting of the engineered cells.

BACKGROUND

Various strategies are available for producing and administering engineered cells for adoptive therapy. For example, strategies are available for engineering immune cells expressing genetically engineered antigen receptors, such as CARs, and for suppression or repression of gene expression in the cells. Improved strategies are needed, for example, to provide a wider range of target antigens and diseases that may be treated using such cells, to improve specificity or selectivity of the cells, e.g., to avoid off-target effects, and to improve efficacy of the cells, for example, by avoiding suppression of effector functions and improving the activity and/or survival of the cells upon administration to subjects. Provided are methods, cells, compositions, kits, and systems that meet such needs.

SUMMARY

Provided are cells, including engineered cells, such as engineered immune or immunostimulatory cells, as well as methods for producing and using the cells, such as in adoptive therapy, and compositions, such as pharmaceutical compositions, containing the cells. Among the cells are those having one or more features, such as dual-antigen targeting features and/or gene disruptions, which on their own or collectively provide improved safety, specificity, selectivity, and/or efficacy, and/or allow for the targeting of a broader range of antigens or diseases by adoptive cell therapy.

In some embodiments, the cells are engineered immune cells including: a genetically engineered antigen receptor that specifically binds to a target antigen; and a disruption in a gene encoding the target antigen, said disruption resulting in reduced expression of the target antigen in the engineered immune cell. In some aspects, the target antigen is an antigen expressed on the surface of resting T cells, activated T cells, or both. In some aspects, the target antigen is expressed on the cell surface in a cancer, such as a hematologic cancer, an immune cancer, a leukemia, a lymphoma, and/or a myeloma, such as multiple myeloma.

In some aspects, such as where the antigen receptor induces an activating signal or one that causes an immune response directed at cells expressing the target antigen, the target antigen is one that is expressed on a disease or condition to be treated, such as cancer but that also is ordinarily expressed on the cell being engineered or sued for adoptive cell therapy. In some aspects, that target antigen is a universal tumor antigen, in some aspects one that is expressed naturally on or in the engineered cells and/or expressed on or in or the expression of which is upregulated on or in, activated T cells. In some aspects, the universal tumor antigen is a human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53 or cyclin (D1). For example, the target antigen is hTERT or survivin. In some aspects, the target antigen is CD38. In other aspects, the target antigen is CD33 or TIM-3. In other aspects, it is CD26, CD30, CD53, CD92, CD100, CD148, CD150, CD200, CD261, CD262, or CD362.

In some aspects, such as where the receptor induces a suppressive or inhibitory, e.g., immunosuppressive, signal, the antigen is one that is not expressed in the disease or condition. In some aspects, wherein the genetically engineered antigen receptor is capable of inducing an inhibitory or immunosuppressive or repressive signal to the cell upon recognition of the target antigen. In some aspects, the antigen is an antigen that is not expressed on the surface of a cancer cell or infected cell or the expression of which is downregulated on a cancer cell or an infected cell. Exemplary of such antigens are MHC-class I molecules.

In some embodiments, the antigen is a gene product that is naturally expressed in the cell type of the engineered cell. In some embodiments, expression of the target antigen in the engineered immune cell is reduced by at least 50, 60, 70, 80, 90, or 95% as compared to the expression in the immune cell in the absence of said gene disruption. In some embodiments, the disruption comprises a deletion of at least a portion of at least one exon of the gene; comprises a deletion, mutation, and/or insertion in the gene resulting in the presence of a premature stop codon in the gene; and/or comprises a deletion, mutation, and/or insertion within a first or second exon of the gene.

Among the cell types are T cells, NK cells, CD4+ T cells, CD8+ T cells, and stem cells, such as an induced pluripotent stem cell (iPS cell).

In some embodiments, the genetically engineered antigen receptor is capable of inducing an activating signal to the cell. In some aspects, the genetically engineered antigen receptor comprises an intracellular domain with an ITAM-containing motif. In some aspects, the genetically engineered antigen receptor is a T cell receptor (TCR) or a functional non-TCR antigen recognition receptor. In some aspects, it is a chimeric antigen receptor (CAR), such as an activating or stimulatory CAR, an inhibitory CAR and/or a costimulatory CAR. Among the CARs are those with an extracellular antigen-recognition domain that specifically binds to the target antigen and an intracellular signaling domain comprising an ITAM, such as an intracellular domain of a CD3-zeta (CD3ζ) chain those that further comprise a costimulatory signaling region, such as a signaling domain of CD28 or 41BB. In some aspects, the CAR comprises an extracellular antigen-recognition domain that specifically binds to the target antigen and an intracellular signaling domain that comprises a signaling portion of an immune checkpoint molecule, such as PD-1 or CTLA4.

In some aspects, the cell comprises another genetically engineered antigen receptor, such as a costimulatory receptor, such as a chimeric costimulatory receptor, that specifically binds to another antigen and is capable of inducing a costimulatory signal to the cell. In some aspects, such another target antigen and the first target antigen recognized by the first receptor are distinct. In some embodiments, at least one of such antigens is selected from among a human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53 or cyclin (D1), and the other is another antigen expressed on a tumor or cancer, and in some cases is expressed on a particular type of tumor or cancer, and not on one or more certain other types of cancers. In some aspects, such other antigen is a multiple myeloma-associated or multiple myeloma-specific antigen such as CD38 or CD138 or BCMA or CS-1; in some aspects, such other antigen is expressed on one or more blood cancers or one or more solid tumor types. In some aspects, the target antigen and said another antigen are distinct and are selected, individually, from the group consisting of CD38 and CD138. In some such aspects, the cell further comprises an additional genetically engineered antigen receptor which recognizes an antigen expressed on a disease or condition to be treated and induces a stimulatory or activating signal, which is dampened by the first genetically engineered antigen receptor.

Also provided are methods for producing the cells and cells produced by such methods. In some embodiments, the methods are carried out by (a) introducing into an immune cell a genetically engineered antigen receptor that specifically binds to a target antigen; and (b) effecting repression of expression of the target antigen in the immune cell, thereby producing a genetically engineered immune cell in which expression of the target antigen is repressed. In some aspects, steps (a) and (b) are carried out simultaneously or sequentially in any order.

In some embodiments, the effecting in (b) comprises disrupting a gene encoding the target antigen, the disruption comprises disrupting the gene at the DNA level and/or the disruption is not reversible; and/or the disruption is not transient. In some aspects, the disruption comprises introducing into the immune cell a DNA binding protein or DNA-binding nucleic acid that specifically binds to or hybridizes to the gene.

In some embodiments, the disruption comprises introducing: (a) a fusion protein comprising a DNA-targeting protein and a nuclease or (b) an RNA-guided nuclease. For example, in some embodiments, the DNA-targeting protein or RNA-guided nuclease comprises a zinc finger protein (ZFP), a TAL protein, or a clustered regularly interspaced short palindromic nucleic acid (CRISPR) specific for the gene. In some embodiments, the disruption comprises introducing a zinc finger nuclease (ZFN), a TAL-effector nuclease (TALEN), or and a CRISPR-Cas9 combination that specifically binds to, recognizes, or hybridizes to the gene. In some embodiments, the introducing is carried out by introducing into the cell a nucleic acid comprising a sequence encoding the DNA-binding protein, DNA-binding nucleotide, and/or complex comprising the DNA-binding protein or DNA-binding nucleotide. In some embodiments, the nucleic acid is a viral vector.

In some embodiments, the specific binding to the gene is within an exon of the gene and/or is within a portion of the gene encoding an N-terminus of the target antigen. In some embodiments, the introduction thereby effects a frameshift mutation in the gene and/or an insertion of an early stop codon within the coding region of the gene.

In some embodiments, the methods further include (c) introducing another genetically engineered antigen receptor, which is a chimeric costimulatory receptor that specifically binds to another antigen and is capable of inducing a costimulatory signal to the cell, wherein steps (a), (b) and (c) are carried out simultaneously or sequentially in any order. Also provided are cells produced by the methods.

In some embodiments, the engineered cells comprise: (a) a first genetically engineered antigen receptor, which specifically binds to a first antigen and is capable of inducing an activating signal to the cell; and (b) a second genetically engineered antigen receptor, which is a costimulatory receptor such as a chimeric costimulatory receptor that specifically binds to a second antigen and is capable of inducing a costimulatory signal to the cell (such as one that is necessary for full activation of the cell or a particular effector function thereof following binding of the first receptor to its antigen). In some such embodiments, the first and second antigens are distinct and, at least one is selected from the group consisting of human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53 and cyclin (D1). The other of the first second antigen can be a different antigen from any of hTERT, survivin, MDM2, CYP1B, HER2/neu, WT1, livin, AFP, CEA, MUC16, MUC1, PSMA, p53 or cyclin (D1), or can be another tumor antigen.

In some embodiments, the engineered cells comprise: (a) a first genetically engineered antigen receptor, which specifically binds to a first antigen and is capable of inducing an activating signal to the cell; and (b) a second genetically engineered antigen receptor, which is a costimulatory receptor such as a chimeric costimulatory receptor that specifically binds to a second antigen and is capable of inducing a costimulatory signal to the cell (such as one that is necessary for full activation of the cell or a particular effector function thereof following binding of the first receptor to its antigen). In some such embodiments, the first and second antigens are distinct and, individually, are selected from the group consisting of CD38, CS-1, and CD138.

In some embodiments, the engineered cell comprises (a) a first genetically engineered antigen receptor, which specifically binds to a first antigen and is capable of inducing an activating signal to the cell; and (b) a second genetically engineered antigen receptor, which is a chimeric costimulatory receptor that specifically binds to a second antigen and is capable of inducing a costimulatory signal to the cell, wherein the first and second antigens are distinct and, individually, are selected from the group consisting of CD38 and CD138.

In some embodiments, the engineered immune cell comprises (a) a first genetically engineered antigen receptor that specifically binds to a first antigen and is capable of inducing an activating signal to the cell; and (b) a second genetically engineered antigen receptor which is a chimeric costimulatory receptor that specifically binds to a second antigen and is capable of inducing a costimulatory signal to the cell, wherein the first and second antigens are distinct and the first or the second antigen is CS-1.

In some embodiments, the second antigen is an antigen expressed in multiple myeloma.

In some embodiments, the first genetically engineered antigen receptor comprises an ITAM-containing sequence, the first genetically engineered antigen receptor comprises an intracellular signaling domain of a CD3-zeta (CD3ζ) chain, and/or the first genetically engineered antigen receptor does not comprise a signaling domain from a T cell costimulatory molecule, such as one having an intracellular signaling domain of a T cell costimulatory molecule, such one or more molecules selected from the group consisting of CD28 and 41BB.

In some aspects, (a) the first antigen is CD38 and the second antigen is CD138; (b)) the first antigen is CD38 and the second antigen is CS-1; (c) the first antigen is CD138 and the second antigen is CD38; (d) the first antigen is CD138 and the second antigen is CS-1; (e) the first antigen is CS-1 and the second antigen is CD38; or (f) the first antigen is CS-1 and the second antigen is CD138. In some cases, the cell further comprises a third genetically engineered antigen receptor recognizing a third antigen.

In some aspects, the first genetically engineered antigen receptor contains an extracellular antigen recognition domain which specifically binds to the first target antigen at a dissociation constant ($K_D$) of at least $10^{-8}$ M, at least $10^{-7}$ M, at least $10^{-6}$ M, at least $10^{-5}$ M, $10^{-5}$ M, or $10^{-4}$ M. In some aspects, ligation of the first genetically engineered antigen receptor and ligation of the second genetically engineered antigen receptor induces a response in the cell, which response is not induced by ligation of either of the genetically engineered antigen receptors alone.

In some embodiments, the response is selected from the group consisting of proliferation, secretion of a cytokine, and cytotoxic activity. In some embodiments, the cell further comprising a disruption in a gene encoding the first antigen, and/or in a gene encoding the second antigen, said disruption resulting in reduced expression of the first and/or second antigen in the engineered immune cell, such as by disruption as described herein, for example, where the disrupted gene encodes CD38.

Also provided are compositions, including pharmaceutical compositions comprising the cells, and in some aspects, a carrier, such as a pharmaceutically acceptable carrier. The disease sand conditions include cancers and infectious diseases, such as hematological cancers, leukemias, lymphomas, and multiple myeloma.

DETAILED DESCRIPTION

I. Compositions and Methods Providing Specificity and/or Efficacy in Adoptive Cell Therapy Provided are cells for adoptive cell therapy, e.g., adoptive immunotherapy. The cells include immune cells such as T cells and NK cells, and generally express genetically engineered antigen receptors such as engineered TCRs and/or chimeric antigen receptors (CARs). Also provided are methods and uses of the cells, such as in adoptive therapy in the treatment of cancers including multiple myeloma (MM). Also provided are methods for engineering, preparing, and producing the cells, compositions containing the cells, and kits and devices containing and for using, producing and administering the cells. In some embodiments, the embodiments provide improved selectivity, specificity, and/or efficacy of antigen-specific adoptive cell therapy, and/or expand the scope of diseases, conditions, and/or target antigens which may be targeted via adoptive cell therapy.

The cells generally are engineered by introducing one or more genetically engineered nucleic acid or product thereof. Among such products are genetically engineered antigen receptors, including engineered T cell receptors (TCRs) and functional non-TCR antigen receptors, such as chimeric antigen receptors (CARs), including activating, stimulatory, and costimulatory CARs, and combinations thereof.

Also among the cells are those in which certain genes have been disrupted, including genes encoding the antigen recognized by a chimeric antigen receptor (CAR) or other engineered antigen receptors expressed by the cells. In some embodiments, the gene repressed is a gene encoding an antigen targeted by the genetically engineered antigen receptor, such as an activating, inhibitory, or costimulatory CAR. Thus, also provided are nucleic acids effecting repression of expression and/or disruption of endogenous genes, such as by gene editing. Also provided are cells with reduced expression of a gene or genes and methods for effecting the repression.

In some embodiments, for example, in the context of an activating or costimulatory antigen receptor, e.g., activating CAR or costimulatory CAR, the repression of a gene that encodes an antigen expressed in the engineered cells avoids or reduces the likelihood of the engineered cells themselves being targeted for killing or inhibition, thereby improving efficacy of, and/or persistence or expansion of cells in, the adoptive cell therapy. Thus, in some aspects, such disruption avoids or reduces the likelihood of targeting, by the engineered cells, of the engineered cells themselves.

For example, antigen-specific cells, such as antigen-specific T cells, targeting antigens also expressed by such cells, can induce fratricide killing of the cells. In some cases, fratricide killing of T cells is observed in cultures of antigen-specific T cells against survivin, hTERT, p53 and others, which are protein antigens expressed in activated T cells (Turksma et al. (2013) *Journal of Translational Medicine*, 11:152; Leisegang et al. (2010) *J Clin. Invest.*, 120:3869-3877; Chen et al. (2007) *Cancer Biol Ther.*, 6:1991-1996; Theoret et al. (2008) *Hum Gene Ther.*, 19:1219-1232). Methods of detecting fratricide, such as self-killing, of the immune cells can include, for example, methods in which T cells genetically engineered with an antigen receptor (e.g. TCR or CAR or other antigen receptor) are cultured in vitro, e.g., for up to 2 weeks, and monitored over time using any of a variety of assays for cell proliferation, viability and/or cytotoxicity. In some cases, the cultured cells can be stained with 7-AAD or other staining or other reagent used to discriminate viability and cell death or apoptosis or activation of apoptotic pathways. In some examples, cytotoxicity induced by fratricide killing of antigen-specific immune cells can be assessed using a cytotoxicity assay, such as an assay to assess chromium release. In some cases, the self-killing of the immune cells themselves expressing the genetically engineered antigen receptor can limit methods of using certain antigen-specific immune cells in adoptive cell therapy, since such cells can be eliminated by the fratricide killing ex vivo prior to administration and/or are upon administration in vivo. Self-killing of engineered cells within a population may be by killing of a single cell within such population of engineered cells by the same cell or by cells within the population killing one another.

Provided are cells and methods that overcome such problems. For example, in some embodiments, the expression of a gene encoding an antigen specifically bound by one or more of the genetically engineered antigen receptors is repressed in the cell. By repressing the specific antigen in the immune cell, fratricide killing of the immune cells themselves is prevented or reduced. In some embodiments, the fratricide killing (e.g. as assessed by a proliferation, viability and/or cytotoxicity assay) is reduced by at least 40%, 50%, 60%, 70%, 80%, 90%, 95% or more, such as as compared to a cell or cell population in which the cells express the engineered antigen receptor but in which the gene or antigen targeted thereby or expression thereof has not been disrupted. Such features in some aspects confer improved specificity and/or efficacy in the context of adoptive cell therapy.

Among such antigens are those expressed in cancers of the immune system, such as leukemias, lymphomas, and/or myelomas, such as multiple myeloma, and/or expressed on T cells and/or NK cells, including activated T cells. Exemplary antigens are those expressed on activated or stimulated T cells or NK cells, and subsets thereof, particularly activated cells produced by stimulatory conditions used to promote the introduction of the nucleic acid encoding the CAR or other engineered receptor. For example, among such antigens are those not generally expressed on resting T cells but expression of which is induced upon T cell activation and/or that are expressed on activated T cells. In some embodiments, the gene encodes a universal tumor antigen, such as hTERT, survivin, MDM2, CYP1B, HER2/neu, WT1, livin, AFP, CEA, MUC16, MUC1, PSMA, p53 or cyclin (D1). For example, the gene encodes hTERT or survivin. In some embodiments the gene encodes the antigen CD38. In some embodiments, the gene encodes the antigen CD33 or TIM-3; in some embodiments, it encodes the antigen CD26, CD30, CD53, CD92, CD100, CD148, CD150, CD200, CD261, CD262, or CD362.

In some embodiments, the repression is effected via disruption of the gene encoding the antigen, such as by deletion, e.g., deletion of an entire gene, exon, or region, and/or replacement with an exogenous sequence, and/or by mutation, e.g., frameshift or missense mutation, within the gene, typically within an exon of the gene. In some embodiments, the disruption results in a premature stop codon being incorporated into the gene, such that the antigen is not expressed or is not expressed in a form that is recognized by the antigen receptor. The disruption is generally carried out at the DNA level. The disruption generally is permanent, irreversible, or not transient. In other embodiments, transient or reversible repression strategies are used, such as gene knockdown using RNAi. In some embodiments, by disrupting or otherwise repressing expression of the antigen on the engineered cells, the methods and compositions provided here avoid or reduce the likelihood of killing of the engineered cells by the engineered cells themselves, thereby promoting efficacy.

In some embodiments, the cells include features for increased efficacy of the cells and methods are provided by the disruption of gene expression in the engineered cells. In some aspects, the gene disrupted encodes a checkpoint molecule, immunosuppressive molecule, such as a receptor that delivers an immunosuppressive signal to the cell, and/or any molecule which could reduce the robustness of the response of the engineered cell, for example, following administration in connection with immunotherapy.

In some embodiments, for example, in the context of an antigen that is recognized by an inhibitory CAR, the gene disruption prevents or reduces the likelihood of the inhibitory CAR expressed by the engineered cell of itself binding to a molecule also expressed by the engineered cells, thereby inducing a dampening effect on the signaling or targeted immune response by the engineered cells. Exemplary of such antigens are those expressed on normal or non-targeted or off-target cells (such that an inhibitory CAR molecule is included to prevent off-target effects), but is also expressed on the cell type used for genetic engineering, such as the T cell or NK cell. Exemplary antigens are MHC molecules, such as MHC-class I molecules, which can in some cases be downregulated in the context of immune evasion, cancer, or infection, but are generally expressed on nucleated cells. Other examples are any inhibitory CAR target that is also expressed on a T cell, NK cell, or other cell engineered for cell therapy.

In other embodiments, the gene or genes disrupted is a gene other than that encoding the antigen, such as a gene encoding an immunosuppressive molecule, e.g., checkpoint molecule or adenosine receptor, e.g., A2AR.

In some aspects, the disruption is carried out by gene editing, such as using a DNA binding protein or DNA-binding nucleic acid, which specifically binds to or hybridizes to the gene at a region targeted for disruption. In some aspects, the protein or nucleic acid is coupled to or complexed with a nuclease, such as in a chimeric or fusion protein. For example, in some embodiments, the disruption is effected using a fusion comprising a DNA-targeting protein and a nuclease, such as a Zinc Finger Nuclease (ZFN) or TAL-effector nuclease (TALEN), or an RNA-guided nuclease such as a clustered regularly interspersed short palindromic nucleic acid (CRISPR)-Cas system, such as CRISPR-Cas9 system, specific for the gene being disrupted.

In some embodiments, improved selectivity and specificity is achieved through strategies targeting multiple antigens. Such strategies generally involve multiple antigen-binding domains, which typically are present on distinct genetically engineered antigen receptors and specifically bind to distinct antigens. Thus, in some embodiments, the cells are engineered with the ability to bind more than one antigen. In some aspects, a plurality of genetically engineered antigen receptors are introduced into the cell, which specifically bind to different antigens, each expressed in or on the disease or condition to be targeted with the cells or tissues or cells thereof. Such features can in some aspects address or reduce the likelihood of off-target effects. For example, where a single antigen expressed in a disease or condition is also expressed on or in non-diseased or normal cells, such multi-targeting approaches can provide selectivity for desired cell types by requiring binding via multiple antigen receptors in order to activate the cell or induce a particular effector function.

In some embodiments, the cell expresses a first genetically engineered antigen receptor recognizing a first antigen and a second genetically engineered antigen receptor, such as a costimulatory receptor, recognizing a second antigen; in some embodiments, additional receptors recognize third, or more antigens. In some aspects, each of the antigens is expressed in the context of a target cell, disease, or condition, such as in a neoplasia, cancer, malignancy, or infectious disease. In some aspects, one or more of the antigens is also expressed on cells or in tissues or environments which it is not desired to target with the cell therapy, such as in normal or non-diseased tissue. In some embodiments, the presence of multiple receptors and/or multiple antigen-recognition components avoids or reduces the likelihood of off-target effects on such tissues, cells, or environments. Thus, in some aspects, features of the provided cells and methods avoid or reduce the likelihood of inappropriate activation or response of cells directed at cells, tissues, or environments other than those being targeted by the cell therapy. For example, in some embodiments, they avoid or reduce the likelihood of off-target effects.

In some aspects, at least one of the genetically engineered antigen receptor is specific for a target antigen that is a universal tumor antigen expressed on more than one type of tumor. For example, among the cells are those targeting multiple antigens where at least one of the targeted antigens is hTERT, survivin, MDM2, CYP1B, HER2/neu, WT1, livin, AFP, CEA, MUC16, MUC1, PSMA, p53 or cyclin (D1). In some embodiments, the one or other antigens targeted by one or more other genetically engineered antigen receptors on the cells is one that is expressed on a tumor or cancer.

In some aspects, the disease or condition is multiple myeloma, the target cell is a multiple myeloma cell, and/or the target antigens are antigens expressed in multiple myeloma. Among the cells are those targeting multiple antigens, such multiple antigens expressed in a disease or condition such as multiple myeloma, such as combinations of CD38, CD138 and/or CS-1. Exemplary combinations of antigens to be targeted include two or more of CD38, CD138, and/or CS-1. In some aspects, the cells recognize two or more antigens expressed in multiple myeloma, one or more of which may also be expressed on normal or non-cancerous cells. In some embodiments, the antigens include two or more of CD38, CD138, and CS-1.

In some embodiments, the multiple antigen-recognition domains or multiple antigen receptors are designed or engineered such that a response is induced in the cell only upon specific binding or ligation of the plurality of receptors or antigen-recognition domains, and not upon ligation or binding to antigen by a single receptor or domain alone. In some aspects, the first receptor includes an activation domain, such as an ITAM-containing motif, such as an immunostimulatory domain of a CD3-zeta chain. In some aspects, the second receptor is a costimulatory receptor, which does not include such an activation domain but includes a costimulatory domain, e.g., which enhances the signal induced by ligation of the first receptor. In some aspects, the normal cells also express or can express the antigen recognized by the activating receptor.

In some embodiments, the cell includes multiple genetically engineered antigen receptors recognizing different antigens and also includes a gene disruption, for example, disruption in a gene encoding the antigen targeted by one or more of the antigen receptors. In some embodiments, the gene disruption is carried out prior to the introduction of the antigen receptor(s); in some embodiments, it is carried out simultaneously to introduction of the antigen receptor(s). In some aspects, the introduction of the antigen receptor(s) effects the gene disruption, such as by insertion into the disrupted gene locus by homologous recombination.

Also provided are methods, compounds, and compositions for producing the engineered cells. Provided are methods for cell isolation, genetic engineering and gene disruption. Provided are nucleic acids, such as constructs, e.g., viral vectors encoding the genetically engineered antigen receptors and/or encoding nucleic acids and/or proteins for targeted gene disruption, and methods for introducing such nucleic acids into the cells, such as by transduction. Also provided are compositions containing the engineered cells, and methods, kits, and devices for administering the cells and compositions to subjects, such as for adoptive cell therapy. In some aspects, the cells are isolated from a subject, engineered, and administered to the same subject. In other aspects, they are isolated from one subject, engineered, and administered to another subject.

A. Cells, Cell Preparation and Culture

In some embodiments, the cells, e.g., engineered cells, are eukaryotic cells, such as mammalian cells, e.g., human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). In some aspects, the cells are human cells. The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, one or more of the T cell populations is enriched for or depleted of cells that are positive for (marker$^+$) or express high levels (marker$^{high}$) of one or more particular markers, such as surface markers, or that are negative for (marker$^-$) or express relatively low levels (marker$^{low}$) of one or more markers. In some cases, such markers are those that are absent or expressed at relatively low levels on certain populations of T cells (such as non-memory cells) but are present or expressed at relatively higher levels on certain other populations of T cells (such as memory cells). In one embodiment, the cells (such as the CD8$^+$ cells or the T cells, e.g., CD3$^+$ cells) are enriched for (i.e., positively selected for) cells that are positive or expressing high surface levels of CD45RO, CCR7, CD28, CD27, CD44, CD127, and/or CD62L and/or depleted of (e.g., negatively selected for) cells that are positive for or express high surface levels of CD45RA. In some embodiments, cells are enriched for or depleted of cells positive or expressing high surface levels of CD122, CD95, CD25, CD27, and/or IL7-Rα (CD127). In some examples, CD8+ T cells are enriched for cells positive for CD45RO (or negative for CD45RA) and for CD62L.

In some embodiments, a CD4+ T cell population and a CD8+ T cell sub-population, e.g., a sub-population enriched for central memory ($T_{CM}$) cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

Cell Preparation

The cells and compositions containing the cells for engineering typically are isolated from a sample, such as a biological sample, e.g., one obtained from or derived from a subject. In some embodiments, the subject from which the cell is isolated as one having a particular disease or condition or in need of a cell therapy or to which cell therapy will be administered. The subject in some embodiments is a mammal, such as a human, such as a subject in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig.

Cell Processing, Preparation, and Non-Affinity-Based Separation

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

Separation Based on Affinity and/or Marker Profile

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques.

For example, $CD3^+$, $CD28^+$ T cells can be positively selected using CD3/CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed ($marker^+$) at a relatively higher level ($marker^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, $CD8^+$ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) *J Immunother.* 35 (9):689-701. In some embodiments, combining $T_{CM}$-enriched $CD8^+$ T cells and $CD4^+$ T cells further enhances efficacy.

In embodiments, memory T cells are present in both $CD62L^+$ and CD62L– subsets of $CD8^+$ peripheral blood lymphocytes. PBMC can be enriched for or depleted of $CD62L-CD8^+$ and/or $CD62L^+CD8^+$ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a $CD8^+$ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the $CD8^+$ cell population or subpopulation, also is used to generate the $CD4^+$ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of $CD4^+$ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

$CD4^+$ T helper cells are sorted into naïve, central memory, and effector cells by identifying cell populations that have cell surface antigens. $CD4^+$ lymphocytes can be obtained by standard methods. In some embodiments, naive $CD4^+$ T lymphocytes are $CD45RO^-$, $CD45RA^+$, $CD62L^+$, $CD4^+$ T cells. In some embodiments, central memory $CD4^+$ cells are $CD62L^+$ and $CD45RO^+$. In some embodiments, effector $CD4^+$ cells are $CD62L^-$ and $CD45RO^-$.

In one example, to enrich for $CD4^+$ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher© Humana Press Inc., Totowa, N.J.).

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the affinity-based selection is via magnetic-activated cell sorting (MACS) (Miltenyi Biotech, Auburn, Calif.). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotic), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35 (9): 651-660, Terakura et al. (2012) Blood. 1:72-82, and Wang et al. (2012) *J Immunother.* 35 (9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) J Biophoton. 1 (5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

Cryopreservation

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80° C. at a rate of 1° per minute and stored in the vapor phase of a liquid nitrogen storage tank.

In some embodiments, the provided methods include cultivation, incubation, culture, and/or genetic engineering steps. For example, in some embodiments, provided are methods for incubating and/or engineering the depleted cell populations and culture-initiating compositions.

Thus, in some embodiments, the cell populations are incubated in a culture-initiating composition. The incubation and/or engineering may be carried out in a culture vessel, such as a unit, chamber, well, column, tube, tubing set, valve, vial, culture dish, bag, or other container for culture or cultivating cells.

Incubation and Culture

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a genetically engineered antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include 1L-2 and/or IL-15, for example, an IL-2 concentration of at least about 10 units/mL.

In some aspects, incubation is carried out in accordance with techniques such as those described in U.S. Pat. No. 6,040,177 to Riddell et al., Klebanoff et al. (2012) J Immunother. 35 (9): 651-660, Terakura et al. (2012) Blood. 1:72-82, and/or Wang et al. (2012) J Immunother. 35 (9): 689-701.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

In some aspects, the methods include assessing expression of one or more markers on the surface of the engineered cells or cells being engineered. In one embodiment, the methods include assessing surface expression of one or more target antigen (e.g., antigen recognized by the genetically engineered antigen receptor) sought to be targeted by the adoptive cell therapy, for example, by affinity-based detection methods such as by flow cytometry. In some aspects, where the method reveals surface expression of the antigen or other marker, the gene encoding the antigen or other marker is disrupted or expression otherwise repressed for example, using the methods described herein.

B. Genetically Engineered Antigen Receptors

In some embodiments, the cells comprise one or more nucleic acids introduced via genetic engineering that encode one or more antigen receptors, and genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

Among the genetically engineered products are genetically engineered antigen receptors. Among such antigen receptors are genetically engineered T cell receptors (TCRs) and components thereof, and functional non-TCR antigen receptors, such as chimeric antigen receptors (CAR), including chimeric activating receptors and chimeric costimulatory receptors. In some embodiments, the CAR contains an extracellular antigen-recognition domain that specifically binds to an antigen. In some embodiments, the antigen is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Exemplary antigen receptors, including CARs and recombinant TCRs, as well as methods for engineering and introducing the receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3 (4): 388-398; Davila et al. (2013) *PLoS ONE* 8 (4): e61338; Turtle et al., *Curr. Opin. Immunol.*, 2012 October; 24 (5): 633-39; Wu et al., *Cancer,* 2012 Mar. 18 (2): 160-75. In some aspects, the genetically engineered antigen receptors include a CAR as described in U.S. Pat. No. 7,446,190, and those described in International Patent Application Publication No.: WO/2014055668 A1.

Chimeric Antigen Receptors (CARs)

In some embodiments, the engineered antigen receptors include chimeric antigen receptors (CARs), including activating or stimulatory CARs, costimulatory CARs (see WO2014/055668), and/or inhibitory CARs (iCARs, see Fedorov et al., *Sci. Transl. Medicine,* 5 (215) (December, 2013). The CARs generally include an extracellular antigen (or ligand) binding domain linked to one or more intracellular signaling components, in some aspects via linkers and/or transmembrane domain(s). Such molecules typically mimic or approximate a signal through a natural antigen receptor, a signal through such a receptor in combination with a costimulatory receptor, and/or a signal through a costimulatory receptor alone.

In some embodiments, CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb).

The term "antibody" herein is used in the broadest sense and includes polyclonal and monoclonal antibodies, including intact antibodies and functional (antigen-binding) antibody fragments, including fragment antigen binding (Fab) fragments, F(ab')$_2$ fragments, Fab' fragments, Fv fragments, recombinant IgG (rIgG) fragments, variable heavy chain ($V_H$) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

In some embodiments, the antigen-binding proteins, antibodies and antigen binding fragments thereof specifically recognize an antigen of a full-length antibody. In some embodiments, the heavy and light chains of an antibody can be full-length or can be an antigen-binding portion (a Fab, F(ab')2, Fv or a single chain Fv fragment (scFv)). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; variable heavy chain ($V_H$) regions, single-chain antibody molecules such as scFvs and single-domain $V_H$ single antibodies; and multispecific antibodies formed from antibody fragments. In particular embodiments, the antibodies are single-chain antibody fragments comprising a variable heavy chain region and/or a variable light chain region, such as scFvs.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

Single-domain antibodies are antibody fragments comprising all or a portion of the heavy chain variable domain or all or a portion of the light chain variable domain of an antibody. In certain embodiments, a single-domain antibody is a human single-domain antibody. In some embodiments, the CAR comprises an antibody heavy chain domain that specifically binds the antigen, such as a cancer marker or cell surface antigen of a cell or disease to be targeted, such as a tumor cell or a cancer cell, such as any of the target antigens described herein or known in the art.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some aspects, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

In some embodiments, the CAR contains an antibody or an antigen-binding fragment (e.g. scFv) that specifically recognizes an antigen, such as an intact antigen, expressed on the surface of a cell.

In some embodiments, the CAR contains a TCR-like antibody, such as an antibody or an antigen-binding fragment (e.g. scFv) that specifically recognizes an intracellular antigen, such as a tumor-associated antigen, presented on the cell surface as a MHC-peptide complex. In some embodiments, an antibody or antigen-binding portion thereof that recognizes an MHC-peptide complex can be expressed on cells as part of a recombinant receptor, such as an antigen receptor. Among the antigen receptors are functional non-TCR antigen receptors, such as chimeric antigen receptors (CARs). Generally, a CAR containing an antibody or antigen-binding fragment that exhibits TCR-like specificity directed against peptide-MHC complexes also may be referred to as a TCR-like CAR.

Reference to "Major histocompatibility complex" (MHC) refers to a protein, generally a glycoprotein, that contains a polymorphic peptide binding site or binding groove that can, in some cases, complex with peptide antigens of polypeptides, including peptide antigens processed by the cell machinery. In some cases, MHC molecules can be displayed or expressed on the cell surface, including as a complex with peptide, i.e. MHC-peptide complex, for presentation of an antigen in a conformation recognizable by an antigen receptor on T cells, such as a TCRs or TCR-like antibody. Generally, MHC class I molecules are heterodimers having a membrane spanning a chain, in some cases with three a domains, and a non-covalently associated β2 microglobulin. Generally, MHC class II molecules are composed of two transmembrane glycoproteins, α and β, both of which typically span the membrane. An MHC molecule can include an effective portion of an MHC that contains an antigen binding site or sites for binding a peptide and the sequences necessary for recognition by the appropriate antigen receptor. In some embodiments, MHC class I molecules deliver peptides originating in the cytosol to the cell surface, where a MHC-peptide complex is recognized by T cells, such as generally $CD8^+$ T cells, but in some cases CD4+ T cells. In some embodiments, MHC class II molecules deliver peptides originating in the vesicular system to the cell surface, where they are typically recognized by $CD4^+$ T cells. Generally, MHC molecules are encoded by a group of linked loci, which are collectively termed H-2 in the mouse and human leukocyte antigen (HLA) in humans. Hence, typically human MHC can also be referred to as human leukocyte antigen (HLA).

The term "MHC-peptide complex" or "peptide-MHC complex" or variations thereof, refers to a complex or association of a peptide antigen and an MHC molecule, such as, generally, by non-covalent interactions of the peptide in the binding groove or cleft of the MHC molecule. In some embodiments, the MHC-peptide complex is present or displayed on the surface of cells. In some embodiments, the MHC-peptide complex can be specifically recognized by an antigen receptor, such as a TCR, TCR-like CAR or antigen-binding portions thereof.

The term "peptide antigen" or "peptide epitope" refers to a peptide of a polypeptide that can associate with an MHC molecule, such as for recognition by an antigen receptor. Generally, the peptide is derived from or based on a fragment of a longer biological molecule, such as a polypeptide or protein. In some embodiments, the peptide typically is about 8 to about 24 amino acids in length. In some embodiments, a peptide has a length of from or from about 9 to 22 amino acids for recognition in the MHC Class II complex. In some embodiments, a peptide has a length of from or from about 8 to 13 amino acids for recognition in the MHC Class I complex. In some embodiments, upon recognition of the peptide in the context of an MHC molecule, such as MHC-peptide complex, the antigen receptor, such as TCR or TCR-like CAR, produces or triggers an activation signal to the T cell that induces a T cell response, such as T cell proliferation, cytokine production, a cytotoxic T cell response or other response.

In some embodiments, an antibody or antigen-binding portion thereof that specifically binds to a MHC-peptide complex, can be produced by immunizing a host with an effective amount of an immunogen containing a specific MHC-peptide complex. In some cases, the peptide of the MHC-peptide complex is an epitope of antigen capable of binding to the MHC, such as a tumor antigen, for example a universal tumor antigen, myeloma antigen or other antigen as described below. In some embodiments, an effective amount of the immunogen is then administered to a host for eliciting an immune response, wherein the immunogen retains a three-dimensional form thereof for a period of time sufficient to elicit an immune response against the three-dimensional presentation of the peptide in the binding groove of the MHC molecule. Serum collected from the host is then assayed to determine if desired antibodies that recognize a three-dimensional presentation of the peptide in the binding groove of the MHC molecule is being produced. In some embodiments, the produced antibodies can be assessed to confirm that the antibody can differentiate the MHC-peptide complex from the MHC molecule alone, the peptide of interest alone, and a complex of MHC and irrelevant peptide. The desired antibodies can then be isolated.

In some embodiments, an antibody or antigen-binding portion thereof that specifically binds to an MHC-peptide complex can be produced by employing antibody library display methods, such as phage antibody libraries. In some embodiments, phage display libraries of mutant Fab, scFV or other antibody forms can be generated, for example, in which members of the library are mutated at one or more residues of a CDR or CDRs. Exemplary of such methods are known in the art (see e.g. US published application No. US20020150914, US2014/0294841; and Cohen C J. et al. (2003) *J Mol. Recogn.* 16:324-332).

In some aspects, the antigen-specific binding, or recognition component is linked to one or more transmembrane and intracellular signaling domains. In some embodiments, the CAR includes a transmembrane domain fused to the extracellular domain of the CAR. In one embodiment, the transmembrane domain that naturally is associated with one of the domains in the CAR is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD 16, CD22, CD33, CD37, CD64, CD80, CD86, CD 134, CD137, CD 154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain.

In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The CAR generally includes at least one intracellular signaling component or components. In some embodiments, the CAR includes an intracellular component of the TCR complex, such as a TCR CD3$^+$ chain that mediates T-cell activation and cytotoxicity, e.g., CD3 zeta chain. Thus, in some aspects, the antigen binding molecule is linked to one or more cell signaling modules. In some embodiments, cell signaling modules include CD3 transmembrane domain, CD3 intracellular signaling domains, and/or other CD transmembrane domains. In some embodiments, the CAR further includes a portion of one or more additional molecules such as Fc receptor γ, CD8, CD4, CD25, or CD16. For example, in some aspects, the CAR includes a chimeric molecule between CD3-zeta (CD3-ζ) or Fc receptor γ and CD8, CD4, CD25 or CD16.

In some embodiments, upon ligation of the CAR, the cytoplasmic domain or intracellular signaling domain of the CAR activates at least one of the normal effector functions or responses of the immune cell, e.g., T cell engineered to express the cell. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule. Such truncated portion in some aspects is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal. In some aspects, the cell comprises a first CAR which contains signaling domains to induce the primary signal and a second CAR which binds to a second antigen and contains the component for generating a costimulatory signal. For example, a first CAR can be an activating CAR and the second CAR can be a costimulatory CAR. In some aspects, both CARs must be ligated in order to induce a particular effector function in the cell, which can provide specificity and selectivity for the cell type being targeted.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR zeta, FcR gamma, FcR beta, CD3 gamma, CD3 delta, CD3 epsilon, CD8, CD22, CD79a, CD79b, and CD66d. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components; in other aspects, the activating domain is provided by one CAR whereas the costimulatory component is provided by another CAR recognizing another antigen.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses two or more costimulatory domain combined with an activation domain, e.g., primary activation domain, in the cytoplasmic portion. One example is a receptor including intracellular components of CD3-zeta, CD28, and 4-1BB.

In some embodiments, the CAR or other antigen receptor further includes a marker to confirm transduction or engineering of the cell to express the receptor, such as a truncated version of a cell surface receptor, such as truncated EGFR, tEGFR).

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR in some aspects is one that include multiple costimulatory domains of different costimulatory receptors.

In some aspects, the CAR or other antigen receptor is an inhibitory CAR (e.g. iCAR) and includes intracellular components that dampen or suppress a response, such as an immune response, such as an ITAM- and/or costimulatory-promoted response in the cell. Exemplary of such intracellular signaling components are those found on immune checkpoint molecules, including PD-1, CTLA4, LAG3, BTLA, OX2R, TIM-3, TIGIT, LAIR-1, PGE2 receptors, EP2/4 Adenosine receptors including A2AR. In some aspects, the engineered cell includes an inhibitory CAR including a signaling domain of or derived from such an inhibitory molecule, such that it serves to dampen the response of the cell, for example, that induced by an activating and/or costimulatory CAR. Such CARs are used, for example, to reduce the likelihood of off-target effects in the context in which the antigen recognized by the activating receptor, e.g, CAR, is also expressed or may also be expressed on the surface of normal cells. In some aspects, an inhibitory receptor, e.g., iCAR is introduced which recognizes a marker specific to the normal cell. In some aspects, where such an antigen is also expressed on the engineered cell, the antigen is the target of gene editing or disruption approaches provided herein. In some aspects, such disruption avoids dampening of the engineered cells' response induced by the engineered cells themselves.

TCRs

In some embodiments, the genetically engineered antigen receptors include recombinant T cell receptors (TCRs) and/or TCRs cloned from naturally occurring T cells.

A "T cell receptor" or "TCR" refers to a molecule that contains a variable α and β chains (also known as TCRα and TCRβ, respectively) or a variable γ and δ chains (also known as TCRγ and TCRδ, respectively) and that is capable of specifically binding to an antigen peptide bound to a MHC receptor. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules. In some embodiments, a TCR also can contain a constant domain, a transmembrane domain and/or a short cytoplasmic tail (see, e.g., Janeway et al., *Immunobiology: The Immune System in Health and Disease*, 3$^{rd}$ Ed., Current Biology Publications, p. 4:33, 1997). For example, in some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction. Unless otherwise stated, the term "TCR" should be understood to encompass functional TCR fragments thereof. The term also encompasses intact or full-length TCRs, including TCRs in the αβ form or γδ form.

Thus, for purposes herein, reference to a TCR includes any TCR or functional fragment, such as an antigen-binding portion of a TCR that binds to a specific antigenic peptide bound in an MHC molecule, i.e. MHC-peptide complex. An "antigen-binding portion" or antigen-binding fragment" of a TCR, which can be used interchangeably, refers to a molecule that contains a portion of the structural domains of a TCR, but that binds the antigen (e.g. MHC-peptide complex) to which the full TCR binds. In some cases, an antigen-binding portion contains the variable domains of a TCR, such as variable α chain and variable β chain of a TCR, sufficient to form a binding site for binding to a specific MHC-peptide complex, such as generally where each chain contains three complementarity determining regions.

In some embodiments, the variable domains of the TCR chains associate to form loops, or complementarity determining regions (CDRs) analogous to immunoglobulins, which confer antigen recognition and determine peptide specificity by forming the binding site of the TCR molecule and determine peptide specificity. Typically, like immunoglobulins, the CDRs are separated by framework regions (FRs) (see, e.g., Jores et al., *Proc. Nat'l Acad. Sci. U.S.A.* 87:9138, 1990; Chothia et al., *EMBO J.* 7:3745, 1988; see also Lefranc et al., *Dev. Comp. Immunol.* 27:55, 2003). In some embodiments, CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. In some embodiments, the variable region of the β-chain can contain a further hypervariability (HV4) region.

In some embodiments, the TCR chains contain a constant domain. For example, like immunoglobulins, the extracellular portion of TCR chains (e.g., α-chain, β-chain) can contain two immunoglobulin domains, a variable domain (e.g., $V_\alpha$ or $V_\beta$; typically amino acids 1 to 116 based on Kabat numbering Kabat et al., "Sequences of Proteins of Immunological Interest, US Dept. Health and Human Services, Public Health Service National Institutes of Health, 1991, 5$^{th}$ ed.) at the N-terminus, and one constant domain (e.g., α-chain constant domain or C$_\alpha$, typically amino acids 117 to 259 based on Kabat, β-chain constant domain or C$_\beta$, typically amino acids 117 to 295 based on Kabat) adjacent to the cell membrane. For example, in some cases, the extracellular portion of the TCR formed by the two chains contains two membrane-proximal constant domains, and two membrane-distal variable domains containing CDRs. The constant domain of the TCR domain contains short connecting sequences in which a cysteine residue forms a disulfide bond, making a link between the two chains. In some embodiments, a TCR may have an additional cysteine residue in each of the α and β chains such that the TCR contains two disulfide bonds in the constant domains.

In some embodiments, the TCR chains can contain a transmembrane domain. In some embodiments, the transmembrane domain is positively charged. In some cases, the TCR chains contains a cytoplasmic tail. In some cases, the structure allows the TCR to associate with other molecules like CD3. For example, a TCR containing constant domains with a transmembrane region can anchor the protein in the cell membrane and associate with invariant subunits of the CD3 signaling apparatus or complex.

Generally, CD3 is a multi-protein complex that can possess three distinct chains (γ, δ, and ε) in mammals and the ζ-chain. For example, in mammals the complex can contain a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3ζ chain has three. Generally, ITAMs are involved in the signaling capacity of the TCR complex. These accessory molecules have negatively charged transmembrane regions and play a role in propagating the signal from the TCR into the cell. The CD3- and ζ-chains, together with the TCR, form what is known as the T cell receptor complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, a TCR for a target antigen (e.g., a cancer antigen) is identified and introduced into the cells. In some embodiments, nucleic acid encoding the TCR can be obtained from a variety of sources, such as by polymerase chain reaction (PCR) amplification of publicly available TCR DNA sequences. In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, a such as a high-affinity T cell clone can be isolated from a patient, and the TCR isolated. In some embodiments, the T-cells can be a cultured T-cell hybridoma or clone. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) *Clin Cancer Res.* 15:169-180 and Cohen et al. (2005) *J Immunol.* 175:5799-5808. In some embodiments, phage display is used to isolate TCRs against a target antigen (see, e.g., Varela-Rohena et al. (2008) *Nat Med.* 14:1390-1395 and Li (2005) *Nat Biotechnol.* 23:349-354. In some embodiments, the TCR or antigen-binding portion thereof can be synthetically generated from knowledge of the sequence of the TCR.

In some embodiments, after the T-cell clone is obtained, the TCR alpha and beta chains are isolated and cloned into a gene expression vector. In some embodiments, the TCR alpha and beta genes are linked via a picornavirus 2A ribosomal skip peptide so that both chains are coexpression. In some embodiments, genetic transfer of the TCR is accomplished via retroviral or lentiviral vectors, or via transposons (see, e.g., Baum et al. (2006) Molecular Therapy: The Journal of the American Society of Gene Therapy. 13:1050-1063; Frecha et al. (2010) Molecular Therapy: The Journal of the American Society of Gene Therapy. 18:1748-1757; an Hackett et al. (2010) Molecular Therapy: The Journal of the American Society of Gene Therapy. 18:674-683.

Antigens

Among the antigens targeted by the genetically engineered antigen receptors are those expressed in the context of a disease, condition, or cell type to be targeted via the adoptive cell therapy. Among the diseases and conditions are proliferative, neoplastic, and malignant diseases and disorders, including cancers and tumors, including hematologic cancers, cancers of the immune system, such as lymphomas, leukemias, and/or myelomas, such as B, T, and myeloid leukemias, lymphomas, and multiple myelomas.

In some embodiments, the antigen is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells. In some such embodiments, a multi-targeting and/or gene disruption approach as provided herein is used to improve specificity and/or efficacy.

In some embodiments, the antigen is a universal tumor antigen. The term "universal tumor antigen" refers to an immunogenic molecule, such as a protein, that is, generally, expressed at a higher level in tumor cells than in non-tumor cells and also is expressed in tumors of different origins. In some embodiments, the universal tumor antigen is expressed in more than 30%, 40%, 50%, 60%, 70%, 75%, 80%, 85%, 90% or more of human cancers. In some embodiments, the universal tumor antigen is expressed in at least three, at least four, at least five, at least six, at least seven, at least eight or more different types of tumors. In some cases, the universal tumor antigen may be expressed in non-tumor cells, such as normal cells, but at lower levels than it is expressed in tumor cells. In some cases, the universal tumor antigen is not expressed at all in non-tumor cells, such as not expressed in normal cells. Exemplary universal tumor antigens include, for example, human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53 or cyclin (D1). Peptide epitopes of tumor antigens, including universal tumor antigens, are known in the art and, in some aspects, can be used to generate MHC-restricted antigen receptors, such as TCRs or TCR-like CARs (see e.g. published PCT application No. WO2011009173 or WO2012135854 and published U.S. application No. US20140065708).

For example, in some embodiments, the antigen is hTERT. hTERT is a tumor antigen that is widely expressed in various cancers. In some aspects, hTERT has or contains a sequence of amino acids set forth in SEQ ID NO:3 (GenBank Accession No. NP_937983.2) and encoded by a sequence of nucleotides set forth in SEQ ID NO:4 (GenBank Accession No. NM_198253.2). Generally, hTERT is a reverse transcriptase that is part of the human telomerase complex, which is a complex that can maintain the telomeric ends of linear chromosomes and, in some cases, protects chromosomes from degradation and end-to-end fusion. In some aspects, hTERT expression results in teleomere synthesis from an RNA template, and its expression can correlate with telomerase activity because it is the rate-limiting component of the complex. Generally, hTERT is not expressed in most human cells, including normal cells, but is expressed or upregulated in tumors and cancer cells. For example, more than 85% of human tumors express hTERT. Thus, in some aspects, hTERT can be a universal tumor antigen. HLA-restricted peptide epitopes of hTERT are known (see e.g. U.S. Pat. No. 7,718,777, and published PCT application Nos. WO2000025813 and WO2013135553), and, in some aspects, such can be used to generate or identify antigen receptors against hTERT. Non-limiting examples of hTERT peptide epitopes include any set forth in any of SEQ ID NOS: 7-19. Antigen receptors against hTERT, such as TCR or TCR-like antibodies, have been generated and are known in the art (see e.g., U.S. Pat. No. 7,718,777 and published U.S. patent applications US20090226474 and US20030223994; see also Ugel et al. (2010) Blood, 115:1374-1384).

In some embodiments, the antigen is survivin (also called baculoviral inhibitor of apoptosis repeat-containing 5, BIRC5). In some aspects, survivin has or contains a sequence of amino acids set forth in SEQ ID NO:5 (GenBank Accession No. NP_001159) and encoded by a sequence of nucleotides set forth in SEQ ID NO:6 (GenBank Accession No. NM_001168.2). In some cases, other transcript isoforms can exist, such as that have or contain an amino acid or nucleotide sequence referenced at GenBank Accession No. NP_001012270 or NM_001012270, respectively, or NP_001012271.1 or NM_001012271.1, respectively. Generally, survivin is a member of the family of inhibitors of apoptosis proteins (IAPs). In some cases, survivin is upregulated in many types of cancers, such as lung, colon, breast, pancreas, prostate, melanoma and others, but it is not generally expressed or upregulated in normal cells or tissues. In some aspects, the expression of survivin in cancer may be related to a general role of apoptosis inhibition in tumor progression. Thus, in some aspects, survivin can be a universal tumor antigen. HLA-restricted peptide epitopes of survivn are known (see e.g. U.S. Pat. No. 7,892,559 and published U.S. patent application No. US20090004214), and, in some cases, such peptide epitopes can be used to generate or identify antigen receptors against survivin, including TCRs or TCR-like CARs. Non-limiting examples of survivin peptide epitopes include any set forth in any of SEQ ID NOS: 20-30. Antigen receptors against survivin, such as TCR or TCR-like antibodies, have been generated and are known in the art (see e.g., published PCT application No. WO2010075417).

In some aspects, the antigen is expressed on multiple myeloma, such as CD38, CD138, and/or CS-1. Other exemplary multiple myeloma antigens include CD56, TIM-3, CD33, CD123, and/or CD44. Antibodies or antigen-binding fragments directed against such antigens are known and include, for example, those described in U.S. Pat. Nos. 8,153,765; 8,603,477, 8,008,450; U.S. published application No. US20120189622; and published international PCT application Nos. WO2006099875, WO2009080829 or WO2012092612. In some embodiments, such antibodies or antigen-binding fragments thereof (e.g. scFv) can be used to generate a CAR.

In some embodiments, the antigen is a CD38 antigen that is a human CD38. In some aspects, the CD38 has or contains an amino acid sequence referenced at GenBank Accession No.: BAA18966, e.g., at BAA18966.1, or that is referenced at GI:1911103. In some aspects, it has or contains the following sequence: mancefspvs gdkpccrlsr raqlclgvsi lvlilvvvla vvvprwrqqw sgpgttkrfp etvlarcvky teihpemrhv dcqsvwdafk gafiskhpcn iteedyqplm klgtqtvpcn killwsrikd lahqftqvqr dmftledtll gyladdltwc gefntskiny qscpdwrkdc snnpvsvfwk tvsrrfaeaa cdvvhvmlng srskifdkns tfgsvevhnl qpekvqtlea wvihggreds rdlcqdptik elesiiskrn iqfsckniyr pdkflqcvkn pedssctsei (SEQ ID NO:1). In some aspects, the CD38 antigen can be encoded by the sequence of nucleotides set forth in SEQ ID NO:2. In some embodiments, the portion of the antigen to which the antigen-binding domain specifically binds typically is within the extracellular region of the antigen. For example, with reference to SEQ ID NO:1, the extracellular region corresponds to amino acid residues 43-300 of SEQ ID NO:1, In some embodiments, the antigen may be one that is expressed or upregulated on cancer or tumor cells, but that also may be expressed in an immune cell, such as a resting or activated T cell. For example, in some cases, expression of hTERT, survivin and other universal tumor antigens are reported to be present in lymphocytes, including activated T lymphocytes (see e.g., Weng et al. (1996) *J Exp. Med.*, 183:2471-2479; Hathcock et al. (1998) *J Immunol.*, 160:5702-5706; Liu et al. (1999) *Proc. Natl Acad Sci.*, 96:5147-5152; Turksma et al. (2013) Journal of Translational Medicine, 11:152). Likewise, in some cases, CD38 and other tumor antigens also can be expressed in immune cells, such as T cells, such as upregulated in activated T cells. For example, in some aspects, CD38 is a known T cell activation marker. In some embodiments as provided herein, an immune cell, such as a T cell, can be engineered to repress or disrupt the gene encoding the antigen in the immune cell so that the expressed genetically engineered antigen receptor does not specifically bind the antigen in the context of its expression on the immune cell itself. Thus, in some aspects, this may avoid off-target effects, such as binding of the engineered immune cells to themselves, which may reduce the efficacy of the engineered in the immune cells, for example, in connection with adoptive cell therapy.

In some embodiments, such as in the case of an inhibitory CAR, the target is an off-target marker, such as an antigen not expressed on the diseased cell or cell to be targeted, but that is expressed on a normal or non-diseased cell which also expresses a disease-specific target being targeted by an activating or stimulatory receptor in the same engineered cell. Exemplary such antigens are MHC molecules, such as MHC class I molecules, for example, in connection with treating diseases or conditions in which such molecules become downregulated but remain expressed in non-targeted cells.

In some embodiments, the engineered immune cells can contain an antigen that targets one or more other antigens. In some embodiments, the one or more other antigens is a tumor antigen or cancer marker. Other antigen targeted by antigen receptors on the provided immune cells can, in some embodiments, include orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acetycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens.

In some embodiments, the CAR binds a pathogen-specific antigen. In some embodiments, the CAR is specific for viral antigens (such as HIV, HCV, HBV, etc.), bacterial antigens, and/or parasitic antigens.

Multi-Targeting

In some embodiments, the cells and methods include multi-targeting strategies, such as expression of two or more genetically engineered receptors on the cell, each recognizing a different antigen and typically each including a different intracellular signaling component. Such multi-targeting strategies are described, for example, in International Patent Application, Publication No.: WO 2014055668 A1 (describing combinations of activating and costimulatory CARs, e.g., targeting two different antigens present individually on off-target, e.g., normal cells, but present together only on cells of the disease or condition to be treated) and Fedorov et al., *Sci. Transl. Medicine,* 5 (215) (December, 2013) (describing cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat).

In some embodiments, the multi-targeting strategy is employed in a case where an antigen associated with a particular disease or condition is expressed on a non-diseased cell and/or is expressed on the engineered cell itself, either transiently (e.g., upon stimulation in association with genetic engineering) or permanently. In such cases, by requiring ligation of two separate and individually specific antigen receptors, specificity, selectivity, and/or efficacy may be improved.

For example, in some embodiments, the cells include a receptor expressing a first genetically engineered antigen receptor (e.g., CAR or TCR) which is capable of inducing an activating signal to the cell, generally upon specific binding to the antigen recognized by the first receptor, e.g., the first antigen. In some embodiments, the cell further includes a second genetically engineered antigen receptor (e.g., CAR or TCR), e.g., a chimeric costimulatory receptor, which is capable of inducing a costimulatory signal to the immune cell, generally upon specific binding to a second antigen recognized by the second receptor. In some aspects, the first receptor includes an intracellular signaling component containing ITAM or ITAM-like motifs. In some aspects, the second receptor includes intracellular signaling domains of costimulatory receptors such as CD28, CD137 (4-1 BB), OX40, and/or ICOS.

In some embodiments, the activation induced by the first receptor involves a signal transduction or change in protein expression in the cell resulting in initiation of an immune response, such as ITAM phosphorylation and/or initiation of ITAM-mediated signal transduction cascade, formation of an immunological synapse and/or clustering of molecules near the bound receptor (e.g. CD4 or CD8, etc.), activation of one or more transcription factors, such as NF-κB and/or AP-1, and/or induction of gene expression of factors such as cytokines, proliferation, and/or survival.

In some embodiments, the costimulatory signal induced by the second receptor, in combination with the signal induced by the first receptor, is one that results in an immune response, such as a robust and sustained immune response, such as increased gene expression, secretion of cytokines and other factors, and T cell mediated effector functions such as cell killing.

In some embodiments, neither ligation of the first receptor alone nor ligation of the second receptor alone induces a robust immune response. In some aspects, if only one receptor is ligated, the cell becomes tolerized or unresponsive to antigen, or inhibited, and/or is not induced to proliferate or secrete factors or carry out effector functions. In some such embodiments, however, when the plurality of receptors are ligated, such as upon encounter of a cell expressing the first and second antigens, a desired response is achieved, such as full immune activation or stimulation, e.g., as indicated by secretion of one or more cytokine, proliferation, persistence, and/or carrying out an immune effector function such as cytotoxic killing of a target cell.

In some embodiments, the plurality of antigens, e.g., the first and second antigens, are expressed on the cell, tissue, or disease or condition being targeted, such as on the cancer cell. In some aspects, the cell, tissue, disease or condition is multiple myeloma or a multiple myeloma cell. One or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is achieved.

In some embodiments, among the combinations of antigens for multi-targeting strategies includes those in which at least one of the antigens is a universal tumor antigen, such as hTERT, survivin, MDM2, CYP1B, HER2/neu, WT1, livin, AFP, CEA, MUC16, MUC1, PSMA, p53 or cyclin (D1), each individually in combination with a second antigen that also targets an antigen expressed on a tumor. In some embodiments, the universal tumor antigen and the second antigen target an antigen on the same tumor type. In some embodiments, the second antigen may also be another different universal tumor antigen or may be a tumor antigen specific to the tumor type. In some embodiments, the second antigen may be a tumor antigen, such as ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens In some embodiments, among the combinations of antigens for multi-targeting strategies include those expressed on multiple myeloma, such as CD38 (cyclic ADP ribose hydrolase), CD138 (syndecan-1, syndecan, SYN-1), and CS-1 (CS1, CD2 subset 1, CRACC, SLAMF7, CD319, and 19A24), each individually in combination with a second antigen that is also expressed in multiple myeloma. In some embodiments, the plurality of antigens, such as those recognized by activating and costimulatory engineered receptors, respectively, are CD38 and CD138, CD38 and CS-1, CD138 and CD38, CD138 and CS-1, CS-1 and CD38, and/or CS-1 and CD138. Additional multiple-myeloma-specific antigens include CD20, CD40, CD56, CD74, CD200, EGFR, BCMA, and β2-Microglobulin, HM1.24, IGF-1R, IL-6R, TRAIL-R1, and the activin receptor type IIA (ActRIIA). See Benson and Byrd, *Journal of Clinical Oncology*, Jun. 1, 2012, 30 (16): 2013-15; Tao and Anderson, *Bone Marrow Research*, Volume 2011 (2011), Article ID 924058, 14 pages; Chu et al., *Leukemia* (26 Sep. 2013) 2014 April; 28 (4):917-27; Garfall et al., *Discov Med.* 2014 January; 17 (91):37-46. In some embodiments, the antigens include those present on lymphoid tumors, myeloma, AIDS-associated lymphoma, and/or post-transplant lymphoproliferations, such as CD38.

In some embodiments, one or more of the multiple antigen receptors recognizes or binds to its antigen with relatively low affinity. In some aspects, the receptor binds to its antigen with a dissociation constant ($K_D$) of at least at or about $10^{-8}$ M, at least at or about $10^{-7}$ M, at least at or about $10^{-6}$ M, at least at or about $10^{-5}$ M, and/or at least at or about $10^{-4}$ M. In some such embodiments, a relatively lower affinity of the antigen receptor for the antigen helps ensure that a full response is not achieved by ligation of only one of the multiple genetically engineered antigen receptor. In some embodiments, the CD38-targeting receptor includes an antigen binding domain as disclosed, for example, in U.S. Patent Application, Publication No.: US20120189622 A1, such as antigen binding portion(s) of the antibody designated as OKT10 and of other antibodies described in Table 1 of the application, and of antibodies binding to similar or the same epitopes.

In some embodiments, the two receptors induce, respectively, an activating and an inhibitory signal to the cell, such that binding by one of the receptor to its antigen activates the cell or induces a response, but binding by the second inhibitory receptor to its antigen induces a signal that suppresses or dampens that response. Examples are combinations of activating CARs and inhibitory CARs or iCARs. Such a strategy may be used, for example, in which the activating CAR binds an antigen expressed in a disease or condition but which is also expressed on normal cells, and the inhibitory receptor binds to a separate antigen which is expressed on the normal cells but not cells of the disease or condition.

Vectors and Methods for Genetic Engineering

Also provided are methods, nucleic acids, compositions, and kits, for producing the genetically engineered cells. In some aspects, the genetic engineering involves introduction of a nucleic acid encoding the genetically engineered component or other component for introduction into the cell, such as a component encoding a gene-disruption protein or nucleic acid.

In some embodiments, gene transfer is accomplished by first stimulating cell growth, e.g., T cell growth, proliferation, and/or activation, followed by transduction of the activated cells, and expansion in culture to numbers sufficient for clinical applications.

In some contexts, overexpression of a stimulatory factor (for example, a lymphokine or a cytokine) may be toxic to a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell II:223, I977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some aspects, the cells further are engineered to promote expression of cytokines or other factors. Various methods for the introduction of genetically engineered components, e.g., antigen receptors, e.g., CARs, are well known and may be used with the provided methods and compositions. Exemplary methods include those for transfer of nucleic acids encoding the receptors, including via viral, e.g., retroviral or lentiviral, transduction, transposons, and electroporation.

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28 (10): 1137-46; Alonso-Camino et al. (2013) Mol Ther Nucl Acids 2, e93; Park et al., Trends Biotechnol. 2011 November; 29 (11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207, 453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) *J. Immunother.* 35 (9): 689-701; Cooper et al. (2003) *Blood.* 101:

1637-1644; Verhoeyen et al. (2009) *Methods Mol Biol.* 506: 97-114; and Cavalieri et al. (2003) Blood. 102 (2): 497-505.

In some embodiments, recombinant nucleic acids are transferred into T cells via electroporation (see, e.g., Chicaybam et al, (2013) *PLoS ONE* 8 (3): e60298 and Van Tedeloo et al. (2000) *Gene Therapy* 7 (16): 1431-1437). In some embodiments, recombinant nucleic acids are transferred into T cells via transposition (see, e.g., Manuri et al. (2010) Hum Gene Ther 21 (4): 427-437; Sharma et al. (2013) *Molec Ther Nucl Acids* 2, e74; and Huang et al. (2009) *Methods Mol Biol* 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

In other embodiments, the cells, e.g., T cells, are not engineered to express recombinant receptors, but rather include naturally occurring antigen receptors specific for desired antigens, such as tumor-infiltrating lymphocytes and/or T cells cultured in vitro or ex vivo, e.g., during the incubation step(s), to promote expansion of cells having particular antigen specificity. For example, in some embodiments, the cells are produced for adoptive cell therapy by isolation of tumor-specific T cells, e.g. autologous tumor infiltrating lymphocytes (TIL). The direct targeting of human tumors using autologous tumor infiltrating lymphocytes can in some cases mediate tumor regression (see Rosenberg S A, et al. (1988) N Engl J Med. 319:1676-1680). In some embodiments, lymphocytes are extracted from resected tumors. In some embodiments, such lymphocytes are expanded in vitro. In some embodiments, such lymphocytes are cultured with lymphokines (e.g., IL-2). In some embodiments, such lymphocytes mediate specific lysis of autologous tumor cells but not allogeneic tumor or autologous normal cells.

Other approaches and vectors for transfer of the genetically engineered nucleic acids encoding the genetically engineered products are those described, e.g., in international patent application, Publication No.: WO2014055668, and U.S. Pat. No. 7,446,190.

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

C. Repression of Gene Expression, Activity, or Function

Among the provided immune cells are immune cells in which the expression, activity, and/or function of one or more genes encoding an antigen of a genetically engineered antigen receptor is repressed in the cell. In some cases, a particular antigen of interest may be one that is expressed in a disease or condition, such as a tumor or cancer, but that may also be expressed by the immune cell, such as a T cell or activated T cell. In some aspects, expression of the antigen by the immune cell may be undesirable, such as in the context of engineering the immune cell with a genetically engineered antigen receptor for the antigen, for example, in the context of adoptive immunotherapy. Thus, in some embodiments, provided are immune cells, such as T cells, that contains a genetically engineered antigen receptor specific for a target antigen in a disease or condition, for example a tumor or cancer, and that also contains a disruption or repression of an endogenous gene in the cell encoding the antigen.

Also provided are methods for effecting such gene repression. In some embodiments, the gene repression is carried out by effecting a disruption in the gene, such as a knock-out, insertion, missense or frameshift mutation, such as a biallelic frameshift mutation, deletion of all or part of the gene, e.g., one or more exon or portion thereof, and/or knock-in. Such disruptions in some embodiments are effected by sequence-specific or targeted nucleases, including DNA-binding targeted nucleases such as zinc finger nucleases (ZFN) and transcription activator-like effector nucleases (TALENs), and RNA-guided nucleases such as a CRISPR-associated nuclease (Cas), specifically designed to be targeted to the sequence of a gene or a portion thereof.

In some embodiments, the methods of repressing or disrupting a gene in the cell can be performed prior, simultaneous or subsequent to the methods of introducing a nucleic acid molecule encoding a genetically engineered antigen receptor into the cells. For example, in some cases, the methods of repressing or disrupting a gene in the cell is performed prior to introducing a nucleic acid molecule encoding a genetically engineered antigen receptor into the cell.

Repressed/Disrupted Genes

In some embodiments, the gene repressed and/or disrupted encodes a product capable of having or contributing to an inhibitory effect on the engineered cell, such as inhibiting an immune response by the cell. For example, in some cases, the gene repressed and/or disrupted encodes an antigen recognized by a genetically engineered antigen receptor that is or is planned to be expressed on the immune cells, such as T cells.

In some embodiments, the gene encodes a target antigen specifically bound by an antigen receptor on the engineered cell, such as a genetically engineered antigen receptor, e.g., CAR. Thus, in some aspects, the gene being repressed encodes the target antigen of a CAR or other antigen receptor. Such aspects typically arise in the case of a target antigen expressed in a particular disease or condition but that is expressed on the cell type being engineered, or a subset thereof, such as upon activation of the engineered cell. Exemplary antigens are those expressed on activated or stimulated T cells or NK cells, and subsets thereof, particularly activated cells produced by stimulatory conditions used to promote the introduction of the nucleic acid encoding the CAR or other engineered receptor. In some embodiments, by disrupting or otherwise repressing expression of the antigen on the engineered cells, the methods and compositions provided here avoid or reduce the likelihood of killing of the engineered cells by the engineered cells themselves, thereby promoting efficacy.

In some embodiments, the gene encodes an antigen that is an activating and/or costimulatory CAR target. In some embodiments, the gene encodes an antigen that is a target in a multi-targeting strategy employing two or more genetically engineered antigen receptors, where at least one of the receptors is specific for an antigen that may be or is expressed on the immune cell, such as T cell or activated T cell.

In some embodiments, the gene disrupted or the expression or function of which is otherwise repressed is any that encodes a universal tumor antigen, and particularly a universal tumor antigen that is expressed or upregulated on the immune cell, such as on a T cell or an activated T cells. In some embodiments, the gene that is disrupted or repressed is one that encodes hTERT or survivin. In some cases, other exemplary genes that can be disrupted or repressed include those encoding the antigens MDM2, CYP1B, HER2/neu, WT1, livin, AFP, CEA, MUC16, MUC1, PSMA, p53 or cyclin (D1). In some embodiments, a targeted nuclease is targeted to a gene encoding hTERT, survivin, p53 or other universal tumor antigen. In some aspects, the targeting disrupts the gene, e.g., decreases or abolishes the expression of hTERT, survivin, p53 or other targeted universal tumor antigen in the cell.

For example, in some embodiments, provided are immune cells, such as T cells, that contain a genetically engineered antigen receptor that specifically binds an antigen from among hTERT, survivin MDM2, CYP1B, HER2/neu, WT1, livin, AFP, CEA, MUC16, MUC1, PSMA, p53 or cyclin (D1) and that contains disruption or expression of the corresponding endogenous gene in the immune cells. In some aspects, provided are immune cells, such as T cells, that contain a genetically engineered antigen receptor that specifically binds to an hTERT antigen and that contains disruption or repression of the corresponding endogenous hTERT gene in the cell. In other aspects, provided are immune cells, such as T cells, that contain a genetically engineered antigen receptor that specifically binds to a survivin gene and that contains disruption or repression of the corresponding endogenous survivin gene in the cell.

In particular embodiments, the gene disrupted or the expression or function of which is otherwise repressed encodes CD38, such as in a cell expressing an anti-CD38 engineered receptor, such as an anti-CD38 CAR. Other exemplary genes include those encoding antigens CD33 and TIM-3. See Mardiros et al., *Blood* 122 (18) (Oct. 31, 2013). Other exemplary genes include those encoding the antigens CD26, CD30, CD53, CD92, CD100, CD148, CD150, CD200, CD261, CD262, and CD362. In some embodiments, a targeted nuclease is targeted to a CD38 gene on the engineered cell. In some aspects, the targeting disrupts the CD38 gene, e.g., decreases or abolishes the expression of CD38 on the engineered cell. In some aspects, provided are immune cells, such as T cells, that contain a genetically engineered antigen receptor that specifically binds to CD38 antigen and that contains disruption or repression of the corresponding endogenous CD38 gene in the cell.

In some embodiments, the gene is an inhibitory CAR target. For example, in the context of an antigen that binds to an inhibitory CAR, gene disruption in some contexts prevents or reduces the likelihood of a molecule that is expressed by the engineered cells themselves inducing a dampening effect on a response of the engineered cells. Exemplary of such antigens are those expressed on normal or non-targeted or off-target cells (such that an inhibitory CAR molecule is included to prevent off-target effects), but is also expressed on the cell type used for genetic engineering, such as the T cell or NK cell. Exemplary antigens are MHC molecules, such as MHC-class I molecules, which can in some cases be downregulated in the context of immune evasion, cancer, or infection, but are generally expressed on nucleated cells. Other examples are any inhibitory CAR target that is also expressed on a T cell, NK cell, or other cell engineered for cell therapy.

In some embodiments, the gene encodes an immunoinhibitory molecule or other product that dampens or prevents activation or stimulation or other effector function of the engineered cell, such as its ability to proliferate, survive, secrete one or more factors, or recruit or carry out cell killing, for example, in response to binding via the engineered antigen receptor.

In some embodiments, the gene repressed encodes a protein that suppresses the immune system. In some embodiments, the repression reduces the suppressive effects of the gene product on the immune system. In some aspects, this increases the immune response to tumor cells. In some embodiments, the gene encodes an adenosine receptor, such as A2AR. Thus, in some embodiments, the expression, activity, and/or function of A2AR is repressed.

Techniques for Gene Repression

In some embodiments, the repression of the expression, activity, and/or function of the gene is carried out by disrupting the gene. In some aspects, the gene is disrupted so that its expression is reduced by at least at or about 20, 30, or 40%, generally at least at or about 50, 60, 70, 80, 90, or 95% as compared to the expression in the absence of the gene disruption or in the absence of the components introduced to effect the disruption.

In some embodiments, gene disruption is carried out by induction of one or more double-stranded breaks and/or one or more single-stranded breaks in the gene, typically in a targeted manner. In some embodiments, the double-stranded or single-stranded breaks are made by a nuclease, e.g. an endonuclease, such as a gene-targeted nuclease. In some aspects, the breaks are induced in the coding region of the gene, e.g. in an exon. For example, in some embodiments, the induction occurs near the N-terminal portion of the coding region, e.g. in the first exon, in the second exon, or in a subsequent exon.

In some aspects, the double-stranded or single-stranded breaks undergo repair via a cellular repair process, such as by non-homologous end-joining (NHEJ) or homology-directed repair (HDR). In some aspects, the repair process is error-prone and results in disruption of the gene, such as a frameshift mutation, e.g., biallelic frameshift mutation, which can result in complete knockout of the gene. For example, in some aspects, the disruption comprises inducing a deletion, mutation, and/or insertion. In some embodiments, the disruption results in the presence of an early stop codon. In some aspects, the presence of an insertion, deletion, translocation, frameshift mutation, and/or a premature stop codon results in repression of the expression, activity, and/or function of the gene.

In some embodiments, the repression is transient or reversible, such that expression of the gene is restored at a later time. In other embodiments, the repression is not reversible or transient, e.g., is permanent.

In some embodiments, gene repression is achieved using antisense techniques, such as by RNA interference (RNAi), short interfering RNA (siRNA), short hairpin (shRNA), and/or ribozymes are used to selectively suppress or repress expression of the gene. siRNA technology includes that based on RNAi utilizing a double-stranded RNA molecule having a sequence homologous with the nucleotide sequence of mRNA which is transcribed from the gene, and a sequence complementary with the nucleotide sequence. siRNA generally is homologous/complementary with one region of mRNA which is transcribed from the gene, or may be siRNA including a plurality of RNA molecules which are homologous/complementary with different regions.

DNA-Targeting Molecules and Complexes; Targeted Endonucleases

In some embodiments, the repression is achieved using a DNA-targeting molecule, such as a DNA-binding protein or DNA-binding nucleic acid, or complex, compound, or composition, containing the same, which specifically binds to or hybridizes to the gene. In some embodiments, the DNA-targeting molecule comprises a DNA-binding domain, e.g., a zinc finger protein (ZFP) DNA-binding domain, a transcription activator-like protein (TAL) or TAL effector (TALE) DNA-binding domain, a clustered regularly interspaced short palindromic repeats (CRISPR) DNA-binding domain, or a DNA-binding domain from a meganuclease.

Zinc finger, TALE, and CRISPR system binding domains can be "engineered" to bind to a predetermined nucleotide sequence, for example via engineering (altering one or more amino acids) of the recognition helix region of a naturally occurring zinc finger or TALE protein. Engineered DNA binding proteins (zinc fingers or TALEs) are proteins that are non-naturally occurring. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 20110301073.

In some embodiments, the DNA-targeting molecule, complex, or combination contains a DNA-binding molecule and one or more additional domain, such as an effector domain to facilitate the repression or disruption of the gene. For example, in some embodiments, the gene disruption is carried out by fusion proteins that comprise DNA-binding proteins and a heterologous regulatory domain or functional fragment thereof. In some aspects, domains include, e.g., transcription factor domains such as activators, repressors, co-activators, co-repressors, silencers, oncogenes, DNA repair enzymes and their associated factors and modifiers, DNA rearrangement enzymes and their associated factors and modifiers, chromatin associated proteins and their modifiers, e.g. kinases, acetylases and deacetylases, and DNA modifying enzymes, e.g. methyltransferases, topoisomerases, helicases, ligases, kinases, phosphatases, polymerases, endonucleases, and their associated factors and modifiers. See, for example, U.S. Patent Application Publication Nos. 20050064474; 20060188987 and 2007/0218528, incorporated by reference in their entireties herein, for details regarding fusions of DNA-binding domains and nuclease cleavage domains. In some aspects, the additional domain is a nuclease domain. Thus, in some embodiments, gene disruption is facilitated by gene or genome editing, using engineered proteins, such as nucleases and nuclease-containing complexes or fusion proteins, composed of sequence-specific DNA-binding domains fused to or complexed with non-specific DNA-cleavage molecules such as nucleases.

In some aspects, these targeted chimeric nucleases or nuclease-containing complexes carry out precise genetic modifications by inducing targeted double-stranded breaks or single-stranded breaks, stimulating the cellular DNA-repair mechanisms, including error-prone non-homologous end joining (NHEJ) and homology-directed repair (HDR). In some embodiments the nuclease is an endonuclease, such as a zinc finger nuclease (ZFN), TALE nuclease (TALEN), an RNA-guided endonuclease (RGEN), such as a CRISPR-associated (Cas) protein, or a meganuclease.

In some embodiments, a donor nucleic acid, e.g., a donor plasmid or nucleic acid encoding the genetically engineered antigen receptor, is provided and is inserted by HDR at the site of gene editing following the introduction of the DSBs. Thus, in some embodiments, the disruption of the gene and the introduction of the antigen receptor, e.g., CAR, are carried out simultaneously, whereby the gene is disrupted in part by knock-in or insertion of the CAR-encoding nucleic acid.

In some embodiments, no donor nucleic acid is provided. In some aspects, NHEJ-mediated repair following introduction of DSBs results in insertion or deletion mutations that can cause gene disruption, e.g., by creating missense mutations or frameshifts.

ZFPs and ZFNs; TALs, TALEs, and TALENs

In some embodiments, the DNA-targeting molecule includes a DNA-binding protein such as one or more zinc finger protein (ZFP) or transcription activator-like protein (TAL), fused to an effector protein such as an endonuclease. Examples include ZFNs, TALEs, and TALENs. See Lloyd et al., Fronteirs in Immunology, 4 (221), 1-7 (2013).

In some embodiments, the DNA-targeting molecule comprises one or more zinc-finger proteins (ZFPs) or domains thereof that bind to DNA in a sequence-specific manner. A ZFP or domain thereof is a protein or domain within a larger protein, that binds DNA in a sequence-specific manner through one or more zinc fingers, regions of amino acid sequence within the binding domain whose structure is stabilized through coordination of a zinc ion. The term zinc finger DNA binding protein is often abbreviated as zinc finger protein or ZFP.

Among the ZFPs are artificial ZFP domains targeting specific DNA sequences, typically 9-18 nucleotides long, generated by assembly of individual fingers.

ZFPs include those in which a single finger domain is approximately 30 amino acids in length and contains an alpha helix containing two invariant histidine residues coordinated through zinc with two cysteines of a single beta turn, and having two, three, four, five, or six fingers. Generally, sequence-specificity of a ZFP may be altered by making amino acid substitutions at the four helix positions (−1, 2, 3 and 6) on a zinc finger recognition helix. Thus, in some embodiments, the ZFP or ZFP-containing molecule is non-naturally occurring, e.g., is engineered to bind to a target site of choice. See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416; U.S. Pat. Nos. 6,453,242; 6,534,261; 6,599, 692; 6,503,717; 6,689,558; 7,030,215; 6,794,136; 7,067, 317; 7,262,054; 7,070,934; 7,361,635; 7,253,273; and U.S. Patent Publication Nos. 2005/0064474; 2007/0218528; 2005/0267061, all incorporated herein by reference in their entireties.

In some aspects, repression of the gene is carried out by contacting a first target site in the gene with a first ZFP, thereby repressing the gene. In some embodiments, the target site in the gene is contacted with a fusion ZFP comprising six fingers and the regulatory domain, thereby inhibiting expression of the gene.

In some embodiments, the step of contacting further comprises contacting a second target site in the gene with a second ZFP. In some aspects, the first and second target sites are adjacent. In some embodiments, the first and second ZFPs are covalently linked. In some aspects, the first ZFP is a fusion protein comprising a regulatory domain or at least two regulatory domains. In some embodiments, the first and second ZFPs are fusion proteins, each comprising a regulatory domain or each comprising at least two regulatory domains. In some embodiments, the regulatory domain is a transcriptional repressor, a transcriptional activator, an endonuclease, a methyl transferase, a histone acetyltransferase, or a histone deacetylase.

In some embodiments, the ZFP is encoded by a ZFP nucleic acid operably linked to a promoter. In some aspects, the method further comprises the step of first administering the nucleic acid to the cell in a lipid:nucleic acid complex or as naked nucleic acid. In some embodiments, the ZFP is encoded by an expression vector comprising a ZFP nucleic acid operably linked to a promoter. In some embodiments, the ZFP is encoded by a nucleic acid operably linked to an inducible promoter. In some aspects, the ZFP is encoded by a nucleic acid operably linked to a weak promoter.

In some embodiments, the target site is upstream of a transcription initiation site of the gene. In some aspects, the target site is adjacent to a transcription initiation site of the gene. In some aspects, the target site is adjacent to an RNA polymerase pause site downstream of a transcription initiation site of the gene.

In some embodiments, the DNA-targeting molecule is or comprises a zinc-finger DNA binding domain fused to a DNA cleavage domain to form a zinc-finger nuclease (ZFN). In some embodiments, fusion proteins comprise the cleavage domain (or cleavage half-domain) from at least one Type IIS restriction enzyme and one or more zinc finger binding domains, which may or may not be engineered. In some embodiments, the cleavage domain is from the Type IIS restriction endonuclease Fok I. Fok I generally catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982.]

In some embodiments, ZFNs target a gene present in the engineered cell. In some aspects, the ZFNs efficiently generate a double strand break (DSB), for example at a predetermined site in the coding region of the gene. Typical regions targeted include exons, regions encoding N-terminal regions, first exon, second exon, and promoter or enhancer regions. In some embodiments, transient expression of the ZFNs promotes highly efficient and permanent disruption of the target gene in the engineered cells. In particular, in some embodiments, delivery of the ZFNs results in the permanent disruption of the gene with efficiencies surpassing 50%.

Many gene-specific engineered zinc fingers are available commercially. For example, Sangamo Biosciences (Richmond, Calif., USA) has developed a platform (CompoZr) for zinc-finger construction in partnership with Sigma-Aldrich (St. Louis, Mo., USA), allowing investigators to bypass zinc-finger construction and validation altogether, and provides specifically targeted zinc fingers for thousands of proteins. Gaj et al., Trends in Biotechnology, 2013, 31 (7), 397-405. In some embodiments, commercially available zinc fingers are used or are custom designed. (See, for example, Sigma-Aldrich catalog numbers CSTZFND, CSTZFN, CTI1-1KT, and PZD0020).

TALEs and TALENs

In some embodiments, the DNA-targeting molecule comprises a naturally occurring or engineered (non-naturally occurring) transcription activator-like protein (TAL) DNA binding domain, such as in a transcription activator-like protein effector (TALE) protein, See, e.g., U.S. Patent Publication No. 20110301073, incorporated by reference in its entirety herein.

A TALE DNA binding domain or TALE is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. Each TALE repeat unit includes 1 or 2 DNA-binding residues making up the Repeat Variable Diresidue (RVD), typically at positions 12 and/or 13 of the repeat. The natural (canonical) code for DNA recognition of these TALEs has been determined such that an HD sequence at positions 12 and 13 leads to a binding to cytosine (C), NG binds to T, NI to A, NN binds to G or A, and NG binds to T and non-canonical (atypical) RVDs are also known. See, U.S. Patent Publication No. 20110301073. In some embodiments, TALEs may be targeted to any gene by design of TAL arrays with specificity to the target DNA sequence. The target sequence generally begins with a thymidine.

In some embodiments, the molecule is a DNA binding endonuclease, such as a TALE-nuclease (TALEN). In some aspects the TALEN is a fusion protein comprising a DNA-binding domain derived from a TALE and a nuclease catalytic domain to cleave a nucleic acid target sequence. In some embodiments, the TALE DNA-binding domain has been engineered to bind a target sequence within genes that encode the target antigen and/or the immunosuppressive molecule. For example, in some aspects, the TALE DNA-binding domain may target CD38 and/or an adenosine receptor, such as A2AR.

In some embodiments, the TALEN recognizes and cleaves the target sequence in the gene. In some aspects, cleavage of the DNA results in double-stranded breaks. In some aspects the breaks stimulate the rate of homologous recombination or non-homologous end joining (NHEJ). Generally, NHEJ is an imperfect repair process that often results in changes to the DNA sequence at the site of the cleavage. In some aspects, repair mechanisms involve rejoining of what remains of the two DNA ends through direct re-ligation (Critchlow and Jackson, Trends Biochem Sci. 1998 October; 23 (10):394-8) or via the so-called microhomology-mediated end joining. In some embodiments, repair via NHEJ results in small insertions or deletions and can be used to disrupt and thereby repress the gene. In some embodiments, the modification may be a substitution, deletion, or addition of at least one nucleotide. In some aspects, cells in which a cleavage-induced mutagenesis event, i.e. a mutagenesis event consecutive to an NHEJ event, has occurred can be identified and/or selected by well-known methods in the art.

In some embodiments, TALE repeats are assembled to specifically target a gene. (Gaj et al., Trends in Biotechnology, 2013, 31 (7), 397-405). A library of TALENs targeting 18,740 human protein-coding genes has been constructed (Kim et al., Nature Biotechnology. 31, 251-258 (2013)). Custom-designed TALE arrays are commercially available through Cellectis Bioresearch (Paris, France), Transposagen Biopharmaceuticals (Lexington, Ky., USA), and Life Technologies (Grand Island, N.Y., USA). Specifically, TALENs that target CD38 are commercially available (See Gencopoeia, catalog numbers HTN222870-1, HTN222870-2, and HTN222870-3, available on the World Wide Web at www-.genecopoeia.com/product/search/detail.php?prt=26&cid=&key=HTN222870). Exemplary molecules are described, e.g., in U.S. Patent Publication Nos. US 2014/0120622, and 2013/0315884.

In some embodiments the TALENs are introduced as transgenes encoded by one or more plasmid vectors. In some aspects, the plasmid vector can contain a selection marker which provides for identification and/or selection of cells which received said vector.

RGENs (CRISPR/Cas Systems)

In some embodiments, the repression is carried out using one or more DNA-binding nucleic acids, such as disruption via an RNA-guided endonuclease (RGEN), or other form of repression by another RNA-guided effector molecule. For example, in some embodiments, the repression is carried out using clustered regularly interspaced short palindromic repeats (CRISPR) and CRISPR-associated (Cas) proteins. See Sander and Joung, *Nature Biotechnology,* 32 (4): 347-355.

In general, "CRISPR system" refers collectively to transcripts and other elements involved in the expression of or directing the activity of CRISPR-associated ("Cas") genes, including sequences encoding a Cas gene, a tracr (transactivating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), and/or other sequences and transcripts from a CRISPR locus.

In some embodiments, the CRISPR/Cas nuclease or CRISPR/Cas nuclease system includes a non-coding RNA molecule (guide) RNA, which sequence-specifically binds to DNA, and a Cas protein (e.g., Cas9), with nuclease functionality (e.g., two nuclease domains).

In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes*.

In some embodiments, a Cas nuclease and gRNA (including a fusion of crRNA specific for the target sequence and fixed tracrRNA) are introduced into the cell. In general, target sites at the 5' end of the gRNA target the Cas nuclease to the target site, e.g., the gene, using complementary base pairing. In some embodiments, the target site is selected based on its location immediately 5' of a proto spacer adjacent motif (PAM) sequence, such as typically NGG, or NAG. In this respect, the gRNA is targeted to the desired sequence by modifying the first 20 nucleotides of the guide RNA to correspond to the target DNA sequence.

In some embodiments, the CRISPR system induces DSBs at the target site, followed by disruptions as discussed herein. In other embodiments, Cas9 variants, deemed "nickases" are used to nick a single strand at the target site. In some aspects, paired nickases are used, e.g., to improve specificity, each directed by a pair of different gRNAs targeting sequences such that upon introduction of the nicks simultaneously, a 5' overhang is introduced. In other embodiments, catalytically inactive Cas9 is fused to a heterologous effector domain such as a transcriptional repressor or activator, to affect gene expression.

In general, a CRISPR system is characterized by elements that promote the formation of a CRISPR complex at the site of a target sequence. Typically, the In the context of formation of a CRISPR complex, "target sequence" generally refers to a sequence to which a guide sequence is designed to have complementarity, where hybridization between the target sequence and a guide sequence promotes the formation of a CRISPR complex. Full complementarity is not necessarily required, provided there is sufficient complementarity to cause hybridization and promote formation of a CRISPR complex.

The target sequence may comprise any polynucleotide, such as DNA or RNA polynucleotides. In some embodiments, the target sequence is located in the nucleus or cytoplasm of the cell. In some embodiments, the target sequence may be within an organelle of the cell. Generally, a sequence or template that may be used for recombination into the targeted locus comprising the target sequences is referred to as an "editing template" or "editing polynucleotide" or "editing sequence". In some aspects, an exogenous template polynucleotide may be referred to as an editing template. In some aspects, the recombination is homologous recombination.

Typically, in the context of an endogenous CRISPR system, formation of the CRISPR complex (comprising the guide sequence hybridized to the target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of the CRISPR complex, such as by hybridization along at least a portion of the tracr sequence to all or a portion of a tracr mate sequence that is operably linked to the guide sequence. In some embodiments, the tracr sequence has sufficient complementarity to a tracr mate sequence to hybridize and participate in formation of the CRISPR complex.

As with the target sequence, in some embodiments, complete complementarity is not necessarily needed. In some embodiments, the tracr sequence has at least 50%, 60%, 70%, 80%, 90%, 95% or 99% of sequence complementarity along the length of the tracr mate sequence when optimally aligned. In some embodiments, one or more vectors driving expression of one or more elements of the CRISPR system are introduced into the cell such that expression of the elements of the CRISPR system direct formation of the CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. In some embodiments, CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter.

In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of the CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to the cell.

In some embodiments, a vector comprises a regulatory element operably linked to an enzyme-coding sequence encoding the CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of S. pyogenes Cas9 protein may be found in the SwissProt database under accession number Q99ZW2. In some embodiments, the unmodified CRISPR enzyme has DNA cleavage activity, such as Cas9. In some embodiments the CRISPR enzyme is Cas9, and may be Cas9 from S. pyogenes or S. pneumoniae. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from S. pyogenes converts Cas9 from a nuclease that cleaves both strands to a nickase (cleaves a single strand). In some embodiments, a Cas9 nickase may be used in combination with guide sequence(s), e.g., two guide sequences, which target respectively sense and antisense strands of the DNA target. This combination allows both strands to be nicked and used to induce NHEJ.

In some embodiments, an enzyme coding sequence encoding the CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. In some embodiments, one or more codons (e.g. 1, 2, 3, 4, 5, 10, 15, 20, 25, 50, or more, or all codons) in a sequence encoding the CRISPR enzyme correspond to the most frequently used codon for a particular amino acid.

In general, a guide sequence is any polynucleotide sequence having sufficient complementarity with a target polynucleotide sequence to hybridize with the target sequence and direct sequence-specific binding of the CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more.

Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of the CRISPR complex to a target sequence may be assessed by any suitable assay. For example, the components of the CRISPR system sufficient to form the CRISPR complex, including the guide sequence to be tested, may be provided to the cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of the CRISPR complex, including the guide sequence to be tested and a control guide sequence different from the test guide sequence, and comparing binding or rate of cleavage at the target sequence between the test and control guide sequence reactions.

A guide sequence may be selected to target any target sequence. In some embodiments, the target sequence is a sequence within a genome of a cell. Exemplary target sequences include those that are unique in the target genome. In some embodiments, a guide sequence is selected to reduce the degree of secondary structure within the guide sequence. Secondary structure may be determined by any suitable polynucleotide folding algorithm.

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences.

Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In some aspects, loop forming sequences for use in hairpin structures are four nucleotides in length, and have the sequence GAAA. However, longer or shorter loop sequences may be used, as may alternative sequences. In some embodiments, the sequences include a nucleotide triplet (for example, AAA), and an additional nucleotide (for example C or G). Examples of loop forming sequences include CAAA and AAAG. In some embodiments, the transcript or transcribed polynucleotide sequence has at least two or more hairpins. In some embodiments, the transcript has two, three, four or five hairpins. In a further embodiment, the transcript has at most five hairpins. In some embodiments, the single transcript further includes a transcription termination sequence, such as a polyT sequence, for example six T nucleotides.

In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-5-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4A DNA binding domain fusions, and herpes simplex virus (HSV) BP16 protein fusions. Additional domains that may form part of a fusion protein comprising a CR ISPR enzyme are described in US20110059502, incorporated herein by reference. In some embodiments, a tagged CRISPR enzyme is used to identify the location of a target sequence.

In some embodiments, a CRISPR enzyme in combination with (and optionally complexed with) a guide sequence is delivered to the cell. For example, CRISPR/Cas9 technology may be used to knock-down gene expression of the target antigen in the engineered cells. In an exemplary method, Cas9 nuclease (e.g., that encoded by mRNA from *Staphylococcus aureus* or from *Streptococcus pyogenes*, e.g. pCW-Cas9, Addgene #50661, Wang et al. (2014) Science, 3:343-80-4; or nuclease or nickase lentiviral vectors available from Applied Biological Materials (ABM; Canada) as Cat. No. K002, K003, K005 or K006) and a guide RNA specific to the target antigen gene are introduced into cells, for example, using lentiviral delivery vectors or any of a number of known delivery method or vehicle for transfer to cells, such as any of a number of known methods or vehicles for delivering Cas9 molecules and guide RNAs. Non-specific or empty vector control T cells also are generated. Degree of Knockout of a gene (e.g., 24 to 72 hours after transfer) is assessed using any of a number of well-known assays for assessing gene disruption in cells.

Commerically available kits, gRNA vectors and donor vectors, for knockout of a universal tumor antigen, such any one or more of MDM2, CYP1B, HER2/neu, WT1, livin, AFP, CEA, MUC16, MUC1, PSMA, p53 or cyclin (D1) are available, for example, from Origene (Rockville, Md.), GenScript (Atlanta, Ga.), Applied Biological Materials (ABM; Richmond, British Colombia), BioCat (Heidelberg, Germany) or others. For example, commerically available kits for knockout of hTERT via CRISPR include, for example, those available as catalog numbers K0009801, K0009802, K009803 and/or K0009804 each available from ABM. Commercially available kits for knockout of survivin via CRISPR include, for example, catalog numbers KN205935 available from Origene and catalog numbers K0184401, K0184402, K0184403, K0184404 each available from ABM. Commercially available kits for knockout of MDM2 via CRISPR include, for example, KN219518 from Origene and catalog number K1283521 from ABM. Commerically available kits for knockout of Her2/neu via CRISPR include, for example, KN212583 from Origene.

Commercially available kits for knockout of Cyp1B1 via CRISPR include, for example, KN204074-OR available from BioCat. Commercially available kits for knockout of WT1 via CRISPR include, for example, KN220079 from Origine.

Commercially available kits, gRNA vectors and donor vectors, for knockout of CD38 via CRISPR are available, for example, from OriGene. See www.origene.com/CRISPR-CAS9/Product.aspx?SKU=KN203179; catalog numbers KN203179G1, KN203179G2, KN203179D.

In some aspects, target polynucleotides are modified in a eukaryotic cell. In some embodiments, the method comprises allowing the CRISPR complex to bind to the target polynucleotide to effect cleavage of said target polynucleotide thereby modifying the target polynucleotide, wherein the CRISPR complex comprises the CRISPR enzyme complexed with a guide sequence hybridized to a target sequence within said target polynucleotide, wherein said guide sequence is linked to a tracr mate sequence which in turn hybridizes to a tracr sequence.

In some aspects, the methods include modifying expression of a polynucleotide in a eukaryotic cell. In some embodiments, the method comprises allowing the CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence.

Delivery of Nucleic Acids Encoding the Gene Disrupting Molecules and Complexes

In some aspects, a nucleic acid encoding the DNA-targeting molecule, complex, or combination, is administered or introduced to the cell. The nucleic acid typically is administered in the form of an expression vector, such as a viral expression vector. In some aspects, the expression vector is a retroviral expression vector, an adenoviral expression vector, a DNA plasmid expression vector, or an AAV expression vector. In some aspects, one or more polynucleotides encoding the disruption molecule or complex, such as the DNA-targeting molecule, is delivered to the cell. In some aspects, the delivery is by delivery of one or more vectors, one or more transcripts thereof, and/or one or more proteins transcribed therefrom, is delivered to the cell.

In some embodiments, the polypeptides are synthesized in situ in the cell as a result of the introduction of polynucleotides encoding the polypeptides into the cell. In some aspects, the polypeptides could be produced outside the cell and then introduced thereto. Methods for introducing a polynucleotide construct into animal cells are known and include, as non-limiting examples stable transformation methods wherein the polynucleotide construct is integrated into the genome of the cell, transient transformation methods wherein the polynucleotide construct is not integrated into the genome of the cell, and virus mediated methods. In some embodiments, the polynucleotides may be introduced into the cell by for example, recombinant viral vectors (e.g. retroviruses, adenoviruses), liposome and the like. For example, in some aspects, transient transformation methods include microinjection, electroporation, or particle bombardment. In some embodiments, the polynucleotides may be included in vectors, more particularly plasmids or virus, in view of being expressed in the cells.

In some embodiments, viral and non-viral based gene transfer methods can be used to introduce nucleic acids in mammalian cells or target tissues. Such methods can be used to administer nucleic acids encoding components of a CRISPR, ZFP, ZFN, TALE, and/or TALEN system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon. TIBTECH 11:167-175 (1993); Miller, Nature 357:455-460 (1992); Van Brunt, Biotechnology 6 (10): 1149-1154 (1988); Vigne, Restorative Neurology and Neuroscience 8:35-36 (1995); Kremer & Perricaudet, British Medical Bulletin 51 (1):31-44 (1995); Haddada et al., in Current Topics in Microbiology and Immunology Doerfler and Bohm (eds) (1995); and Yu et al., Gene Therapy 1:13-26 (1994).

Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration).

In some embodiments, delivery is via the use of RNA or DNA viral based systems for the delivery of nucleic acids. Viral vectors in some aspects may be administered directly to patients (in vivo) or they can be used to treat cells in vitro or ex vivo, and then administered to patients. Viral-based systems in some embodiments include retroviral, lentivirus, adenoviral, adeno-associated and herpes simplex virus vectors for gene transfer.

In some aspects, a reporter gene which includes but is not limited to glutathione-5-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP), may be introduced into the cell to encode a gene product which serves as a marker by which to measure the alteration or modification of expression of the gene product. In a further embodiment, the DNA molecule encoding the gene product may be introduced into the cell via a vector. In some embodiments, the gene product is luciferase. In a further embodiment, the expression of the gene product is decreased.

II. Compositions, Formulations, Kits, Devices, Methods, and Uses

Also provided are cells, cell populations, and compositions containing the cells produced by the provided methods. Among the compositions are pharmaceutical compositions and formulations for administration, such as for adoptive cell therapy. Also provided are therapeutic methods for administrating the cells and compositions to subjects, e.g., patients.

Provided are methods and uses of the cells, including therapeutic methods and uses, such as in adoptive cell therapy. In some embodiments, the methods include administration of the cells or a composition containing the cells to a subject, tissue, or cell, such as one having, at risk for, or suspected of having a disease, condition or disorder. In some embodiments, the methods treat cancers and other diseases, conditions, and disorders. In some embodiments, the cells, populations, and compositions are administered to a subject having the particular disease or condition to be treated, e.g., via adoptive cell therapy, such as adoptive T cell therapy. In some embodiments, the cells or compositions are administered to the subject, such as a subject having or at risk for the disease or condition. In some aspects, the methods thereby treat, e.g., ameliorate one or more symptom of, the disease or condition, such as by lessening tumor burden in a cancer expressing an antigen recognized by the engineered cell.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8 (10):577-85). See, e.g., Themeli et al. (2013) *Nat Biotechnol.* 31 (10): 928-933; Tsukahara et al. (2013) *Biochem Biophys Res Commun* 438 (1): 84-9; Davila et al. (2013) *PLoS ONE* 8 (4): e61338.

In some embodiments, the cell therapy, e.g., adoptive cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject, e.g., patient, to whom the cells, cell populations, or compositions are administered is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent. In some examples, the patient or subject is a validated animal model for disease, adoptive cell therapy, and/or for assessing toxic outcomes such as cytokine release syndrome (CRS).

Also provided are pharmaceutical compositions for use in such methods.

Among the diseases, conditions, and disorders are tumors, including solid tumors, hematologic malignancies, and melanomas, and infectious diseases, such as infection with a virus or other pathogen, e.g., HIV, HCV, HBV, CMV, and parasitic disease. In some embodiments, the disease or condition is a tumor, cancer, malignancy, neoplasm, or other proliferative disease. Such diseases include but are not limited to cancers of the immune system, leukemia, lymphoma, e.g., chronic lymphocytic leukemia (CLL), ALL, non-Hodgkin's lymphoma, acute myeloid leukemia, multiple myeloma, refractory follicular lymphoma, mantle cell lymphoma, indolent B cell lymphoma, B cell malignancies, cancers of the colon, lung, liver, breast, prostate, ovarian, skin (including melanoma), bone, and brain cancer, ovarian cancer, epithelial cancers, renal cell carcinoma, pancreatic adenocarcinoma, Hodgkin lymphoma, cervical carcinoma, colorectal cancer, glioblastoma, neuroblastoma, Ewing sarcoma, medulloblastoma, osteosarcoma, synovial sarcoma, and/or mesothelioma. In one embodiment, the disease or condition is or is associated with multiple myeloma.

In some embodiments, the disease or condition is an infectious disease or condition, such as, but not limited to, viral, retroviral, bacterial, and protozoal infections, immunodeficiency, Cytomegalovirus (CMV), Epstein-Ban virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease multiple sclerosis, asthma, and/or a disease or condition associated with transplant.

In some embodiments, the one or more genetically engineered antigen receptors specifically binds to a target antigen associated with the disease or disorder. In some cases, two more genetically engineered antigen receptors bind to two or more different antigens associated with the disease or disorder. In some embodiments, at least one antigen associated with the disease or disorder is a universal tumor antigen. For example, in some cases the antigen is hTERT, survivin, MDM2, CYP1B, HER2/neu, WT1, livin, AFP, CEA, MUC16, MUC1, PSMA, p53 or cyclin (D1). For example, the universal tumor antigen is hTERT or survivin. In some embodiments, at least one antigen associated with the disease or disorder is a myeloma antigen. For example, in some cases, the myeloma antigen is CD38, CD138, CS-1, CD56, TIM-3, CD33, CD123 or CD44. For example, the myeloma antigen is CD38.

In some embodiments, one or more other antigens associated with the disease or disorder is selected from the group consisting of orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, OEPHa2, ErbB2, 3, or 4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens. The antigens include proteins, carbohydrates, and other molecules.

In some embodiments, the cells and cell populations are administered to a subject in the form of a composition, such as a pharmaceutical composition. In some embodiments, the pharmaceutical composition further comprises other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the cell populations are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

In some aspects, the choice of carrier can in the pharmaceutical composition is determined in part by the particular engineered CAR or TCR, vector, or cells expressing the CAR or TCR, as well as by the particular method used to administer the vector or host cells expressing the CAR. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition.

In addition, buffering agents in some aspects are included in the composition. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

In certain embodiments, a pharmaceutical composition comprising a cell population described herein can be formulated as an inclusion complex, such as cyclodextrin inclusion complex, or as a liposome. Liposomes can serve to target the host cells (e.g., T-cells or NK cells) to a particular tissue. Many methods are available for preparing liposomes, such as those described in, for example, Szoka et al., Ann. Rev. Biophys. Bioeng., 9: 467 (1980), and U.S. Pat. Nos. 4,235,871, 4,501,728, 4,837,028, and 5,019,369.

The pharmaceutical composition in some aspects can employ time-released, delayed release, and sustained release delivery systems such that the delivery of the composition occurs prior to, and with sufficient time to cause, sensitization of the site to be treated. Many types of release delivery systems are available and known to those of ordinary skill in the art. Such systems can avoid repeated administrations of the composition, thereby increasing convenience to the subject and the physician.

The pharmaceutical composition in some embodiments comprises the cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

In certain embodiments, a subject is administered the range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges.

The cells and compositions in some embodiments are administered using standard administration techniques, formulations, and/or devices. Provided are formulations and devices, such as syringes and vials, for storage and administration of the compositions. Administration can be autologous or heterologous. For example, immunoresponsive cells or progenitors can be obtained from one subject, and administered to the same subject or a different, compatible subject. Peripheral blood derived immunoresponsive cells of the invention or their progeny (e.g., in vivo, ex vivo or in vitro derived) can be administered via localized injection, including catheter administration, systemic injection, localized injection, intravenous injection, or parenteral administration. When administering a therapeutic composition of the present invention (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cell populations are administered to a subject using peripheral systemic delivery by intravenous, intraperitoneal, or subcutaneous injection.

Compositions of the cells in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the genetically engineered in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cell populations are administered prior to the one or more additional therapeutic agents. In some embodiments, the cell populations are administered after to the one or more additional therapeutic agents.

Once the cells are administered to a mammal (e.g., a human), the biological activity of the engineered cell populations in some aspects is measured by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32 (7): 689-702 (2009), and Herman et al. J. Immunological Methods, 285 (1): 25-40 (2004). In certain embodiments, the biological activity of the cells also can be measured by assaying expression and/or secretion of certain cytokines, such as CD 107a, IFNγ, IL-2, and TNF. In some aspects the biological activity is measured by assessing clinical outcome, such as reduction in tumor burden or load.

In certain embodiments, engineered cells are modified in any number of ways, such that their therapeutic or prophylactic efficacy is increased. For example, the engineered CAR or TCR expressed by the population can be conjugated either directly or indirectly through a linker to a targeting moiety. The practice of conjugating compounds, e.g., the CAR or TCR, to targeting moieties is known in the art. See, for instance, Wadwa et al., J. Drug Targeting 3: 1 1 1 (1995), and U.S. Pat. No. 5,087,616.

III. Definitions

As used herein, "repression" of gene expression refers to the elimination or reduction of expression of one or more gene products encoded by the subject gene in a cell, compared to the level of expression of the gene product in the absence of the repression. Exemplary gene products include mRNA and protein products encoded by the gene. Repression in some cases is transient or reversible and in other cases is permanent. Repression in some cases is of a functional or full-length protein or mRNA, despite the fact that a truncated or non-functional product may be produced. In some embodiments herein, gene activity or function, as opposed to expression, is repressed. Gene repression is generally induced by artificial methods, i.e., by addition or introduction of a compound, molecule, complex, or composition, and/or by disruption of nucleic acid of or associated with the gene, such as at the DNA level. Exemplary methods for gene repression include gene silencing, knockdown, knockout, and/or gene disruption techniques, such as gene editing. Examples include antisense technology, such as RNAi, siRNA, shRNA, and/or ribozymes, which generally result in transient reduction of expression, as well as gene editing techniques which result in targeted gene inactivation or disruption, e.g., by induction of breaks and/or homologous recombination.

As used herein, a "disruption" of a gene refers to a change in the sequence of the gene, at the DNA level. Examples include insertions, mutations, and deletions. The disruptions typically result in the repression and/or complete absence of expression of a normal or "wild type" product encoded by the gene. Exemplary of such gene disruptions are insertions, frameshift and missense mutations, deletions, knock-in, and knock-out of the gene or part of the gene, including deletions of the entire gene. Such disruptions can occur in the coding region, e.g., in one or more exons, resulting in the inability to produce a full-length product, functional product, or any product, such as by insertion of a stop codon. Such disruptions may also occur by disruptions in the promoter or enhancer or other region affecting activation of transcription, so as to prevent transcription of the gene. Gene disruptions include gene targeting, including targeted gene inactivation by homologous recombination.

As used herein, the singular forms "a," "an," and "the" include plural referents unless the context clearly dictates otherwise. For example, "a" or "an" means "at least one" or "one or more."

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se.

As used herein, a subject includes any living organism, such as humans and other mammals. Mammals include, but are not limited to, humans, and non-human animals, including farm animals, sport animals, rodents and pets.

As used herein, a composition refers to any mixture of two or more products, substances, or compounds, including cells. It may be a solution, a suspension, liquid, powder, a paste, aqueous, non-aqueous or any combination thereof.

As used herein, the terms "treatment," "treat," and "treating," refer to complete or partial amelioration or reduction of a disease or condition or disorder, or a symptom, adverse effect or outcome, or phenotype associated therewith. In certain embodiments, the effect is therapeutic, such that it partially or completely cures a disease or condition or adverse symptom attributable thereto.

As used herein, a "therapeutically effective amount" of a compound or composition or combination refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

In some embodiments, a decrease in expression of one or markers refers to loss of 1 $\log^{10}$ in the mean fluorescence intensity and/or decrease of percentage of cells that exhibit the marker of at least about 20% of the cells, 25% of-the cells, 30% of the cells, 35% of the cells, 40% of the cells, 45% of the cells, 50% of the cells, 55% of the cells, 60% of the cells, 65% of the cells, 70% of the cells, 75% of the cells, 80% of the cells, 85% of the cells, 90% of the cell, 95% of the cells, and 100% of the cells and any % between 20 and 100% when compared to a reference cell population. In some embodiments, a cell population positive for one or markers refers to a percentage of cells that exhibit the marker of at least about 50% of the cells, 55% of the cells, 60% of the cells, 65% of the cells, 70% of the cells, 75% of the cells, 80% of the cells, 85% of the cells, 90% of the cell, 95% of the cells, and 100% of the cells and any % between 50 and 100% when compared to a reference cell population.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

IV. Exemplary Embodiments

Among the embodiments provided herein are:

1. An engineered immune cell comprising:
a genetically engineered antigen receptor that specifically binds to a target antigen; and
a disruption in a gene encoding the target antigen, said disruption resulting in reduced expression of the target antigen in the engineered immune cell.

2. The engineered immune cell of embodiment 1, wherein the target antigen is an antigen expressed on the surface or by resting T cells, activated T cells, or both.

3. The engineered immune cell of embodiment 1 or embodiment 2, wherein the target antigen is expressed on the cell surface in a cancer.

4. The engineered immune cell of embodiment 3, wherein the cancer is a hematologic cancer, an immune cancer, a leukemia, a lymphoma, and/or a myeloma.

5. The engineered immune cell of embodiment 4, wherein the target antigen is expressed in multiple myeloma.

6. The engineered immune cell of any of embodiments 1-5, wherein the target antigen is CD38.

7. The engineered cell of any of embodiments 1-5, wherein the target antigen is CD33 or TIM-3 or wherein the target antigen is CD26, CD30, CD53, CD92, CD100, CD148, CD150, CD200, CD261, CD262, or CD362.

8. The engineered immune cell of embodiment 1 or embodiment 2, wherein the target antigen is an intracellular protein antigen expressed in a cancer.

9. The engineered cell of embodiment 8, wherein the target antigen is a universal tumor antigen.

10. The engineered cell of embodiment 9, wherein the universal tumor antigen is human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53 or cyclin (D1).

11. The engineered cell of embodiment 9 or embodiment 10, wherein the universal tumor antigen is hTERT or survivin.

12. The cell of any of embodiments 1-11, wherein the genetically engineered antigen receptor is a T cell receptor (TCR) or a functional non-TCR antigen recognition receptor.

13. The cell of any of embodiments 1-12, wherein the genetically engineered antigen receptor is a chimeric antigen receptor (CAR).

14. The cell of embodiment 13, wherein:
the CAR comprises an extracellular antigen-recognition domain that specifically binds to the target antigen and an intracellular signaling domain comprising an ITAM.

15. The cell of embodiment 1-7, wherein the genetically engineered antigen receptor is a chimeric antigen receptor (CAR) comprising an extracellular antigen-recognition domain that specifically binds to the target antigen.

16. The cell of any of embodiments 1-2 and 8-11, wherein the genetically engineered antigen receptor is a T cell receptor (TCR).

17. The cell of any of embodiments 1-2 and 8-11, wherein the genetically engineered antigen receptor is a TCR-like chimeric antigen receptor (CAR) comprising an extracellular antigen-recognition domain that specifically binds to a peptide of the target antigen in the context of a major histocompatibility complex (MHC) molecule.

18. The cell of any of embodiments 1-17, wherein the genetically engineered antigen receptor is capable of inducing an activating signal to the cell.

19. The cell of embodiment 18, wherein the genetically engineered antigen receptor comprises an intracellular domain with an ITAM-containing motif.

20. The cell of embodiment 19, wherein the intracellular signaling domain comprises an intracellular domain of a CD3-zeta (CD3ζ) chain.

21. The cell of any of embodiments 18-20, wherein the genetically engineered receptor is a CAR or a TCR-like CAR and further comprises a costimulatory signaling region.

22. The cell of embodiment 21, wherein the costimulatory signaling region comprises a signaling domain of CD28.

23. The cell of any of embodiments 1-22, further comprising another genetically engineered antigen receptor, which is a chimeric costimulatory receptor that specifically binds to another antigen and is capable of inducing a costimulatory signal to the cell.

24. The cell of embodiment 23, wherein the target antigen and said another antigen are distinct and are selected, individually, from the group consisting of CD38 and CD138.

25. The cell of embodiment 1 or embodiment 2, wherein the genetically engineered antigen receptor is capable of inducing an inhibitory or immunosuppressive or repressive signal to the cell upon recognition of the target antigen.

26. The cell of embodiment 25, wherein the antigen is an antigen that is not expressed on the surface of a cancer cell or infected cell or the expression of which is downregulated on a cancer cell or an infected cell.

27. The cell of embodiment 25 or embodiment 26, wherein the antigen is an MHC-class I molecule.

28. The cell of any of embodiments 25-27, wherein the genetically engineered antigen receptor is a T cell receptor (TCR) or a functional non-TCR antigen recognition receptor.

29. The cell of any of embodiments 25-27, wherein the genetically engineered antigen receptor is a chimeric antigen receptor (CAR).

30. The cell of embodiment 29, wherein the CAR comprises an extracellular antigen-recognition domain that specifically binds to the target antigen and an intracellular signaling domain that comprises a signaling portion of an immune checkpoint molecule.

31. The cell of embodiment 30, wherein the immune checkpoint molecule is PD-1 or CTLA4.

32. The cell of any of embodiments 25-31, wherein the cell further comprises an additional genetically engineered antigen receptor which recognizes an antigen expressed on a disease or condition to be treated and induces a stimulatory or activating signal, which is dampened by the first genetically engineered antigen receptor.

33. The cell of any of embodiments 1-32, wherein the target antigen is a gene product that is naturally expressed in the cell type of the engineered cell.

34. The cell of any of embodiments 1-33, wherein expression of the target antigen in the engineered immune cell is reduced by at least 50, 60, 70, 80, 90, or 95% as compared to the expression in the immune cell in the absence of said gene disruption.

35. The cell of any of embodiments 1-34, wherein the disruption comprises a deletion of at least a portion of at least one exon of the gene.

36. The cell of any of embodiments 1-35, wherein:
the disruption comprises a deletion, mutation, and/or insertion in the gene resulting in the presence of a premature stop codon in the gene; and/or
the disruption comprises a deletion, mutation, and/or insertion within a first or second exon of the gene.

37. The cell of any of embodiments 1-36, wherein the immune cell is a T cell or an NK cell.

38. The cell of embodiment 37, wherein the immune cell is a CD4+ or CD8+ T cell.

39. The cell of any of embodiments 1-38, wherein the cell is an induced pluripotent stem cell (iPS cell).

40. A pharmaceutical composition comprising the cell of any of embodiments 1-39 and a pharmaceutically acceptable carrier.

41. A method of treatment, comprising administering to a subject having a disease or condition the cell of any of embodiments 1-39 or the pharmaceutical composition of embodiment 40.

42. The method of embodiment 41, wherein the disease or condition is multiple myeloma.

43. The method of embodiment 41 or 42, wherein said administration ameliorates one or more symptoms of the disease or condition in the subject.

44. A method of producing a genetically engineered immune cell, comprising:
(a) introducing into an immune cell a genetically engineered antigen receptor that specifically binds to a target antigen; and
(b) effecting repression of expression of the target antigen in the immune cell,
thereby producing a genetically engineered immune cell in which expression of the target antigen is repressed,
wherein steps (a) and (b) are carried out simultaneously or sequentially in any order.

45. The method of embodiment 44, wherein the effecting in (b) comprises disrupting a gene encoding the target antigen.

46. The method of embodiment 45, wherein:
the disruption comprises disrupting the gene at the DNA level and/or
the disruption is not reversible; and/or
the disruption is not transient.

47. The method of embodiment 45 or 46, wherein the disruption comprises introducing into the immune cell a DNA binding protein or DNA-binding nucleic acid that specifically binds to or hybridizes to the gene.

48. The method of embodiment 47, wherein the disruption comprises introducing: (a) a fusion protein comprising a DNA-targeting protein and a nuclease or (b) an RNA-guided nuclease.

49. The method of embodiment 48, wherein the DNA-targeting protein or RNA-guided nuclease comprises a zinc finger protein (ZFP), a TAL protein, or a clustered regularly interspaced short palindromic nucleic acid (CRISPR) specific for the gene.

50. The method of any of embodiments 47-49, wherein the disruption comprises introducing a zinc finger nuclease (ZFN), a TAL-effector nuclease (TALEN), or and a CRISPR-Cas9 combination that specifically binds to, recognizes, or hybridizes to the gene.

51. The method of any of embodiments 47-50, wherein the introducing is carried out by introducing into the cell a nucleic acid comprising a sequence encoding the DNA-binding protein, DNA-binding nucleotide, and/or complex comprising the DNA-binding protein or DNA-binding nucleotide.

52. The method of embodiment 51, wherein the nucleic acid is a viral vector.

53. The method of any of embodiments 47-52, wherein the specific binding to the gene is within an exon of the gene and/or is within a portion of the gene encoding an N-terminus of the target antigen.

54. The method of any of embodiments 47-53, wherein the introduction thereby effects a frameshift mutation in the gene and/or an insertion of an early stop codon within the coding region of the gene.

55. The method of any of embodiments 44-54, wherein the target antigen is a gene product that is naturally expressed in the immune cell and/or the expression of which is induced by said introduction of said genetically engineered antigen receptor.

56. The method of any of embodiments 44-55, wherein said repression reduces expression of the target antigen in the engineered immune cell by at least 50, 60, 70, 80, 90, or 95% as compared to an engineered cell produced by the method in the absence of the repression.

57. The method of any of embodiments 44-56 wherein the immune cell is a T cell.

58. The method of embodiment 57, wherein the immune cell is a CD4+ or CD8+ T cell.

59. The method of any of embodiments 44-58, wherein the target antigen is an antigen expressed by resting T cells, activated T cells, or both.

60. The method of any of embodiments 44-59, wherein the target antigen is expressed in multiple myeloma.

61. The method of any of embodiments 44-60, wherein the target antigen is CD38.

62. The method of any of embodiments 44-59, wherein the target antigen is an intracellular protein antigen expressed in a cancer.

63. The method of embodiment 62, wherein the target antigen is a universal tumor antigen.

64. The method of embodiment 63, wherein the universal tumor antigen is human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53 or cyclin (D1).

65. The method of embodiment 63 or embodiment 64, wherein the universal tumor antigen is hTERT or survivin.

66. The method of any of embodiments 44-65, wherein the genetically engineered immune cell produced by the method comprises the cell of any of embodiments 1-39.

67. The method of any of embodiments 44-66, further comprising:
(c) introducing into the immune cell another genetically engineered antigen receptor, which is a chimeric costimulatory receptor that specifically binds to another antigen and is capable of inducing a costimulatory signal to the cell, wherein steps (a), (b) and (c) are carried out simultaneously or sequentially in any order.

68. The method of embodiment 67, wherein the genetically engineered cell comprises the cell of any of embodiments 25-32.

69. The method of any of embodiments 44-68, wherein the introduction in (a) is carried out by introducing a nucleic acid comprising a sequence encoding the genetically engineered antigen receptor.

70. The method of embodiment 69, wherein the nucleic acid is a viral vector.

71. The method of any of embodiments 44-70, wherein the genetically engineered antigen receptor is a T cell receptor (TCR) or a functional non-TCR antigen recognition receptor.

72. The method of any of embodiments 44-71, wherein the genetically engineered antigen receptor is a chimeric antigen receptor (CAR).

73. A cell produced by the method of any of embodiments 44-72.

74. An engineered immune cell, comprising:
(a) a first genetically engineered antigen receptor, which specifically binds to a first antigen and is capable of inducing an activating signal to the cell; and
(b) a second genetically engineered antigen receptor, which is a chimeric costimulatory receptor that specifically binds to a second antigen and is capable of inducing a costimulatory signal to the cell,
wherein the first and second antigens are distinct and, individually, are selected from the group consisting of CD38, CS-1, and CD138.

75. An engineered immune cell, comprising:
(a) a first genetically engineered antigen receptor, which specifically binds to a first antigen and is capable of inducing an activating signal to the cell; and
(b) a second genetically engineered antigen receptor, which is a chimeric costimulatory receptor that specifically binds to a second antigen and is capable of inducing a costimulatory signal to the cell,
wherein the first and second antigens are distinct and, individually, are selected from the group consisting of CD38 and CD138.

76. An engineered immune cell, comprising:
(a) a first genetically engineered antigen receptor that specifically binds to a first antigen and is capable of inducing an activating signal to the cell; and
(b) a second genetically engineered antigen receptor which is a chimeric costimulatory receptor that specifically binds to a second antigen and is capable of inducing a costimulatory signal to the cell,
wherein the first and second antigens are distinct and the first or the second antigen is CS-1.

77. The engineered immune cell of embodiment 76, wherein the second antigen is an antigen expressed in multiple myeloma.

78. An engineered immune cell, comprising:
(a) a first genetically engineered antigen receptor that specifically binds to a first antigen and is capable of inducing an activating signal to the cell; and
(b) a second genetically engineered antigen receptor which is a chimeric costimulatory receptor that specifically binds to a second antigen and is capable of inducing a costimulatory signal to the cell,
wherein the first and second antigens are distinct and at least one of the first or the second antigen is a universal tumor antigen.

79. The engineered immune cell of embodiment 78, wherein the universal tumor antigen is human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53 or cyclin (D1).

80. The engineered immune cell of embodiment 78 or embodiment 79, wherein the universal tumor antigen is hTERT or survivin.

81. The engineered immune cell of embodiment any of embodiments 78-80, wherein the other of the first or second antigen is an antigen expressed in a tumor.

82. The engineered immune cell of any of embodiments 74-81, wherein the first genetically engineered antigen receptor comprises an ITAM-containing sequence.

83. The engineered immune cell of embodiment 82, wherein the first genetically engineered antigen receptor comprises an intracellular signaling domain of a CD3-zeta (CD3ζ) chain.

84. The engineered immune cell of embodiment 82 or embodiment 83, wherein the first genetically engineered antigen receptor does not comprise a signaling domain from a T cell costimulatory molecule.

85. The engineered immune cell of any of embodiments 74-84, wherein the costimulatory receptor comprises an intracellular signaling domain of a T cell costimulatory molecule.

86. The engineered immune cell of embodiment 85, wherein the T cell costimulatory molecule comprises one or more molecules selected from the group consisting of CD28 and 41BB.

87. The engineered immune cell of any of embodiments 74, 77 and 82-86, wherein:
(a) the first antigen is CD38 and the second antigen is CD138;
(b)) the first antigen is CD38 and the second antigen is CS-1;
(c) the first antigen is CD138 and the second antigen is CD38;
(d) the first antigen is CD138 and the second antigen is CS-1;
(e) the first antigen is CS-1 and the second antigen is CD38;
(6) the first antigen is CS-1 and the second antigen is CD138.

88. The engineered immune cell of any of embodiments 74-87, further comprising a third genetically engineered antigen receptor recognizing a third antigen.

89. The engineered immune cell of any of embodiments 74-88, wherein the first genetically engineered antigen receptor contains an extracellular antigen recognition domain which specifically binds to the first target antigen at a dissociation constant ($K_D$) of at least $10^{-8}$ M, at least $10^{-7}$ M, at least $10^{-6}$ M, at least $10^{-5}$ M, $10^{-5}$ M, or $10^{-4}$ M.

90. The engineered immune cell of any of embodiments 74-89, wherein ligation of the first genetically engineered antigen receptor and ligation of the second genetically engineered antigen receptor induces a response in the cell, which response is not induced by ligation of either of the genetically engineered antigen receptors alone.

91. The engineered immune cell of embodiment 90, wherein said response is selected from the group consisting of proliferation, secretion of a cytokine, and cytotoxic activity.

92. The engineered immune cell of any of embodiments 74-91, further comprising a disruption in a gene encoding the first antigen, and/or in a gene encoding the second antigen, said disruption resulting in reduced expression of the first and/or second antigen in the engineered immune cell.

93. The engineered immune cell of embodiment 92, wherein the gene disrupted encodes CD38.

94. The engineered immune cell of embodiment 92, wherein the gene disrupted encodes a universal tumor antigen.

95. The engineered immune cell of any of embodiments 92-94, wherein expression of the first and/or second antigen in the engineered immune cell is reduced by at least 50, 60, 70, 80, 90, or 95% as compared to the expression in the immune cell in the absence of said gene disruption.

96. The engineered immune cell of any of embodiments 92-95, wherein:
the disruption comprises a deletion of at least an exonic portion of the gene;
the disruption comprises a deletion, mutation, and/or insertion in the gene resulting in the presence of an early stop codon in the gene; and/or
the disruption comprises a deletion, mutation, and/or insertion within a first or second exon of the gene.

97. The engineered immune cell of any of embodiments 74-96, wherein the immune cell is a T cell or an NK cell.

98. The engineered immune cell of embodiment 97, wherein the immune cell is a CD4+ or CD8+ T cell, or is an iPS cell.

99. The engineered immune cell of any of embodiments 74-98, wherein the first genetically engineered antigen receptor is a T cell receptor (TCR) or a functional non-TCR antigen recognition receptor.

100. The engineered immune cell of embodiment 99, wherein the first genetically engineered antigen receptor is a chimeric antigen receptor (CAR).

101. A pharmaceutical composition comprising the engineered immune cell of any of embodiments 74-100 and a pharmaceutically acceptable carrier.

102. A method of treatment, comprising administering to a subject having a disease or condition the engineered immune cell of any of embodiments 74-100 or the pharmaceutical composition of embodiment 101.

103. The method of embodiment 102, wherein the disease or condition is multiple myeloma.

104. The method of embodiment 102 or 103, wherein said administration ameliorates one or more symptoms of the disease or condition in the subject.

105. The method of any of embodiments 41-43 and 102-104, wherein the genetically engineered antigen receptor or receptors specifically binds to an antigen associated with the disease or condition.

106. The method of embodiment 105, wherein the disease or condition is a cancer.

107. A pharmaceutical composition comprising cells of any of embodiments 1-39 and 54-100 or the pharmaceutical composition of embodiment 40 or embodiment 101 for use in treating a disease or condition in a subject.

108. Use of a composition comprising cells of any of embodiments 1-30 and 54-100 or of embodiment 40 or embodiment 101 for the manufacture of a medicament for treating a disease or condition in a subject.

109. The composition of embodiment 107 or use of embodiment 108, wherein the genetically engineered antigen receptor or receptors specifically binds to an antigen associated with the disease or condition.

110. The composition or use of any of embodiments 107-109, wherein the disease or condition is a cancer.

111. A method of producing an engineered immune cell, the method comprising:
(a) introducing into an immune cell a first genetically engineered antigen receptor that specifically binds to a first antigen; and
(b) introducing into the immune cell a second genetically engineered antigen receptor, which is a chimeric costimulatory receptor and specifically binds to a second antigen, thereby producing the engineered immune cell,
wherein said first and second antigens are distinct and, individually, are selected from the group consisting of CD38, CS-1, and CD138 and (a) and (b) are carried out simultaneously or sequentially in any order.

112. A method of producing an engineered immune cell, the method comprising:
(a) introducing into an immune cell a first genetically engineered antigen receptor that specifically binds to a first antigen; and
(b) introducing into the immune cell a second genetically engineered antigen receptor which is a chimeric costimulatory receptor that specifically binds to a second antigen, thereby producing the engineered immune cell
wherein said first and second antigens are distinct and, individually, are selected from the group consisting of CD38 and CD138 and (a) and (b) are carried out simultaneously or sequentially in any order.

113. A method of producing a genetically engineered immune cell, the method comprising:
(a) introducing into an immune cell a first genetically engineered antigen receptor that specifically binds to a first antigen; and
(b) introducing into the immune cell a second genetically engineered antigen receptor, which is a chimeric costimulatory receptor and specifically binds to a second antigen, thereby producing the engineered immune cell,
wherein the first and second antigens are distinct and the first or the second antigen is CS1-1 and (a) and (b) are carried out simultaneously or sequentially in any order.

114. A method of producing a genetically engineered immune cell, the method comprising:
(a) introducing into an immune cell a first genetically engineered antigen receptor that specifically binds to a first antigen; and
(b) introducing into the immune cell a second genetically engineered antigen receptor, which is a chimeric costimulatory receptor and specifically binds to a second antigen, thereby producing the engineered immune cell,
wherein the first and second antigens are distinct and at least the first or the second antigens is a universal tumor antigen and (a) and (b) are carried out simultaneously or sequentially in any order.

115. The method of embodiment 114, wherein the universal tumor antigen is human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53 or cyclin (D1).

116. The method of embodiment 114 or embodiment 115, wherein the universal tumor antigen is hTERT or survivin.

117. The method of any of embodiments 113-116, wherein the other of the first or second antigen is an antigen expressed in a tumor.

118. The method of any of embodiments 113-117, wherein said introducing in (a) and/or said introducing in (b) is carried out by introducing into the immune cell one or more nucleic acids encoding the first and/or second genetically engineered antigen receptor(s).

119. The method of embodiment 118, wherein the nucleic acid(s) comprises a viral vector.

120. The method of any of embodiments 113-119, further comprising (c) effecting repression of expression of the first and/or second antigen in the immune cell.

121. The method of any of embodiments 113-120, wherein the engineered immune cell comprises the cell of any of embodiments 74-100.

122. The method of embodiment 85, wherein the effecting in (c) comprises disrupting a gene encoding the first or second antigen.

123. The method of embodiment 122, wherein:
the disruption comprises disrupting the gene at the DNA level and/or
the disruption is not reversible; and/or
the disruption is not transient.

124. The method of embodiment 122 or 123, wherein the disruption comprises introducing into the immune cell a DNA binding protein or DNA-binding nucleic acid that specifically binds to or hybridizes to the gene.

125. The method of embodiment 124, wherein the DNA binding protein or DNA-binding nucleic acid comprises: (a) a fusion protein comprising a DNA-targeting protein and a nuclease or (b) an RNA-guided nuclease.

126. The method of embodiment 125, wherein the DNA-binding protein or DNA-binding nucleic acid comprises a zinc finger protein (ZFP), a TAL protein, or a clustered regularly interspaced short palindromic nucleic acid (CRISPR) specific for the gene.

127. The method of embodiments 124-126, wherein the disruption comprises introducing a D a zinc finger nuclease (ZFN), a TAL-effector nuclease (TALEN), or and a CRISPR-Cas9 combination that specifically binds to, recognizes, or hybridizes to the gene.

128. The method of any of embodiments 124-127, wherein the introducing is carried out by introducing into the cell a nucleic acid comprising a sequence encoding the DNA-binding protein, DNA-binding nucleotide, and/or complex comprising the DNA-binding protein or DNA-binding nucleotide.

129. The method of embodiment 128, wherein the nucleic acid is a viral vector.

130. The method of any of embodiments 124-129, wherein the specific binding to the gene is within an exon of the gene and/or is within a portion of the gene encoding an N-terminus of the target antigen.

131. The method of any of embodiments 124-130, wherein the introduction thereby effects a frameshift mutation in the gene and/or an insertion of an early stop codon within the coding region of the gene.

132. The method of any of embodiments 111-131, wherein said repression reduces expression of the target antigen in the engineered immune cell by at least 50, 60, 70, 80, 90, or 95% as compared to an engineered cell produced by the method in the absence of the repression.

133. A cell produced by the method of any of embodiments 111-132.

134. The engineered immune cell of any of claims 1-39, wherein the genetic disruption comprises a disruption in a gene encoding the target antigen.

135. The engineered immune cell of any of claims 1-39 or claim 134, wherein, the cells exhibit less than 40%, 50%, 60%, 70%, 80%, 90% or less fratricide killing compared to cells expressing the antigen receptor but without the gene disruption.

136. The engineered immune cell of claim 135, wherein fratricide killing is assessed by an assay that measures cell viability, proliferation or cytotoxicity.

V. Examples

The following examples are included for illustrative purposes only and are not intended to limit the scope of the invention.

Example 1: Assessment of Cytotoxic Activity of T-Cells Engineered with a Chimeric Antigen Receptor (CAR) Specific for hTERT in the Presence of Absence of Endogenous hTERT Repression Exemplary studies are carried out to assess of T cells expressing an engineered antigen receptor specific for a particular antigen, which is expressed in or on T cells, following repression of the expression of and/or genetic disruption or knockout of such antigen in the T cells. This exemplary study is carried out by disrupting expression of the universal tumor protein antigen, human telomerase reverse transcriptase (hTERT). In other studies, similar methods are carried out by disrupting other antigen targets of interest (in cells expressing a genetically engineered antigen receptor recognizing such antigen), such as other universal protein antigens (e.g. survivin) and/or other antigens of interest including those naturally expressed in T cells and/or activated T cells (e.g. CD38).

T cells are isolated by immunoaffinity-based selection from a human apheresis product sample from a subject expressing the HLA-A*0201 allele, such as, in some cases, a subject having a cancer. The resulting cells are activated using an anti-CD3/anti-CD28 reagent in the presence of IL-2 (100 IU/mL), for example, for 72 hours at 37° C.

The CRISPR/Cas9 technology is used to knock-down gene expression of hTERT in the activated T cells. In an exemplary method, Cas9 nuclease (e.g., that encoded by mRNA from *Staphylococcus aureus* or from *Streptococcus pyogenes*, e.g. pCW-Cas9, Addgene #50661, Wang et al. (2014) Science, 3:343-80-4; or nuclease or nickase lentiviral vectors available from Applied Biological Materials (ABM; Canada) as Cat. No. K002, K003, K005 or K006) and hTERT guide RNA (gRNA, e.g. exemplary gRNA vector available from ABM, Cat. No. K0009811) are introduced into cells, for example, using lentiviral delivery vectors or any of a number of known delivery method or vehicle for transfer to cells, such as any of a number of known methods or vehicles for delivering Cas9 molecules and guide RNAs. Non-specific or empty vector control T cells also are generated. Degree of Knockout of hTERT (e.g., 24 to 72 hours after transfer) is assessed using any of a number of well-known assays for assessing gene disruption in cells.

Within 24 to 96 hours after transduction of CRISPR/Cas9 system, cells (hTERT knock-down and control cells) are transduced with an empty vector or with a viral vector encoding an hTERT antigen receptor, such as a T cell receptor (TCR) or an anti-hTERT chimeric TCR-like antibody or binding fragment thereof (e.g. scFv), that specifically bind an hTERT-derived peptide epitope in the context of HLA-A*0201, e.g. as described in U.S. Pat. No. 7,718,777, including antibody binding molecules specific for any of the peptides set forth in SEQ ID NOS: 7, 8 or 10-14. Thus, in total, four groups of cells are generated as follows: 1) hTERT knockout (without genetically engineered receptor); 2) hTERT knockout/genetically engineered hTERT-antigen receptor; 3) hTERT wildtype T cells/genetically engineered hTERT-antigen receptor; and hTERT wildtype (without genetically engineered receptor) (control).

Following the introduction, cells are further cultured, generally at 37 degrees C., for example, to allow for cell expansion. Antigen-induced cytotoxicity and/or activation of cells in the culture of each group is assessed by performing a cell proliferation assay, a chromium release assay, ELISPOT assay for IFN-γ, granzyme B and/or perforin and/or an assay for cell viability, such as by using CellTiter-Glo® (CTG)-assay or other assay that measures proliferation, viability and/or cytotoxicity of cells. The cytotoxicity of cells is compared among the different groups of generated cells. As a positive control for cytotoxicity or activation or other function, cells known to express hTERT and/or to present a peptide derived therefrom recognize by the cell, are included to confirm the hTERT-specific function(s) of the engineered cells assessed.

In additional studies, cells in the various condition groups are administered to animal subjects and their persistence followed over time and compared, to assess impacts of the knockout on self-killing by such cells and persistence of such cells over time, and efficacy in targeting cells expressing the target antigen, such as tumor cells.

Optionally, autologous hTERT knockout/hTERT-antigen specific T cells engineered as above, which are found to avoid or exhibit reduced potential for self-killing in culture, are administered to the subject to treat the cancer at a dosage of, for example, $1 \times 10^7$ cells to $5 \times 10^{10}$ cells.

The present invention is not to be limited in scope by the embodiments disclosed herein, which are intended as single illustrations of individual aspects of the invention, and any that are functionally equivalent are within the scope of the invention. Various modifications to the compositions and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

The invention claimed is:

1. An engineered immune cell comprising:
   a heterologous nucleic acid encoding a recombinant receptor that specifically binds to a target antigen, wherein the target antigen is Wilms' tumor gene 1 (WT1); and
   a genetic disruption in an endogenous gene encoding the target antigen, wherein the genetic disruption results in knockout of the endogenous gene encoding the target antigen in the engineered immune cell.

2. The engineered immune cell of claim 1, wherein the encoded recombinant receptor is a chimeric antigen receptor (CAR) comprising an extracellular antigen-recognition domain that specifically binds to the target antigen.

3. The engineered immune cell of claim 2, wherein the CAR comprises an intracellular signaling domain comprising a CD3-zeta (CD3ζ) chain and a costimulatory signaling region.

4. The engineered immune cell of claim 3, wherein the costimulatory signaling region comprises one or more signaling domains selected from the group consisting of CD28 signaling domain and 41BB signaling domain.

5. The engineered immune cell of claim 2, wherein the immune cell is a T cell.

6. The engineered immune cell of claim 5, wherein the T cell is a CD4+ T cell or a CD8+ T cell.

7. The engineered immune cell of claim 1, wherein the encoded recombinant receptor is a CAR comprising an extracellular antigen-recognition domain that specifically binds to a peptide of the target antigen complexed with a major histocompatibility complex (WIC) molecule.

8. The engineered immune cell of claim 7, wherein the CAR comprises an intracellular signaling domain comprising a CD3ζ chain and a costimulatory signaling region.

9. The engineered immune cell of claim 8, wherein the costimulatory signaling region comprises one or more signaling domains selected from the group consisting of CD28 signaling domain and 41BB signaling domain.

10. The engineered immune cell of claim 7, wherein the immune cell is a T cell.

11. The engineered immune cell of claim 10, wherein the T cell is a CD4+ T cell or a CD8+ T cell.

12. The engineered immune cell of claim 1, wherein the encoded recombinant receptor is a T cell receptor (TCR).

13. The engineered immune cell of claim 12, further comprising a second heterologous nucleic acid encoding a second recombinant receptor, which is a chimeric costimulatory receptor that specifically binds to a second antigen and is capable of inducing a costimulatory signal in the cell, wherein the second antigen is expressed on a tumor type that expresses the target antigen and is distinct from the target antigen.

14. The engineered immune cell of claim 12, wherein the immune cell is a T cell.

15. The engineered immune cell of claim 14, wherein the T cell is a CD4+ T cell or a CD8+ T cell.

16. The engineered immune cell of claim 1, further comprising a second heterologous nucleic acid encoding a second recombinant receptor, which is a chimeric costimulatory receptor that specifically binds to a second antigen and is capable of inducing a costimulatory signal in the cell, wherein the second antigen is expressed on a tumor type that expresses the target antigen and is distinct from the target antigen.

17. The engineered immune cell of claim 1, wherein the encoded recombinant receptor is capable of inducing inhibitory, immunosuppressive or repressive signal to the cell upon recognition of the target antigen.

18. The engineered immune cell of claim 17, wherein the encoded recombinant receptor is a CAR and the CAR comprises an extracellular antigen-recognition domain that specifically binds to the target antigen and an intracellular signaling domain that comprises a signaling portion of an immune checkpoint molecule.

19. The engineered immune cell of claim 17, wherein the encoded recombinant receptor is a first recombinant receptor, the target antigen is a first target antigen, and the immune cell further comprises a second nucleic acid encoding a second recombinant receptor that recognizes a second target antigen, and induces a stimulatory or an activating signal, wherein the stimulatory or the activating signal is dampened by a signal induced by the inhibitory, the immunosuppressive or the repressive signal induced by the first recombinant receptor, wherein the second target antigen is expressed on a tumor type that expresses the first target antigen and is distinct from the first target antigen.

20. The engineered immune cell of claim 1, wherein the immune cell is a T cell or an NK cell.

21. The engineered immune cell of claim 20, wherein the T cell is a CD4+ T cell or a CD8+ T cell.

* * * * *

SEQUENCE LISTING

<160> NUMBER OF SEQ ID NOS: 30

<210> SEQ ID NO 1
<211> LENGTH: 300
<212> TYPE: PRT
<213> ORGANISM: Homo sapiens
<220> FEATURE:
<223> OTHER INFORMATION: CD38; GenBank: BAA18966

<400> SEQUENCE: 1

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Leu Ala Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
210                 215                 220

Val Glu Val His Asn Leu Gln Pro Gly Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
290                 295                 300

<210> SEQ ID NO 2
<211> LENGTH: 1494
<212> TYPE: DNA
<213> ORGANISM: Homo sapiens
<220> FEATURE:
<221> NAME/KEY: CDS
<222> LOCATION: (108)...(1010)
<223> OTHER INFORMATION: CD38; GenBank NM_001775.2

<400> SEQUENCE: 2

| | | |
|---|---|---|
| agtgaaacag aaggggaggt gcagtttcag aacccagcca gcctctctct tgctgcctag | 60 |
| cctcctgccg gcctcatctt cgcccagcca accccgcctg gagccct atg gcc aac<br>                                                                                                                                Met Ala Asn<br>                                                                                                                                  1 | 116 |
| tgc gag ttc agc ccg gtg tcc ggg gac aaa ccc tgc tgc cgg ctc tct<br>Cys Glu Phe Ser Pro Val Ser Gly Asp Lys Pro Cys Cys Arg Leu Ser<br> 5                             10                         15 | 164 |
| agg aga gcc caa ctc tgt ctt ggc gtc agt atc ctg gtc ctg atc ctc<br>Arg Arg Ala Gln Leu Cys Leu Gly Val Ser Ile Leu Val Leu Ile Leu<br> 20                         25                       30                      35 | 212 |
| gtc gtg gtg ctc gcg gtg gtc gtc ccg agg tgg cgc cag cag tgg agc<br>Val Val Val Leu Ala Val Val Val Pro Arg Trp Arg Gln Gln Trp Ser<br>              40                       45                       50 | 260 |
| ggt ccg ggc acc acc aag cgc ttt ccc gag acc gtc ctg gcg cga tgc<br>Gly Pro Gly Thr Thr Lys Arg Phe Pro Glu Thr Val Leu Ala Arg Cys<br>          55                       60                       65 | 308 |
| gtc aag tac act gaa att cat cct gag atg aga cat gta gac tgc caa<br>Val Lys Tyr Thr Glu Ile His Pro Glu Met Arg His Val Asp Cys Gln<br>       70                     75                       80 | 356 |
| agt gta tgg gat gct ttc aag ggt gca ttt att tca aaa cat cct tgc<br>Ser Val Trp Asp Ala Phe Lys Gly Ala Phe Ile Ser Lys His Pro Cys<br>85                      90                       95 | 404 |
| aac att act gaa gaa gac tat cag cca cta atg aag ttg gga act cag<br>Asn Ile Thr Glu Glu Asp Tyr Gln Pro Leu Met Lys Leu Gly Thr Gln<br>100                       105                   110               115 | 452 |
| acc gta cct tgc aac aag att ctt ctt tgg agc aga ata aaa gat ctg<br>Thr Val Pro Cys Asn Lys Ile Leu Leu Trp Ser Arg Ile Lys Asp Leu<br>              120                   125                 130 | 500 |
| gcc cat cag ttc aca cag gtc cag cgg gac atg ttc acc ctg gag gac<br>Ala His Gln Phe Thr Gln Val Gln Arg Asp Met Phe Thr Leu Glu Asp<br>                 135                   140               145 | 548 |
| acg ctg cta ggc tac ctt gct gat gac ctc aca tgg tgt ggt gaa ttc<br>Thr Leu Leu Gly Tyr Leu Ala Asp Asp Leu Thr Trp Cys Gly Glu Phe<br>150                       155                   160 | 596 |
| aac act tcc aaa ata aac tat caa tct tgc cca gac tgg aga aag gac<br>Asn Thr Ser Lys Ile Asn Tyr Gln Ser Cys Pro Asp Trp Arg Lys Asp<br>    165                     170                   175 | 644 |
| tgc agc aac aac cct gtt tca gta ttc tgg aaa acg gtt tcc cgc agg<br>Cys Ser Asn Asn Pro Val Ser Val Phe Trp Lys Thr Val Ser Arg Arg<br>180                       185                   190               195 | 692 |
| ttt gca gaa gct gcc tgt gat gtg gtc cat gtg atg ctc aat gga tcc<br>Phe Ala Glu Ala Ala Cys Asp Val Val His Val Met Leu Asn Gly Ser<br>               200                   205                 210 | 740 |
| cgc agt aaa atc ttt gac aaa aac agc act ttt ggg agt gtg gaa gtc<br>Arg Ser Lys Ile Phe Asp Lys Asn Ser Thr Phe Gly Ser Val Glu Val<br>               215                   220               225 | 788 |
| cat aat ttg caa cca gag aag gtt cag aca cta gag gcc tgg gtg ata<br>His Asn Leu Gln Pro Glu Lys Val Gln Thr Leu Glu Ala Trp Val Ile<br>        230                   235                   240 | 836 |
| cat ggt gga aga gaa gat tcc aga gac tta tgc cag gat ccc acc ata<br>His Gly Gly Arg Glu Asp Ser Arg Asp Leu Cys Gln Asp Pro Thr Ile<br>245                       250                   255 | 884 |
| aaa gag ctg gaa tcg att ata agc aaa agg aat att caa ttt tcc tgc<br>Lys Glu Leu Glu Ser Ile Ile Ser Lys Arg Asn Ile Gln Phe Ser Cys<br>260                       265                   270               275 | 932 |
| aag aat atc tac aga cct gac aag ttt ctt cag tgt gtg aaa aat cct<br>Lys Asn Ile Tyr Arg Pro Asp Lys Phe Leu Gln Cys Val Lys Asn Pro<br>              280                   285                 290 | 980 |

```
gag gat tca tct tgc aca tct gag atc tga gccagtcgct gtggttgttt     1030
Glu Asp Ser Ser Cys Thr Ser Glu Ile
            295                 300 tagctccttg actccttgtg gtttatgtca tcatacatga ctcagcatac ctgctggtgc  1090
agagctgaag attttggagg gtcctccaca ataaggtcaa tgccagagac ggaagccttt  1150
ttccccaaag tcttaaaata acttatatca tcagcatacc tttattgtga tctatcaata  1210
gtcaagaaaa attattgtat aagattagaa tgaaaattgt atgttaagtt acttcacttt  1270
aattctcatg tgatcctttt atgttattta tatattggta acatccttc tattgaaaaa   1330 tcaccacacc aaacctctct tattagaaca ggcaagtgaa gaaaagtgaa tgctcaagtt  1390
tttcagaaag cattacattt ccaaatgaat gaccttgttg catgatgtat ttttgtaccc  1450
ttcctacaga tagtcaaacc ataaacttca tggtcatggg taaa                   1494

<210> SEQ ID NO 3
<211> LENGTH: 1132
<212> TYPE: PRT
<213> ORGANISM: Homo sapiens
<220> FEATURE:
<223> OTHER INFORMATION: Telomerase reverse transcriptase (hTERT);
      GenBank NP_937983.2

<400> SEQUENCE: 3

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255
```

```
Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
                340                 345                 350

Ser Leu Thr Gly Ala Arg Arg Leu Val Glu Thr Ile Phe Leu Gly Ser
            355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
                500                 505                 510

Ser Val Arg Asp Cys Ala Trp Leu Arg Arg Ser Pro Gly Val Gly Cys
            515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
                580                 585                 590

Leu Lys Arg Val Gln Leu Arg Glu Leu Ser Glu Ala Glu Val Arg Gln
            595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
                660                 665                 670
```

-continued

```
Pro Gly Leu Leu Gly Ala Ser Val Leu Gly Leu Asp Asp Ile His Arg
            675                 680                 685
Ala Trp Arg Thr Phe Val Leu Arg Val Arg Ala Gln Asp Pro Pro
    690                 695                 700
Glu Leu Tyr Phe Val Lys Val Asp Val Thr Gly Ala Tyr Asp Thr Ile
705                 710                 715                 720
Pro Gln Asp Arg Leu Thr Glu Val Ile Ala Ser Ile Ile Lys Pro Gln
                725                 730                 735
Asn Thr Tyr Cys Val Arg Arg Tyr Ala Val Val Gln Lys Ala Ala His
                740                 745                 750
Gly His Val Arg Lys Ala Phe Lys Ser His Val Ser Thr Leu Thr Asp
            755                 760                 765
Leu Gln Pro Tyr Met Arg Gln Phe Val Ala His Leu Gln Glu Thr Ser
    770                 775                 780
Pro Leu Arg Asp Ala Val Val Ile Glu Gln Ser Ser Ser Leu Asn Glu
785                 790                 795                 800
Ala Ser Ser Gly Leu Phe Asp Val Phe Leu Arg Phe Met Cys His His
                805                 810                 815
Ala Val Arg Ile Arg Gly Lys Ser Tyr Val Gln Cys Gln Gly Ile Pro
            820                 825                 830
Gln Gly Ser Ile Leu Ser Thr Leu Leu Cys Ser Leu Cys Tyr Gly Asp
    835                 840                 845
Met Glu Asn Lys Leu Phe Ala Gly Ile Arg Arg Asp Gly Leu Leu Leu
            850                 855                 860
Arg Leu Val Asp Asp Phe Leu Leu Val Thr Pro His Leu Thr His Ala
865                 870                 875                 880
Lys Thr Phe Leu Arg Thr Leu Val Arg Gly Val Pro Glu Tyr Gly Cys
                885                 890                 895
Val Val Asn Leu Arg Lys Thr Val Val Asn Phe Pro Val Glu Asp Glu
                900                 905                 910
Ala Leu Gly Gly Thr Ala Phe Val Gln Met Pro Ala His Gly Leu Phe
            915                 920                 925
Pro Trp Cys Gly Leu Leu Leu Asp Thr Arg Thr Leu Glu Val Gln Ser
    930                 935                 940
Asp Tyr Ser Ser Tyr Ala Arg Thr Ser Ile Arg Ala Ser Leu Thr Phe
945                 950                 955                 960
Asn Arg Gly Phe Lys Ala Gly Arg Asn Met Arg Arg Lys Leu Phe Gly
                965                 970                 975
Val Leu Arg Leu Lys Cys His Ser Leu Phe Leu Asp Leu Gln Val Asn
            980                 985                 990
Ser Leu Gln Thr Val Cys Thr Asn Ile Tyr Lys Ile Leu Leu Leu Gln
    995                 1000                1005
Ala Tyr Arg Phe His Ala Cys Val Leu Gln Leu Pro Phe His Gln Gln
    1010                1015                1020
Val Trp Lys Asn Pro Thr Phe Phe Leu Arg Val Ile Ser Asp Thr Ala
1025                1030                1035                1040
Ser Leu Cys Tyr Ser Ile Leu Lys Ala Lys Asn Ala Gly Met Ser Leu
                1045                1050                1055
Gly Ala Lys Gly Ala Ala Gly Pro Leu Pro Ser Glu Ala Val Gln Trp
            1060                1065                1070
Leu Cys His Gln Ala Phe Leu Leu Lys Leu Thr Arg His Arg Val Thr
    1075                1080                1085
Tyr Val Pro Leu Leu Gly Ser Leu Arg Thr Ala Gln Thr Gln Leu Ser
```

```
                        1090                    1095                    1100
Arg Lys Leu Pro Gly Thr Thr Leu Thr Ala Leu Glu Ala Ala Ala Asn
1105                    1110                    1115                    1120

Pro Ala Leu Pro Ser Asp Phe Lys Thr Ile Leu Asp
                1125                    1130

<210> SEQ ID NO 4
<211> LENGTH: 4018
<212> TYPE: DNA
<213> ORGANISM: Homo sapiens
<220> FEATURE:
<221> NAME/KEY: CDS
<222> LOCATION: (59)...(3457)
<223> OTHER INFORMATION: telomerase reverse transcriptase (hTERT),
      GenBank NM_198253.2

<400> SEQUENCE: 4
caggcagcgc tgcgtcctgc tgcgcacgtg ggaagccctg gccccggcca ccccgcg       58 atg ccg cgc gct ccc cgc tgc cga gcc gtg cgc tcc ctg ctg cgc agc      106
Met Pro Arg Ala Pro Arg Cys Arg Ala Val Arg Ser Leu Leu Arg Ser
 1               5                  10                  15 cac tac cgc gag gtg ctg ccg ctg gcc acg ttc gtg cgg cgc ctg ggg      154
His Tyr Arg Glu Val Leu Pro Leu Ala Thr Phe Val Arg Arg Leu Gly
             20                  25                  30 ccc cag ggc tgg cgg ctg gtg cag cgc ggg gac ccg gcg gct ttc cgc      202
Pro Gln Gly Trp Arg Leu Val Gln Arg Gly Asp Pro Ala Ala Phe Arg
         35                  40                  45 gcg ctg gtg gcc cag tgc ctg gtg tgc gtg ccc tgg gac gca cgg ccg      250
Ala Leu Val Ala Gln Cys Leu Val Cys Val Pro Trp Asp Ala Arg Pro
     50                  55                  60 ccc ccc gcc gcc ccc tcc ttc cgc cag gtg tcc tgc ctg aag gag ctg      298
Pro Pro Ala Ala Pro Ser Phe Arg Gln Val Ser Cys Leu Lys Glu Leu
 65                  70                  75                  80 gtg gcc cga gtg ctg cag agg ctg tgc gag cgc ggc gcg aag aac gtg      346
Val Ala Arg Val Leu Gln Arg Leu Cys Glu Arg Gly Ala Lys Asn Val
                 85                  90                  95 ctg gcc ttc ggc ttc gcg ctg ctg gac ggg gcc cgc ggg ggc ccc ccc      394
Leu Ala Phe Gly Phe Ala Leu Leu Asp Gly Ala Arg Gly Gly Pro Pro
            100                 105                 110 gag gcc ttc acc acc agc gtg cgc agc tac ctg ccc aac acg gtg acc      442
Glu Ala Phe Thr Thr Ser Val Arg Ser Tyr Leu Pro Asn Thr Val Thr
        115                 120                 125 gac gca ctg cgg ggg agc ggg gcg tgg ggg ctg ctg ctg cgc cgc gtg      490
Asp Ala Leu Arg Gly Ser Gly Ala Trp Gly Leu Leu Leu Arg Arg Val
    130                 135                 140 ggc gac gac gtg ctg gtt cac ctg ctg gca cgc tgc gcg ctc ttt gtg      538
Gly Asp Asp Val Leu Val His Leu Leu Ala Arg Cys Ala Leu Phe Val
145                 150                 155                 160 ctg gtg gct ccc agc tgc gcc tac cag gtg tgc ggg ccg ccg ctg tac      586
Leu Val Ala Pro Ser Cys Ala Tyr Gln Val Cys Gly Pro Pro Leu Tyr
                165                 170                 175 cag ctc ggc gct gcc act cag gcc cgg ccc ccg cca cac gct agt gga      634
Gln Leu Gly Ala Ala Thr Gln Ala Arg Pro Pro Pro His Ala Ser Gly
            180                 185                 190 ccc cga agg cgt ctg gga tgc gaa cgg gcc tgg aac cat agc gtc agg      682
Pro Arg Arg Arg Leu Gly Cys Glu Arg Ala Trp Asn His Ser Val Arg
        195                 200                 205 gag gcc ggg gtc ccc ctg ggc ctg cca gcc ccg ggt gcg agg agg cgc      730
Glu Ala Gly Val Pro Leu Gly Leu Pro Ala Pro Gly Ala Arg Arg Arg
    210                 215                 220
```

-continued

| | | |
|---|---|---|
| ggg ggc agt gcc agc cga agt ctg ccg ttg ccc aag agg ccc agg cgt<br>Gly Gly Ser Ala Ser Arg Ser Leu Pro Leu Pro Lys Arg Pro Arg Arg<br>225                          230                          235                          240 | 778 |
| ggc gct gcc cct gag ccg gag cgg acg ccc gtt ggg cag ggg tcc tgg<br>Gly Ala Ala Pro Glu Pro Glu Arg Thr Pro Val Gly Gln Gly Ser Trp<br>                        245                          250                          255 | 826 |
| gcc cac ccg ggc agg acg cgt gga ccg agt gac cgt ggt ttc tgt gtg<br>Ala His Pro Gly Arg Thr Arg Gly Pro Ser Asp Arg Gly Phe Cys Val<br>                  260                          265                          270 | 874 |
| gtg tca cct gcc aga ccc gcc gaa gaa gcc acc tct ttg gag ggt gcg<br>Val Ser Pro Ala Arg Pro Ala Glu Glu Ala Thr Ser Leu Glu Gly Ala<br>275                          280                          285 | 922 |
| ctc tct ggc acg cgc cac tcc cac cca tcc gtg ggc cgc cag cac cac<br>Leu Ser Gly Thr Arg His Ser His Pro Ser Val Gly Arg Gln His His<br>           290                          295                          300 | 970 |
| gcg ggc ccc cca tcc aca tcg cgg cca cca cgt ccc tgg gac acg cct<br>Ala Gly Pro Pro Ser Thr Ser Arg Pro Pro Arg Pro Trp Asp Thr Pro<br>305                          310                          315                          320 | 1018 |
| tgt ccc ccg gtg tac gcc gag acc aag cac ttc ctc tac tcc tca ggc<br>Cys Pro Pro Val Tyr Ala Glu Thr Lys His Phe Leu Tyr Ser Ser Gly<br>                        325                          330                          335 | 1066 |
| gac aag gag cag ctg cgg ccc tcc ttc cta ctc agc tct ctg agg ccc<br>Asp Lys Glu Gln Leu Arg Pro Ser Phe Leu Leu Ser Ser Leu Arg Pro<br>                  340                          345                          350 | 1114 |
| agc ctg act ggc gct cgg agg ctc gtg gag acc atc ttt ctg ggt tcc<br>Ser Leu Thr Gly Ala Arg Arg Leu Val Glu Thr Ile Phe Leu Gly Ser<br>355                          360                          365 | 1162 |
| agg ccc tgg atg cca ggg act ccc cgc agg ttg ccc cgc ctg ccc cag<br>Arg Pro Trp Met Pro Gly Thr Pro Arg Arg Leu Pro Arg Leu Pro Gln<br>           370                          375                          380 | 1210 |
| cgc tac tgg caa atg cgg ccc ctg ttt ctg gag ctg ctt ggg aac cac<br>Arg Tyr Trp Gln Met Arg Pro Leu Phe Leu Glu Leu Leu Gly Asn His<br>385                          390                          395                          400 | 1258 |
| gcg cag tgc ccc tac ggg gtg ctc ctc aag acg cac tgc ccg ctg cga<br>Ala Gln Cys Pro Tyr Gly Val Leu Leu Lys Thr His Cys Pro Leu Arg<br>                  405                          410                          415 | 1306 |
| gct gcg gtc acc cca gca gcc ggt gtc tgt gcc cgg gag aag ccc cag<br>Ala Ala Val Thr Pro Ala Ala Gly Val Cys Ala Arg Glu Lys Pro Gln<br>                        420                          425                          430 | 1354 |
| ggc tct gtg gcg gcc ccc gag gag gag gac aca gac ccc cgt cgc ctg<br>Gly Ser Val Ala Ala Pro Glu Glu Glu Asp Thr Asp Pro Arg Arg Leu<br>                      435                          440                          445 | 1402 |
| gtg cag ctg ctc cgc cag cac agc agc ccc tgg cag gtg tac ggc ttc<br>Val Gln Leu Leu Arg Gln His Ser Ser Pro Trp Gln Val Tyr Gly Phe<br>450                          455                          460 | 1450 |
| gtg cgg gcc tgc ctg cgc cgg ctg gtg ccc cca ggc ctc tgg ggc tcc<br>Val Arg Ala Cys Leu Arg Arg Leu Val Pro Pro Gly Leu Trp Gly Ser<br>465                          470                          475                          480 | 1498 |
| agg cac aac gaa cgc cgc ttc ctc agg aac acc aag aag ttc atc tcc<br>Arg His Asn Glu Arg Arg Phe Leu Arg Asn Thr Lys Lys Phe Ile Ser<br>                      485                          490                          495 | 1546 |
| ctg ggg aag cat gcc aag ctc tcg ctg cag gag ctg acg tgg aag atg<br>Leu Gly Lys His Ala Lys Leu Ser Leu Gln Glu Leu Thr Trp Lys Met<br>500                          505                          510 | 1594 |
| agc gtg cgg gac tgc gct tgg ctg cgc agg agc cca ggg gtt ggc tgt<br>Ser Val Arg Asp Cys Ala Trp Leu Arg Arg Ser Pro Gly Val Gly Cys<br>                  515                          520                          525 | 1642 |
| gtt ccg gcc gca gag cac cgt ctg cgt gag gag atc ctg gcc aag ttc<br>Val Pro Ala Ala Glu His Arg Leu Arg Glu Glu Ile Leu Ala Lys Phe<br>530                          535                          540 | 1690 |

```
ctg cac tgg ctg atg agt gtg tac gtc gtc gag ctc ctc agg tct ttc      1738
Leu His Trp Leu Met Ser Val Tyr Val Val Glu Leu Leu Arg Ser Phe
545                 550                 555                 560 ttt tat gtc acg gag acc acg ttt caa aag aac agg ctc ttt ttc tac      1786
Phe Tyr Val Thr Glu Thr Thr Phe Gln Lys Asn Arg Leu Phe Phe Tyr
                565                 570                 575 cgg aag agt gtc tgg agc aag ttg caa agc att gga atc aga cag cac      1834
Arg Lys Ser Val Trp Ser Lys Leu Gln Ser Ile Gly Ile Arg Gln His
            580                 585                 590 ttg aag agg gtg cag ctg cgg gag ctg tcg gaa gca gag gtc agg cag      1882
Leu Lys Arg Val Gln Leu Arg Glu Leu Ser Glu Ala Glu Val Arg Gln
        595                 600                 605 cat cgg gaa gcc agg ccc gcc ctg ctg acg tcc aga ctc cgc ttc atc      1930
His Arg Glu Ala Arg Pro Ala Leu Leu Thr Ser Arg Leu Arg Phe Ile
    610                 615                 620 ccc aag cct gac ggg ctg cgg ccg att gtg aac atg gac tac gtc gtg      1978
Pro Lys Pro Asp Gly Leu Arg Pro Ile Val Asn Met Asp Tyr Val Val
625                 630                 635                 640 gga gcc aga acg ttc cgc aga gaa aag agg gcc gag cgt ctc acc tcg      2026
Gly Ala Arg Thr Phe Arg Arg Glu Lys Arg Ala Glu Arg Leu Thr Ser
                645                 650                 655 agg gtg aag gca ctg ttc agc gtg ctc aac tac gag cgg gcg cgg cgc      2074
Arg Val Lys Ala Leu Phe Ser Val Leu Asn Tyr Glu Arg Ala Arg Arg
            660                 665                 670 ccc ggc ctc ctg ggc gcc tct gtg ctg ggc ctg gac gat atc cac agg      2122
Pro Gly Leu Leu Gly Ala Ser Val Leu Gly Leu Asp Asp Ile His Arg
        675                 680                 685 gcc tgg cgc acc ttc gtg ctg cgt gtg cgg gcc cag gac ccg ccg cct      2170
Ala Trp Arg Thr Phe Val Leu Arg Val Arg Ala Gln Asp Pro Pro Pro
    690                 695                 700 gag ctg tac ttt gtc aag gtg gat gtg acg ggc gcg tac gac acc atc      2218
Glu Leu Tyr Phe Val Lys Val Asp Val Thr Gly Ala Tyr Asp Thr Ile
705                 710                 715                 720 ccc cag gac agg ctc acg gag gtc atc gcc agc atc atc aaa ccc cag      2266
Pro Gln Asp Arg Leu Thr Glu Val Ile Ala Ser Ile Ile Lys Pro Gln
                725                 730                 735 aac acg tac tgc gtg cgt cgg tat gcc gtg gtc cag aag gcc gcc cat      2314
Asn Thr Tyr Cys Val Arg Arg Tyr Ala Val Val Gln Lys Ala Ala His
            740                 745                 750 ggg cac gtc cgc aag gcc ttc aag agc cac gtc tct acc ttg aca gac      2362
Gly His Val Arg Lys Ala Phe Lys Ser His Val Ser Thr Leu Thr Asp
        755                 760                 765 ctc cag ccg tac atg cga cag ttc gtg gct cac ctg cag gag acc agc      2410
Leu Gln Pro Tyr Met Arg Gln Phe Val Ala His Leu Gln Glu Thr Ser
    770                 775                 780 ccg ctg agg gat gcc gtc gtc atc gag cag agc tcc tcc ctg aat gag      2458
Pro Leu Arg Asp Ala Val Val Ile Glu Gln Ser Ser Ser Leu Asn Glu
785                 790                 795                 800 gcc agc agt ggc ctc ttc gac gtc ttc cta cgc ttc atg tgc cac cac      2506
Ala Ser Ser Gly Leu Phe Asp Val Phe Leu Arg Phe Met Cys His His
                805                 810                 815 gcc gtg cgc atc agg ggc aag tcc tac gtc cag tgc cag ggg atc ccg      2554
Ala Val Arg Ile Arg Gly Lys Ser Tyr Val Gln Cys Gln Gly Ile Pro
            820                 825                 830 cag ggc tcc atc ctc tcc acg ctg ctc tgc agc ctg tgc tac ggc gac      2602
Gln Gly Ser Ile Leu Ser Thr Leu Leu Cys Ser Leu Cys Tyr Gly Asp
        835                 840                 845 atg gag aac aag ctg ttt gcg ggg att cgg cgg gac ggg ctg ctc ctg      2650
Met Glu Asn Lys Leu Phe Ala Gly Ile Arg Arg Asp Gly Leu Leu Leu
```

```
                850              855              860
cgt ttg gtg gat gat ttc ttg ttg gtg aca cct cac ctc acc cac gcg    2698
Arg Leu Val Asp Asp Phe Leu Leu Val Thr Pro His Leu Thr His Ala
865                 870                 875                 880 aaa acc ttc ctc agg acc ctg gtc cga ggt gtc cct gag tat ggc tgc    2746
Lys Thr Phe Leu Arg Thr Leu Val Arg Gly Val Pro Glu Tyr Gly Cys
                885                 890                 895 gtg gtg aac ttg cgg aag aca gtg gtg aac ttc cct gta gaa gac gag    2794
Val Val Asn Leu Arg Lys Thr Val Val Asn Phe Pro Val Glu Asp Glu
            900                 905                 910 gcc ctg ggt ggc acg gct ttt gtt cag atg ccg gcc cac ggc cta ttc    2842
Ala Leu Gly Gly Thr Ala Phe Val Gln Met Pro Ala His Gly Leu Phe
        915                 920                 925 ccc tgg tgc ggc ctg ctg ctg gat acc cgg acc ctg gag gtg cag agc    2890
Pro Trp Cys Gly Leu Leu Leu Asp Thr Arg Thr Leu Glu Val Gln Ser
    930                 935                 940 gac tac tcc agc tat gcc cgg acc tcc atc aga gcc agt ctc acc ttc    2938
Asp Tyr Ser Ser Tyr Ala Arg Thr Ser Ile Arg Ala Ser Leu Thr Phe
945                 950                 955                 960 aac cgc ggc ttc aag gct ggg agg aac atg cgt cgc aaa ctc ttt ggg    2986
Asn Arg Gly Phe Lys Ala Gly Arg Asn Met Arg Arg Lys Leu Phe Gly
                965                 970                 975 gtc ttg cgg ctg aag tgt cac agc ctg ttt ctg gat ttg cag gtg aac    3034
Val Leu Arg Leu Lys Cys His Ser Leu Phe Leu Asp Leu Gln Val Asn
            980                 985                 990 agc ctc cag acg gtg tgc acc aac atc tac aag atc ctc ctg ctg cag    3082
Ser Leu Gln Thr Val Cys Thr Asn Ile Tyr Lys Ile Leu Leu Leu Gln
        995                 1000                1005 gcg tac agg ttt cac gca tgt gtg ctg cag ctc cca ttt cat cag caa    3130
Ala Tyr Arg Phe His Ala Cys Val Leu Gln Leu Pro Phe His Gln Gln
    1010                1015                1020 gtt tgg aag aac ccc aca ttt ttc ctg cgc gtc atc tct gac acg gcc    3178
Val Trp Lys Asn Pro Thr Phe Phe Leu Arg Val Ile Ser Asp Thr Ala
1025                1030                1035                1040 tcc ctc tgc tac tcc atc ctg aaa gcc aag aac gca ggg atg tcg ctg    3226
Ser Leu Cys Tyr Ser Ile Leu Lys Ala Lys Asn Ala Gly Met Ser Leu
                1045                1050                1055 ggg gcc aag ggc gcc gcc ggc cct ctg ccc tcc gag gcc gtg cag tgg    3274
Gly Ala Lys Gly Ala Ala Gly Pro Leu Pro Ser Glu Ala Val Gln Trp
            1060                1065                1070 ctg tgc cac caa gca ttc ctg ctc aag ctg act cga cac cgt gtc acc    3322
Leu Cys His Gln Ala Phe Leu Leu Lys Leu Thr Arg His Arg Val Thr
        1075                1080                1085 tac gtg cca ctc ctg ggg tca ctc agg aca gcc cag acg cag ctg agt    3370
Tyr Val Pro Leu Leu Gly Ser Leu Arg Thr Ala Gln Thr Gln Leu Ser
    1090                1095                1100 cgg aag ctc ccg ggg acg acg ctg act gcc ctg gag gcc gca gcc aac    3418
Arg Lys Leu Pro Gly Thr Thr Leu Thr Ala Leu Glu Ala Ala Ala Asn
1105                1110                1115                1120 ccg gca ctg ccc tca gac ttc aag acc atc ctg gac tga tggccacccg    3467
Pro Ala Leu Pro Ser Asp Phe Lys Thr Ile Leu Asp
                1125                1130 cccacagcca ggccgagagc agacaccagc agccctgtca cgccgggctc tacgtcccag   3527
ggagggaggg gcggcccaca cccaggcccg caccgctggg agtctgaggc ctgagtgagt   3587
gtttggccga ggcctgcatg tccggctgaa ggctgagtgt ccggctgagg cctgagcgag   3647
tgtccagcca agggctgagt gtccagcaca cctgccgtct tcacttcccc acaggctggc   3707
gctcggctcc accccagggc cagcttttcc tcaccaggag cccggcttcc actccccaca   3767
```

```
taggaatagt ccatccccag attcgccatt gttcacccct cgccctgccc tcctttgcct    3827 tccacccca ccatccaggt ggagaccctg agaaggaccc tgggagctct gggaatttgg    3887
agtgaccaaa ggtgtgccct gtacacaggc gaggaccctg cacctggatg ggggtccctg    3947
tgggtcaaat tgggggggagg tgctgtggga gtaaaatact gaatatatga gttttttcagt  4007 tttgaaaaaa a                                                         4018
```

```
<210> SEQ ID NO 5
<211> LENGTH: 142
<212> TYPE: PRT
<213> ORGANISM: Homo sapiens
<220> FEATURE:
<223> OTHER INFORMATION: BIRC5 (survivin) GenBank NP_001159

<400> SEQUENCE: 5

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Asp Pro Ile Glu His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

Glu Lys Val Arg Arg Ala Ile Glu Gln Leu Ala Ala Met Asp
    130                 135                 140
```

```
<210> SEQ ID NO 6
<211> LENGTH: 2655
<212> TYPE: DNA
<213> ORGANISM: Homo sapiens
<220> FEATURE:
<221> NAME/KEY: CDS
<222> LOCATION: (122)...(550)
<223> OTHER INFORMATION: BIRC5 (survivin) GenBank NM_001168.2

<400> SEQUENCE: 6
cccagaaggc cgcgggggt ggaccgccta agagggcgtg cgctcccgac atgccccgcg    60
gcgcgccatt aaccgccaga tttgaatcgc gggacccgtt ggcagaggtg gcggcggcgg   120 c atg ggt gcc ccg acg ttg ccc cct gcc tgg cag ccc ttt ctc aag gac   169
  Met Gly Ala Pro Thr Leu Pro Pro Ala Trp Gln Pro Phe Leu Lys Asp
  1               5                   10                  15 cac cgc atc tct aca ttc aag aac tgg ccc ttc ttg gag ggc tgc gcc    217
His Arg Ile Ser Thr Phe Lys Asn Trp Pro Phe Leu Glu Gly Cys Ala
            20                  25                  30 tgc acc ccg gag cgg atg gcc gag gct ggc ttc atc cac tgc ccc act    265
Cys Thr Pro Glu Arg Met Ala Glu Ala Gly Phe Ile His Cys Pro Thr
        35                  40                  45 gag aac gag cca gac ttg gcc cag tgt ttc ttc tgc ttc aag gag ctg    313
Glu Asn Glu Pro Asp Leu Ala Gln Cys Phe Phe Cys Phe Lys Glu Leu
    50                  55                  60
```

| | | | | | | | | | | | | | | | | |
|---|---|---|---|---|---|---|---|---|---|---|---|---|---|---|---|---|
| gaa | ggc | tgg | gag | cca | gat | gac | gac | ccc | ata | gag | gaa | cat | aaa | aag | cat | 361 |
| Glu | Gly | Trp | Glu | Pro | Asp | Asp | Asp | Pro | Ile | Glu | Glu | His | Lys | Lys | His | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| tcg | tcc | ggt | tgc | gct | ttc | ctt | tct | gtc | aag | aag | cag | ttt | gaa | gaa | tta | 409 |
| Ser | Ser | Gly | Cys | Ala | Phe | Leu | Ser | Val | Lys | Lys | Gln | Phe | Glu | Glu | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| acc | ctt | ggt | gaa | ttt | ttg | aaa | ctg | gac | aga | gaa | aga | gcc | aag | aac | aaa | 457 |
| Thr | Leu | Gly | Glu | Phe | Leu | Lys | Leu | Asp | Arg | Glu | Arg | Ala | Lys | Asn | Lys | |
| | | 100 | | | | | 105 | | | | | 110 | | | | |

| | | | | | | | | | | | | | | | | |
|---|---|---|---|---|---|---|---|---|---|---|---|---|---|---|---|---|
| att | gca | aag | gaa | acc | aac | aat | aag | aag | aaa | gaa | ttt | gag | gaa | act | gcg | 505 |
| Ile | Ala | Lys | Glu | Thr | Asn | Asn | Lys | Lys | Lys | Glu | Phe | Glu | Glu | Thr | Ala | |
| | | | 115 | | | | | 120 | | | | | 125 | | | |

| | | | | | | | | | | | | | |
|---|---|---|---|---|---|---|---|---|---|---|---|---|---|
| gag | aaa | gtg | cgc | cgt | gcc | atc | gag | cag | ctg | gct | gcc | atg | gat | tga | 550 |
| Glu | Lys | Val | Arg | Arg | Ala | Ile | Glu | Gln | Leu | Ala | Ala | Met | Asp | | |
| 130 | | | | | 135 | | | | | 140 | | | | | |

| | | | | | |
|---|---|---|---|---|---|
| ggcctctggc | cggagctgcc | tggtcccaga | gtggctgcac | cacttccagg | gtttattccc | 610 |
| tggtgccacc | agccttcctg | tgggccccct | agcaatgtct | taggaaagga | gatcaacatt | 670 |
| ttcaaattag | atgtttcaac | tgtgctcttg | ttttgtcttg | aaagtggcac | cagaggtgct | 730 |
| tctgcctgtg | cagcgggtgc | tgctggtaac | agtggctgct | tctctctctc | tctctctttt | 790 |
| ttgggggctc | attttgctg | ttttgattcc | cgggcttacc | aggtgagaag | tgagggagga | 850 |
| agaaggcagt | gtccctttg | ctagagctga | cagctttgtt | cgcgtgggca | gagccttcca | 910 |
| cagtgaatgt | gtctggacct | catgttgttg | aggctgtcac | agtcctgagt | gtggacttgg | 970 |
| caggtgcctg | ttgaatctga | gctgcaggtt | cctatctgt | cacacctgtg | cctcctcaga | 1030 |
| ggacagtttt | tttgttgttg | tgtttttttg | tttttttttt | tttggtagat | gcatgacttg | 1090 |
| tgtgtgatga | gagaatggag | acagagtccc | tggctcctct | actgtttaac | aacatggctt | 1150 |
| tcttattttg | tttgaattgt | taattcacag | aatagcacaa | actacaatta | aaactaagca | 1210 |
| caaagccatt | ctaagtcatt | ggggaaacgg | ggtgaacttc | aggtggatga | ggagacagaa | 1270 |
| tagagtgata | ggaagcgtct | ggcagatact | ccttttgcca | ctgctgtgtg | attagacagg | 1330 |
| cccagtgagc | cgcggggcac | atgctggccg | ctcctccctc | agaaaaaggc | agtggcctaa | 1390 |
| atccttttta | aatgacttgg | ctcgatgctg | tgggggactg | gctgggctgc | tgcaggccgt | 1450 |
| gtgtctgtca | gcccaacctt | cacatctgtc | acgttctcca | cacgggggag | agacgcagtc | 1510 |
| cgcccaggtc | cccgctttct | tggaggcag | cagctcccgc | agggctgaag | tctggcgtaa | 1570 |
| gatgatggat | ttgattcgcc | ctcctccctg | tcatagagct | gcagggtgga | ttgttacagc | 1630 |
| ttcgctgaa | acctctggag | gtcatctcgg | ctgttcctga | gaataaaaa | gcctgtcatt | 1690 |
| tcaaacactg | ctgtggaccc | tactgggttt | ttaaaatatt | gtcagttttt | catcgtcgtc | 1750 |
| cctagcctgc | caacagccat | ctgcccagac | agccgcagtg | aggatgagcg | tcctggcaga | 1810 |
| gacgcagttg | tctctgggcg | cttgccagag | ccacgaaccc | cagacctgtt | tgtatcatcc | 1870 |
| gggctccttc | cgggcagaaa | caactgaaaa | tgcacttcag | acccactat | ttctgccaca | 1930 |
| tctgagtcgg | cctgagatag | acttttccct | ctaaactggg | agaatatcac | agtggttttt | 1990 |
| gttagcagaa | aatgcactcc | agcctctgta | ctcatctaag | ctgcttattt | ttgatatttg | 2050 |
| tgtcagtctg | taaatggata | cttcacttta | ataactgttg | cttagtaatt | ggctttgtag | 2110 |
| agaagctgga | aaaaatggt | tttgtcttca | actcctttgc | atgccaggcg | gtgatgtgga | 2170 |
| tctcggcttc | tgtgagcctg | tgctgtgggc | agggctgagc | tggagccgcc | cctctcagcc | 2230 |
| cgcctgccac | ggccttcct | taaaggccat | ccttaaaacc | agaccctcat | ggctaccagc | 2290 |

-continued

```
acctgaaagc ttcctcgaca tctgttaata aagccgtagg cccttgtcta agtgcaaccg    2350
cctagacttt ctttcagata catgtccaca tgtccatttt tcaggttctc taagttggag    2410
tggagtctgg gaagggttgt gaatgaggct tctgggctat gggtgaggtt ccaatggcag    2470
gttagagccc ctcgggccaa ctgccatcct ggaaagtaga gacagcagtg cccgctgccc    2530
agaagagacc agcaagccaa actggagccc ccattgcagg ctgtcgccat gtggaaagag    2590
taactcacaa ttgccaataa agtctcatgt ggttttatct aaaaaaaaaa aaaaaaaaa     2650 aaaaa                                                                2655
```

<210> SEQ ID NO 7
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: hTERT peptide T540 HLA-A 0201

<400> SEQUENCE: 7

Ile Leu Ala Lys Phe Leu His Trp Leu
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: hTERT peptide peptide T865 HLA-A 0201

<400> SEQUENCE: 8

Arg Leu Val Asp Asp Phe Leu Leu Val
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: hTERT325-333 HLA-A 0101

<400> SEQUENCE: 9

Tyr Ala Glu Thr Lys His Phe Leu Tyr
1               5

<210> SEQ ID NO 10
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: hTERT615-624 HLA-A 0201

<400> SEQUENCE: 10

Ala Leu Leu Thr Ser Arg Leu Arg Phe Ile
1               5                   10

<210> SEQ ID NO 11
<211> LENGTH: 10
<212> TYPE: PRT
<213> ORGANISM: Artificial Sequence

```
<220> FEATURE:
<223> OTHER INFORMATION: Synthetic
<220> FEATURE:
<223> OTHER INFORMATION: hTERT674-683 HLA-A 0201

<400> SEQUENCE: 11

Gly Leu Leu Gly Ala Ser Val Leu Gly Leu
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: hTERT540-548  HLA-A 0201

<400> SEQUENCE: 12

Ile Leu Ala Lys Phe Leu His Trp Leu
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: hTERT653-661 HLA-A 0201

<400> SEQUENCE: 13

Arg Leu Thr Ser Arg Val Lys Ala Leu
1               5

<210> SEQ ID NO 14
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: hTERT988-997 HLA-A 0201

<400> SEQUENCE: 14

Tyr Leu Gln Val Asn Ser Leu Gln Thr Val
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: hTERT973-981 HLA-A 0301

<400> SEQUENCE: 15

Lys Leu Phe Gly Val Leu Arg Leu Lys
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: hTERT324-332  HLA-A 2402
```

```
<400> SEQUENCE: 16

Val Tyr Ala Glu Thr Lys His Phe Leu
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: hTERT461-469  HLA-A 2402

<400> SEQUENCE: 17

Val Tyr Gly Phe Val Arg Ala Cys Leu
1               5

<210> SEQ ID NO 18
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: hTERT4-13
      HLA-B 0702

<400> SEQUENCE: 18

Ala Pro Arg Cys Arg Ala Val Arg Ser Leu
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: hTERT68-77
      HLA-B 0702

<400> SEQUENCE: 19

Ala Pro Ser Phe Arg Gln Val Ser Cys Leu
1               5                   10

<210> SEQ ID NO 20
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: Survivin38-46 (mod)
      HLA-A 01:01

<400> SEQUENCE: 20

Met Ala Glu Ala Gly Phe Ile His Tyr
1               5

<210> SEQ ID NO 21
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: Survivin 47-56 (mod)
      HLA-A 01:01
```

<400> SEQUENCE: 21

Pro Thr Glu Asn Glu Pro Asp Leu Ala Tyr
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: Survivin 95-104
      HLA-A 02:01

<400> SEQUENCE: 22

Glu Leu Thr Leu Gly Glu Phe Leu Lys Leu
1               5                   10

<210> SEQ ID NO 23
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: Survivin 96-104 (mod)
      HLA-A 02:01

<400> SEQUENCE: 23

Leu Met Leu Gly Glu Phe Leu Lys Leu
1               5

<210> SEQ ID NO 24
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: Survivin 5-14
      HLA-A 02:01

<400> SEQUENCE: 24

Thr Leu Pro Pro Ala Trp Gln Pro Phe Leu
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: Survivin 18-27 (modK)
      HLA- A 03:01

<400> SEQUENCE: 25

Arg Ile Ser Thr Phe Lys Asn Trp Pro Lys
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic
<220> FEATURE:
<223> OTHER INFORMATION: Survivin 56-62

```
        HLA-A 11:01

<400> SEQUENCE: 26

Asp Leu Ala Gln Cys Phe Phe Cys Phe Lys
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: Survivin 80-88
        HLA- A 24:02

<400> SEQUENCE: 27

Ala Tyr Ala Cys Asn Thr Ser Thr Leu
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: Survivin 20-28
        HLA- A 24:02

<400> SEQUENCE: 28

Ser Thr Phe Lys Asn Trp Pro Phe Leu
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: Survivin 6-14
        HLA- B 07:02

<400> SEQUENCE: 29

Leu Pro Pro Ala Trp Gln Pro Phe Leu
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic
<220> FEATURE:
<223> OTHER INFORMATION: Survivin 51-59
        HLA- B 35:01

<400> SEQUENCE: 30

Glu Pro Asp Leu Ala Gln Cys Phe Tyr
1               5
```